(12) United States Patent
Jarboe et al.

(10) Patent No.: US 7,604,811 B1
(45) Date of Patent: *Oct. 20, 2009

(54) ORAL-INTESTINAL VACCINES AGAINST DISEASES CAUSED BY ENTEROPATHIC ORGANISMS USING ANTIGENS ENCAPSULATED WITHIN BIODEGRADABLE-BIOCOMPATIBLE MICROSPHERES

(75) Inventors: Daniel L. Jarboe, Sebastian, FL (US); Robert H. Reid, Kensington, MD (US); Edgar C. Boedeker, Chevy Chase, MD (US); Frederick J. Cassels, Gaithersburg, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/762,757

(22) Filed: Dec. 10, 1996

Related U.S. Application Data

(63) Continuation of application No. 08/396,986, filed on Mar. 1, 1995, now abandoned, which is a continuation-in-part of application No. 07/521,945, filed on May 11, 1990, now abandoned, which is a continuation-in-part of application No. 06/590,308, filed on Mar. 16, 1984, now abandoned, said application No. 08/396,986 and a continuation-in-part of application No. 08/191,374, filed on Apr. 6, 1994, now abandoned, is a continuation of application No. 07/690,485, filed on Apr. 24, 1991, now abandoned, which is a continuation-in-part of application No. 07/521,945, filed on May 11, 1990, now abandoned.

(51) Int. Cl.
*A61K 38/108* (2006.01)
*A61K 38/04* (2006.01)
*C07K 5/00* (2006.01)
*C07K 7/00* (2006.01)

(52) U.S. Cl. .................................. 424/257.1; 530/328
(58) Field of Classification Search .............. 424/185.1, 424/241.1, 242.1; 530/300, 326–328, 352, 530/403
See application file for complete search history.

(56) References Cited

U.S. PATENT DOCUMENTS

| | | | |
|---|---|---|---|
| 3,540,444 A | 11/1970 | Moreland | |
| 3,773,919 A | 11/1973 | Boswell | |
| 3,788,315 A | 1/1974 | Laurens | |
| 4,166,800 A * | 9/1979 | Fong | 252/316 |
| 4,384,975 A | 5/1983 | Fong | |
| 4,530,840 A | 7/1985 | Tice et al. | |
| 4,542,025 A | 9/1985 | Tice et al. | |
| 4,585,482 A | 4/1986 | Tice et al. | |
| 4,622,244 A | 11/1986 | Lapka et al. | |
| 4,637,905 A | 1/1987 | Gardner | |
| 4,675,189 A | 6/1987 | Kent et al. | |
| 4,798,786 A | 1/1989 | Tice et al. | |
| 4,835,139 A | 5/1989 | Tice et al. | |
| 4,863,735 A | 9/1989 | Kohn et al. | |
| 4,897,268 A | 1/1990 | Tice et al. | |
| 4,938,763 A | 7/1990 | Dunn et al. | |
| 4,941,880 A | 7/1990 | Burns | |
| 5,000,886 A | 3/1991 | Lawter et al. | |
| 5,019,096 A | 5/1991 | Fox, Jr. et al. | |
| 5,059,187 A | 10/1991 | Sperry et al. | |
| 5,064,413 A | 11/1991 | McKinnon et al. | |
| 5,075,109 A | 12/1991 | Tice et al. | |
| 5,102,872 A | 4/1992 | Singh et al. | |
| 5,129,825 A | 7/1992 | Discko, Jr. | |
| 5,133,701 A | 7/1992 | Han | |
| 5,236,355 A | 8/1993 | Brizzolara et al. | |
| 5,278,202 A | 1/1994 | Dunn et al. | |
| 5,290,494 A | 3/1994 | Coombes et al. | |
| 5,360,610 A | 11/1994 | Tice et al. | |
| 5,384,133 A | 1/1995 | Boyes et al. | |
| 5,407,609 A | 4/1995 | Tice et al. | |
| 5,417,986 A * | 5/1995 | Reid et al. | 424/499 |
| 5,429,822 A | 7/1995 | Gresser et al. | |
| 5,500,228 A | 3/1996 | Lawter et al. | |
| 5,538,739 A | 7/1996 | Bodmer et al. | |
| 5,639,480 A | 6/1997 | Bodmer et al. | |
| 5,643,605 A | 7/1997 | Cleland et al. | |
| 5,648,096 A | 7/1997 | Gander et al. | |
| 5,650,173 A | 7/1997 | Ramstack et al. | |
| 5,688,530 A | 11/1997 | Bodmer et al. | |
| 5,693,343 A | 12/1997 | Reid et al. | |
| 5,762,965 A | 6/1998 | Burnett et al. | |
| 5,811,128 A * | 9/1998 | Tice et al. | 424/501 |
| 5,814,344 A | 9/1998 | Tice et al. | |
| 5,820,883 A | 10/1998 | Tice et al. | |
| 5,853,763 A | 12/1998 | Tice et al. | |

FOREIGN PATENT DOCUMENTS

EP 0052510 B2 10/1994
WO WO 92/19263 * 11/1992

OTHER PUBLICATIONS

Cassels, F.J., et al. J. Ind. Microbiol. 1995;15:214-226.*

(Continued)

*Primary Examiner*—G. R Ewoldt
(74) *Attorney, Agent, or Firm*—Elizabeth Arwine

(57) ABSTRACT

This invention is directed to oral-intestinal vaccines and their use against diseases caused by enteropathogenic organisms using antigens encapsulated within biodegradable-biocompatible microspheres.

6 Claims, 43 Drawing Sheets

OTHER PUBLICATIONS

Cassels, F.J., et al. Infec. Immun. Jun. 1992;60(6):2174-2181.*

Evans, D. G. et al., Infect. lmmun. 25:738-748, "Purification and characterization of the CFA/I antigen of enterotoxic *Esherichia coli*", Aug. 1979.*

Hall, R. H. et al., J. Bacteriol. 171:6372-74, "Purification and analysis of colonization factor antigen I, coli surace antigen I and coli surfac antigen 3 fimbriae from enterotoxigenic *Escherichia coli*", Nov. 1989.*

Karjalainen, T. K. et al., Infect. Immun. 57:1126-1130, "Molecular cloning of nucleotide sequence of the colonization factor antigen I gene of *Escherichia coli*", Apr. 1989.*

Edelman, et al., Immunization of rabbits with enterotoxigenic *E. coli* colonization factor antigen (CFA/I) encapsulated in biodegradable microspheres of poly (lactide-co-glycolide), Vaccine, vol. 11, Issue 2, p. 155-158, (1993).

Gilding, Biodegradable polymers for use in surgery-polyglycolic/ poly (ac c acid) homo- and copolymers: 1, Polymer, vol. 20, Dec. 1979, pp. 1459-1464.

Biotechnology News, Aug. 22, 1997, vol. 17, No. 20, Topical DNA vaccine elicits immune response.

Hall, et al., Purification and Analysis of Colonization Factor Antigen I, Coli Surface Antigen 1, and Coli Surface ANtigen 3 Fimbriae from Enterotoxigenic *Escherichia coli*, Journal of Bacteriology, Nov. 1989, p. 6372-6374, vol. 171, No. 11.

Evans, et al. Purification and Characterization of the CFR/I Antigen of Enterotoxigenic *Escherichia coli*, Infection and Immunity, Aug. 1979, p. 738-748, vol. 25.

Karjalainen, et al., Molecular Cloning and Nucleotide Sequence of the Colonization Factor Antigen I Gene of *Escherichia coli*, Infection and Immunity, Apr. 1989, p. 1126-1130, vol. 57.

Jeyanthi, et al., Novel, Burst Free Programmable Biodegradable Microspheres for Controlled Release of Polypeptides, Proceedings Int. Symp. control Release Bioact. Mater. (1996) p. 351-352/.

Yeh, A novel emulsification-solvent extraction technique for production of protein loaded biodegradable microparticles for vaccine and drug delivery, Journal of Controlled Release, 33 (1005) 437-445.

Yan, Characterization and morphological analysis of protein-loaded poly(lactide-co-glycolide) microparticles prepared by watewr-in-oil-in-water emulsion technique, Journal of Controlled Release, 32 (1994) 231-241.

Wang, et al., Influence of formulation methods on the in vitro controlled release of protein from poly (ester) microspheres Journal of Controlled Release, 17 (1991) 23-32.

Brown, Wonder Drugs' Losing Healing Aura, The Washing Post, Jun. 26, 1995, A section.

Setterstrom, Controlled Release of Antibiotics From biodegradable Microcapsules For Wound Infection Control, Chemical Abstracts, 1983, pp. 215-226.

Perez-Casal, et al., Gene Encoding the Major Subunit of CS1 Pill of Human Enterotoxigenic *Escherichia coli*, Infection and Immunity, Nov. 1990, p. 3594-3600, vol. 58, No. 11.

Jordi, et al., Analysis of the first two genes of the CS1 fimbrial operon in human enterotoxigenic *Escherichia coli* of serotype 0139: H28, FEMS Microbiology Letters 80, (1991) p. 265-270.

Tan, et al., Mapping the Antigenic Epitopes of Human Dihydrofolate Reductase by Systematic Synthesis of Peptides on solid Supports, The Journal of Biological Chemistry, vol. 265, No. 14, Issue of May 15, pp. 8022-8026 (1990).

McConnel, et al., Antigenic homology within human enterotoxigenic *Esherichia coli* fimbrial colonization factor antigens: CFA/I, coli-surface-associated antigens (CS)1, CS2, CS4 and CS17, FEMS Microbiology Letters 61 (1989) 105-108.

Van der Zee, Efficient mapping and characterization of a T cell epitope by the simultaneous synthesis of multiple peptides, Eur. J. Immunol. 1989, 19: 43-47.

Cassels, et al., Analysis of *Escherichia coli* Colonization Factor Antigen I Linear B-Cell Epitopes, as Determined by Primate Responses, following Protein Sequence Verification, Infection and Immunity, Jun. 1992, p. 2174-2181, vol. 60, No. 6.

Romagnoli, et al. Peptide-MHC Interaction: A Rational Approach to Vaccine Design, Inter, RE. Immunol. 6, 1990, 00 61-73.

Maister, First Oral AIDS Vaccine Trials Near, BioWorld Today, Tuesday, Apr. 19, 1994, p. 4.

Rognan, et al., Molecular Modeling of an Antigenic Complex Between a Viral Peptide and a Class I Major Histocompatibility Glycoprotein, Proteins Structure, Function and Genetics 13 70-85 (1992).

Brown, A hypothetical model of the foreign antigen biinding site of Class II histocompatibility molecules, Nature, vol. 332, Apr. 28, 1988, p. 845-850.

* cited by examiner

Fig. 10b

SEQ ID NO: 35 Lane 2  LADTPQLTDVLNSTVQMP  (62-79)
SEQ ID NO: 36 Lane 3  SYRVMTQVHTNDATKKVIV  (42-60)

SEQ ID NO: 37  2%2   VEKNITVTASVDPVIDLLQADGNALPSAVKLAYSPASKTFESYRVMTQVH 50
SEQ ID NO: 38  184D  VEKNITVTASVDPVIDLLQADGNALPSAVKLAYSPASKTFESYRVMTQVH
SEQ ID NO: 39  34    VEKNITVTASVDPVIDLLQADGNALPSAVKLAYSPASKTFESYRVMTQVH

2%2   TNDATKKVIVKLADTPQLTDVNSTVQMPISVSWGGQVLSTTAKEFEAAA 100
184D  TNDATKKVIVKLADTPQLTDVNSTVQMPISVSWGGQVLSTTAKEFEAAA
34    TNDATKKVIVKLADTPQLTDVNSTVQMPISVSWGGQVLSTTAKEFEAAA

2%2   LGYSASGVNGVSSQELVISAAPKTAGTAPTAGNYSGVVSLVMTLGS 147
184D  LGYSASGVNGVSSQELVISAAPKTAGTAPTAGNYSGVVSLVMTLGS
34    LGYSASGVNGVSSQELVISAAPKTAGTAPTAGNYSGVVSLVMTLGS

Fig. 18

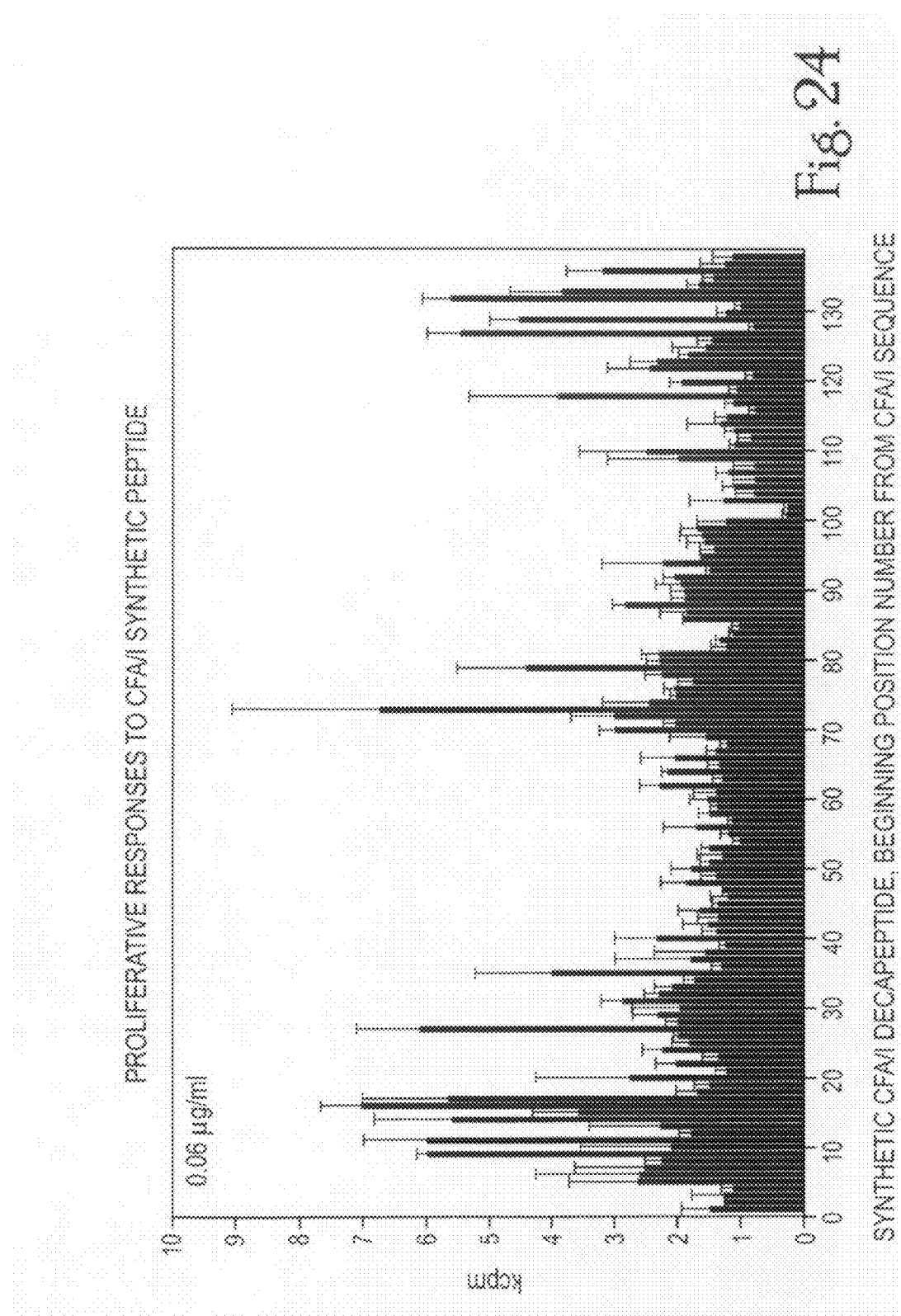

ORAL-INTESTINAL VACCINES AGAINST DISEASES CAUSED BY ENTEROPATHIC ORGANISMS USING ANTIGENS ENCAPSULATED WITHIN BIODEGRADABLE-BIOCOMPATIBLE MICROSPHERES

II. CROSS REFERENCE

This application is a continuation of Ser. No. 08/396,986 filed Mar. 1, 1995 (abandoned), which is a continuation of Ser. No. 08/191,374 filed Apr. 6, 1994, (abandoned), which is a continuation of Ser. No. 07/690,485 filed Apr. 24, 1991 (abandoned), which is a continuation in part of 07/521,945 filed May 11, 1990 (abandoned), which is a continuation in part of 06/590,308 filed Mar. 16, 1984 (abandoned).

I. GOVERNMENT INTEREST

The invention described herein may be manufactured, licensed and used by or for governmental purposes without the payment of any royalties to us thereon.

III. FIELD OF THE INVENTION

This invention relates to oral-intestinal vaccines against diseases caused by enteropathogenic organisms using antigens encapsulated within biodegradable-biocompatible microspheres (matrix).

IV. BACKGROUND OF THE INVENTION

Most infectious agents have their first contact with the host at a mucosal surface; therefore, mucosal protective immune mechanisms are of primary importance in preventing these agents from colonizing or penetrating the mucosal surface. Numerous studies have demonstrated that a protective mucosal immune response can best be initiated by introduction of the antigen at the mucosal surface, and parenteral immunization is not an effective method to induce mucosal immunity. Antigen taken up by the gut-associated lymphoid tissue (GALT), primarily by the Peyer's patches in mice, stimulates T helper cell ($T_H$) to assist in IgA B cell responses or stimulates T suppressor cells ($T_S$) to mediate the unresponsiveness of oral tolerance. Particulate antigen appears to shift the response towards the ($T_H$) whereas soluble antigens favor a response by the ($T_S$). Although studies have demonstrated that oral immunization does induce an intestinal mucosal immune response, large doses of antigen are usually required to achieve sufficient local concentrations in the Peyer's patches. Unprotected protein antigens may be degraded or may complex with secretory IgA in the intestinal lumen.

One possible approach to overcoming these problems is to homogeneously disperse the antigen of interest within the polymeric matrix of appropriately sized biodegradable, biocompatible microspheres that are specifically taken up by GALT. Eldridge et. al. have used a murine model to show that orally-administered 1-10 micrometer microspheres consisting of polymerized lactide and glycolide, (the same materials used in resorbable sutures), were readily taken up into Peyer's patches, and the 1-5 micrometer size were rapidly phagocytized by macrophages. Microspheres that were 5-10 micrometers (microns) remained in the Peyer's patch for up to 35 days, whereas those less than 5 micrometer disseminated to the mesenteric lymph node (MLN) and spleen within migrating MAC-1[+] cells. Moreover, the levels of specific serum and secretory antibody to staphylococcal enterotoxin B toxoid and inactivated influenza A virus were enhanced and remained elevated longer in animals which were immunized orally with microencapsulated antigen as compared to animals which received equal doses of non-encapsulated antigen. These data indicate that microencapsulation of an antigen given orally may enhance the mucosal immune response against enteric pathogens. AF/R1 pili mediate the species-specific binding of *E. coli* RDEC-1 with mucosal glycoproteins in the small intestine of rabbits and are therefore an important virulence factor. Although AF/R1 pili are not essential for *E. coli* RDEC-1 to produce enteropathogenic disease, expression of AF/R1 promotes a more severe disease. Anti-AF/R1 antibodies have been shown to inhibit the attachment of RDEC-1 to the intestinal mucosa and prevent RDEC-1 disease in rabbits. The amino acid sequence of the AF/R1 pilin subunit has recently been determined, but specific antigenic determinants within AF/R1 have not been identified.

Recent advances in the understanding of B cell and T cell epitopes have improved the ability to select probably linear epitopes from the amino acid sequence using theoretical criteria. B cell epitopes are often composed of a string of hydrophilic amino acids with a high flexibility index and a high probability of turns within the peptide structure. Prediction of T cell epitopes are based on the Rothbard method which identifies common sequence patterns that are common to known T cell epitopes or the method of Berzofsky and others which uses a correlation between algorithms predicting amphipathic helices and T cell epitopes.

In the current study we have used these theoretical criteria to predict probable T or B cell epitopes from the amino acid sequence of AF/R1. Four different 16 amino acid peptides that include the predicted epitopes have been synthesized: AF/R1 40-55 as a B cell epitope, 79-94 as a T cell epitope, 108-123 as a T and B cell epitope, and AF/R1 40-47/79-86 as a hybrid of the first eight amino acids from the predicted B cell epitope and the T cell epitope. We have used these peptides as well as the native protein to stimulate the in vitro proliferation of lymphocytes taken from the Peyer's patch, MLN, and spleen of rabbits which have received intraduodenal priming with microencapsulated or non-encapsulated AF/R1. Our results demonstrate the microencapsulation of AF/R1 potentiates the cellular immune response at the level of the Peyer's patch, thus enhancing in vitro lymphocyte proliferation to both the native protein and its linear peptide antigens. CFA/I pili, rigid thread-like structures which are composed of repeating pilin subunits of 147 amino acid found on serogroups 015, 025, 078, and 0128 of enterotoxigenic *E. coli* (ETEC) [1-4, 18]. CFA/I promotes mannose resistant attachment to human brush borders [5]; therefore, a vaccine that established immunity against this protein may prevent the attachment to host tissues and subsequent disease. In addition, because the CFA/I subunit shares N-terminal amino acid sequence homology with CS1, CFA/II (CS2) and CFA/IV (CS4) [4], a subunit vaccine which contained epitopes from this area of the molecule may protect against infection with various ETEC.

Until recently, experiments to identify these epitopes were time consuming and costly; however, technology is now available which allows one to simultaneously identify all the T cell and B cell epitopes in the protein of interest. Multiple Peptide synthesis (Pepscan) is a technique for the simultaneous synthesis of hundreds of peptides on polyethylene rods [6]. We have used this method to synthesize all the 140 possible overlapping actapeptides of the CFA/I protein. The peptides, still on the rods, can be used directly in ELISA assays to map B call epitopes [6, 12-14]. We have also synthesized all the 138 possible overlapping decapeptides of the CFA/I protein. For analysis of T cell epitopes, these peptides can be cleaved from the rods and used in proliferation assays [15]. Thus this technology allows efficient mapping and localization of both B cell and T cell epitopes to a resolution of a single amino acid [16]. These studies were designed to identify antigenic epitopes of ETEC which may be employed in the construction of an effective subunit vaccine.

CFA/I pili consist of repeating pilin protein subunits found on several serogroups of enterotoxigenic *E. coli* (ETEC) which promote attachment to human intestinal mucosa. We wished to identify areas within the CFA/I molecule that contain immunodominant T cell epitopes that are capable of stimulating the cell-mediated portion of the immune response in primates as well as immunodominant B cell epitopes. To do this, we (a) resolved the discrepancy in the literature on the complete amino acid sequence of CFA/I, (b) immunized three Rhesus monkeys with multiple i.m. injections of purified CFA/I subunit in Freund's adjuvant, (c) synthesized 138 overlapping decapeptides which represented the entire CFA/I protein using the Pepscan technique (Cambridge Research Biochemicals), (d) tested each of the peptides for their ability to stimulate the spleen cells from the immunized monkeys in a proliferative assay (e) synthesized 140 overlapping octapeptides which represented the entire CFA/I protein, and (f) tested serum from each monkey for its ability to recognize the octapeptides in a modified ELISA assay. A total of 39 different CFA/I decapeptides supported a significant proliferative response with the majority of the responses occurring within distinct regions of the protein (peptides beginning with residues 8-40, 70-80, and 127-137). Nineteen of the responsive peptides contained a serine residue at positions 2, 3, or 4 in the peptide, and a nine contained a serine specifically at position 3. Most were predicted to be configured as an alpha holix and have a high amphipathic index. Eight B cell epitopes were identified at positions 3-11, 11-21, 22-29, 32-40, 38-45, 66-74, 93-101, and 124-136. The epitope at position 11-21 was strongly recognized by all three individual monkeys, while the epitopes at 93-101, 124-136, 66-74, and 22-29 were recognized by two of the three monkeys.

V. SUMMARY OF THE INVENTION

This invention relates to a novel pharmaceutical composition, a microcapsule/sphere formulation, which comprises an antigen encapsulated within a biodegradable polymeric matrix such as poly (DL-lactide-co-glycolide) (DL-PLG), wherein the relative ratio between the lactide and glycolide component of the DL-PLG is within the range of 40:60 to 0:100, and its use, as a vaccine, in the effective pretreatment of animals (including humans) to prevent intestinal infections caused by a virus or bacteria. In the practice of this invention, applicants found that the AF/R1 adherence factor is a plasmid encoded pilus composed of repeating pilin protein subunits that allows *E. coli* RDEC-1 to attach to rabbit intestinal brush borders. To identify an approach that enhances the immunogenicity of antigens that contact the intestinal mucosa, applicants investigated the effect of homogeneously dispersing AF/R1 pili within biodegradable microspheres that included a size range selected for Peyer's Patch localization. New Zealand White rabbits were primed twice with 50 micrograms of either microencapsulated or nonencapsulated AF/R1 by endoscopic intraduodenal inoculation. Lymphoid tissues were removed and cellular proliferative responses to AF/R1 and synthetic AF/R1 peptides were measured in vitro. The synthetic peptides represented possible T and/or B cell epitopes which were selected from the AF/R1 subunit sequence using theoretical criteria. In rabbits which had received nonencapsulated AF/R1, Peyer's Patch cells demonstrated slight but significant proliferation in vitro in response to AF/R1 pili but not the AF/R1 synthetic peptides. In rabbits which had received microencapsulated AF/R1, Peyer's Patch cells demonstrated a markedly enhanced response to AF/R1 and the synthetic peptides. Cells from the spleen and mesenteric lymph nodes responded similarly to AF/R1 pili in both groups of animals, while there was a greater response to the synthetic peptide AF/R1 40-55 in rabbits that had received microencapsulated AF/R1. These data demonstrate that microencapsulation of AF/R1 potentiates the mucosal cellular immune response to both the native protein and its linear peptide antigens.

VI. BRIEF DESCRIPTION OF THE DRAWINGS

FIG. 1 shows the size distribution of microspheres wherein the particle size distribution (%) is (a) By number 1-5 (91) and 6-10 (9) and (b) By weight 1-5 (28) and 6-10 (72).

FIG. 2 shows a scanning electron micrograph of microspheres.

FIGS. 3(a) and (b) show the In vitro immunization of spleen cells and demonstrates that AF/RI pilus protein remains immunogenic to rabbit spleen cells immunized in vitro after microencapsulation. AF/R1 pilus protein has been found to be immunogenic for rabbit spleen mononuclear cells in vitro producing a primary IgM antibody response specific to AF/RI. Immunization with antigen encapsulated in biodegradable, biocompatible microspheres consisting of lactide/glycolide copolymers has been shown to endow substantially enhanced immunity over immunization with the free antigen. To determine if microencapsulated-AF/RI maintains the immunogenicity of the free pilus protein, a primary in vitro immunization assay was conducted. Rabbit spleen mononuclear cells at a concentration of $3\times10^5$ cells/well. Triplicate wells of cells were immunized with free AF/RI in a dose range from 15 to 150 ng/ml or with equivalent doses of AF/RI contained in microspheres. Supernatants were harvested on days 7, 9, 12, and 14 of culture and were assayed for free AF/RI pilus protein specific IgM antibody by the ELISA. Supernatant control values were subtracted from those of the immunized cells. Cells immunized with free pilus protein showed a significant positive IgM response on all four days of harvest, with the antibody response increasing on day 9, decreasing on day 12, and increasing again on day 14. Cells immunized with microencapsulated pilus protein showed a comparable positive IgM antibody response as cells immunized with free pilus protein. In conclusion, AF/RI maintains immunogenicity to rabbit spleen cells immunized in vitro after microencapsulation.

FIGS. 4(a) and (b) show in vitro immunization of Peyer's patch cells. Here the AF/RI pilus protein remains immunogenic to rabbit Peyer's patch cells immunized in vitro after microencapsulation. AF/RI pilus protein has been found to be immunogenic for rabbit Peyer's patch mononuclear cells in vitro producing a primary IgM antibody response specific to AF/RI. Immunization with antigen encapsulated in biodegradable, biocompatible microspheres consisting of lactide/glycolide copolymers has been shown to endow substantially enhanced immunity over immunization with the free antigen. To determine if microencapsulated AF/RI maintains the immunogencity of the free pilus protein, a primary in vitro immunization assay was conducted. Rabbit Peyer's patch mononuclear cells at a concentration of $3\times10^6$ cells/ml were cultured in 96-well, round bottom microculture plates at a final concentration of $6\times10^5$ cells/well. Triplicate wells of cells were immunized with free AF/RI in a dose range from 15 to 150 ng/ml or with equivalent dose of AF/RI contained in microspheres. Supernatants were harvested on days 7, 9, 12, and 14 of culture and were assayed for free AF/RI pilus protein specific IgM antibody by the ELISA. Supernatant control values were subtracted from those of the immunized cells. Cells immunized with free pilus protein showed a significant positive IgM response on all four days of harvest, with the highest antibody response on day 12 with the highest antigen dose. Cells immunized with encapsulated pilus protein showed a positive response on day 12 with all three antigen doses. In conclusion, AF/RI pilus protein maintains immunogenicity to rabbit Peyer's patch cells immunized in vitro after microencapsulation.

FIG. 5 shows proliferative responses to AF/RI by rabbit Peyer's patch cells. Naive rabbits were primed twice with 50 micrograms of either non-encapsulated (rabbits 132 and 133) or microencapsulated (rabbits 134 and 135) AF/RI pili by endoscopic intraduodenal inoculation seven days apart. Seven days following the second priming, Peyer's patch cells were cultured with AF/RI in 96-well plates for four days followed by a terminal six hour pulse with [$^3$H]thymidine. Data shown is the SI calculated from the mean cpm of quadruplicate cultures. Responses were significant for all rabbits: 132 ($p=0.013$), 133 ($p=0.0006$), 134 ($p=0.0016$), and 135 ($p=0.0026$). Responses were significantly different between the two groups. Comparison of the best responder in the nonencapsulated antigen group (rabbit 133) with the lowest responder in the microencapsulated antigen group (rabbit 134) demonstrated an enhanced response when the immunizing antigen was microencapsulated ($p=0.0034$).

Additionally, FIG. 5 relates to the in vitro lymphocyte proliferation after sensitization of rabbit lymphoid tissues with encapsulated or non-encapsulated AF/RI pilus adhesion of *E. coli* strain RDEC-1. The AF/RI adherence factor is a plasmid encoded pilus protein that allows RDEC-1 to attach to rabbit intestinal brush borders. We investigated the immunopotentiating effect of encapsulating purified AF/RI into biodegradable non-reactive microspheres composed of polymerized lactide and glycolide, materials used in resorbable sutures. The microspheres had a size range of 5-10 microns, a size selected for Peyer's Patch localization, and contained 0.62% protein by weight. NZW rabbits were immunized twice with 50 micrograms of either encapsulated or non-encapsulated AF/RI by intraduodenal later of non-encapsulated AF/RI by intraduodenal inoculation seven days apart. Lymphocyte proliferation in response to purified AR/RI was conducted in vitro at seven days and showed that encapsulating the antigen into microspheres enhanced the cellular immune response in the Peyer's Patch; however, no significant increase was observed in spleen or mesenteric lymph node. These data suggest that encapsulation of AF/RI may potentiate the mucosal cellular immune response.

FIG. 6 *a-d* show proliferative responses to AF/RI synthetic peptides by rabbit Peyer's patch cells. Naive rabbits were primed twice with 50 micrograms of either non-encapsulated (rabbits 132 and 133) or microencapsulated (rabbits 134 and 135) AF/RI pili by endoscopic intraduodenal inoculation seven days apart. Seven days following the second priming, Peyer's patch cells from each rabbit were cultured with AF/R1 40-55 (FIG. 6*a*), AF/R1 79-94 (FIG. 6*b*), AF/R1 108-123 (FIG. 6*c*), or AF/R1 40-47/79-86 (FIG. 6*d*) in 96-well plates for four days followed by a terminal six hour pulse with [$^3$H]thymidine. Data shown is the SI calculated from the mean cpm of quadruplicate cultures. The responses of rabbits 132 and 133 were not significant to any of the peptides tested. Rabbit 134 had a significant response to (a) AF/R1 40-55 ($p=0.0001$), (b) AF/R1 79-94 ($p=0.0280$), and (d) AF/R1 40-57/79-86 ($p=0.025$), but not to (c) AF/R1 108-123. Rabbit 135 had a significant response to (a) AF/R1 40-55 ($p=0.034$), (b) AF/R1 79-94 ($p=0.040$), and (c) AF/R1 108-123 ($p<0.0001$), but not to (d) AF/R1 40-47/79-86. This demonstrates enhanced proliferative response to peptide antigens following mucosal priming with microencapsulated pili. AF/RI pili promotes RDEC-1 attachment to rabbit intestinal brush borders. Three 16 amino acid peptides were selected by theoretical criteria from the AF/RI sequence as probable T or B cell epitopes and were synthesized: AF/R1 40-55 as a B cell epitope, 79-94 as a T cell epitope, and 108-123 as a T and B cell epitope. We used these peptides to investigate a possible immunopotentiating effect of encapsulating purified AF/RI pili into biodegradable, biocompatible microspheres composed of polymerized lactide and glycolide at a size range that promotes localization in the Peyer's Patch (5-10 micrometers). NZW rabbits were primed twice with 50 micrograms AF/RI by endoscopic intraduadenal inoculation and their Peyer's Patch cells were cultured in vitro with the AF/RI peptides. In two rabbits which had received encapsulated AF/RI, lymphocyte proliferation was observed to AF/RI 40-55 and 79-94 in both rabbits and to 108-123 in one of two rabbits. No responses to any of the peptides were observed in rabbits which received non-encapsulated AF/RI. These data suggest that encapsulation of AF/RI may enhance the cellular response to peptide antigens.

FIGS. 7*a-d* show B-cell responses of Peyer's patch cells to AF/R1 and peptides.

FIGS. 8*a-d* show B-cell responses of Peyer's Patch cells to AF/RI and peptides.

FIGS. 9*a-d* show B-cell responses of spleen cells to AF/R1 and Peptides.

FIGS. 10*a-d* show B cell responses of spleen cells to AF/R1 and peptides.

FIGS. 7 through 10, illustrate enhanced lymphocyte antibody response by mucosal immunization of rabbits with microencapsulated AF/R1 pilus protein. The AF/RI pilus protein has been found to be immunogenic for rabbit spleen and Peyer's patch cells in vitro producing a primary IgM antibody response. The purpose of this study was to determine if AR/R1 pilus protein immune response is enhanced by microencapsulation. The AF/R1 was incorporated into biodegradable, biocompatible microspheres composed of lactide-glycolide copolymers, had a size range of 5-10 micrometer and containing 0.62% pilus protein by weight. Initially, NZW rabbits were immunized twice with 50 micrograms of either encapsulated or non-encapsulated AF/RI via intraduodenal route seven days apart. For in vitro challenge, $6\times10^5$ rabbit lymphocytes, were set in microculture at final volume of 0.2 ml. Cells were challenged with AR/RI or three different synthetic 16 amino acid peptides representing, either predicted T, B or T and B cell epitopes in a dose range of 15 to 150 ng/ml for splenic cells or 0.05 to 5.0 micrograms/ml for Peyer's patch mononuclear cells (in triplicate). Supernatants were collected on culture days 3, 5, 7, and 9 assayed by ELISA for anti-AF/R1 antibody response as compared to cell supernatant control. Significant antibody responses were seen only from spleen and Peyer's patch cells from rabbits immunized with microencapsulated AF/R1. The antibody response tended to peak between days 5 and 9 was mainly an IgM response. The results for the predicted epitopes were similar to those obtained with purified AF/RI. In conclusion, intestinal immunization with AF/RI pilus protein contained within microspheres greatly enhances both the spleen and Peyer's patch B-cell responses to predicted T & B-cell epitopes.

FIG. 11 shows proliferative responses to AF/R1 40-55 by rabbit MLN cells. Naive rabbits were primed twice with 50 micrograms of either nonencapsulated (rabbits 132 and 133) or microencapsulated (rabbits 134 and 135) AF/R1 pili by endoscopic intraduodenal inoculation seven days apart. Seven days following the second priming, MLN cells were cultured with AF/R1 40-55 for four days in 24-well plates. Cultures were transferred into 96-well plates for a terminal [$^3$H]thymidine pulse. Data shown is the SI calculated from the mean cpm of quadruplicate cultures. Responses of rabbits 132 and 133 were not statistically significant. Responses were significant for rabbits 134 (p=0.0.0051) and 135 (p=0.0055).

FIG. 12 shows proliferative responses to AF/R1 40-55 by rabbit spleen cells. Naive rabbits were primed twice with 50 micrograms of either nonencapsulated (rabbits 132 and 133) or microencapsulated (rabbits 134 and 135) AF/R1 pili by endoscopic intraduodenal inoculation seven days apart. Seven days following the second priming, spleen cells were cultured with AF/R1 40-55 for four days in 24-well plates. Cultures were transferred into 96 well plates for a terminal [$^3$H]thymidine pulse. Data shown is the SI calculated from the mean cpm of quadruplicate cultures. Responses of rabbits 132 and 133 were not statistically significant. Responses were significant for rabbits 134 (p=0.0.0005) and 135 (p=0.0066).

Figures 16A, 16B:
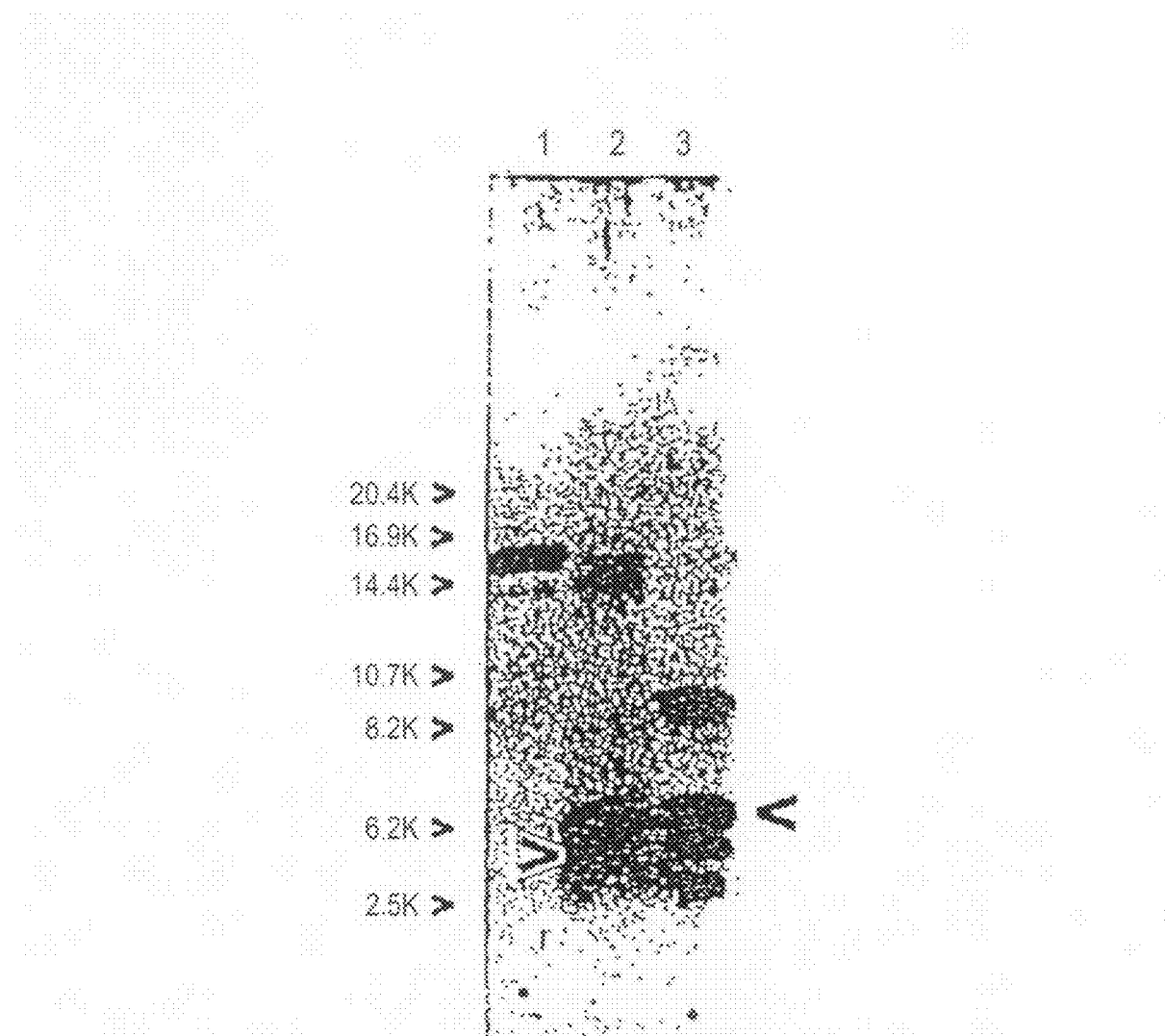

FIG. 16. A. SDS-PAGE of intact CFA/I (lane 1), trypsin treated CPA/I (lane 2), and *S. aureus* V8 protease treated CFA/I. Molecular masses of individual bands were estimated from molecular weight standards (on left). Multiple lanes of both trypsin and V8 treated CFA/I were transferred to PVDF membranes where bands corresponding to the approximate molecular masses of 3500 (trypsin digest, see arrow lane 2) and 6000 (V8 digest, see arrow lane 3) were excised and subjected to Edman degradation. B. Resulting sequence of protein fragments from each lane of A (position of sequenced portion of fragment in the intact protein. Underlined, italisized residues are amino acids under dispute in literature.

Figure 17A:
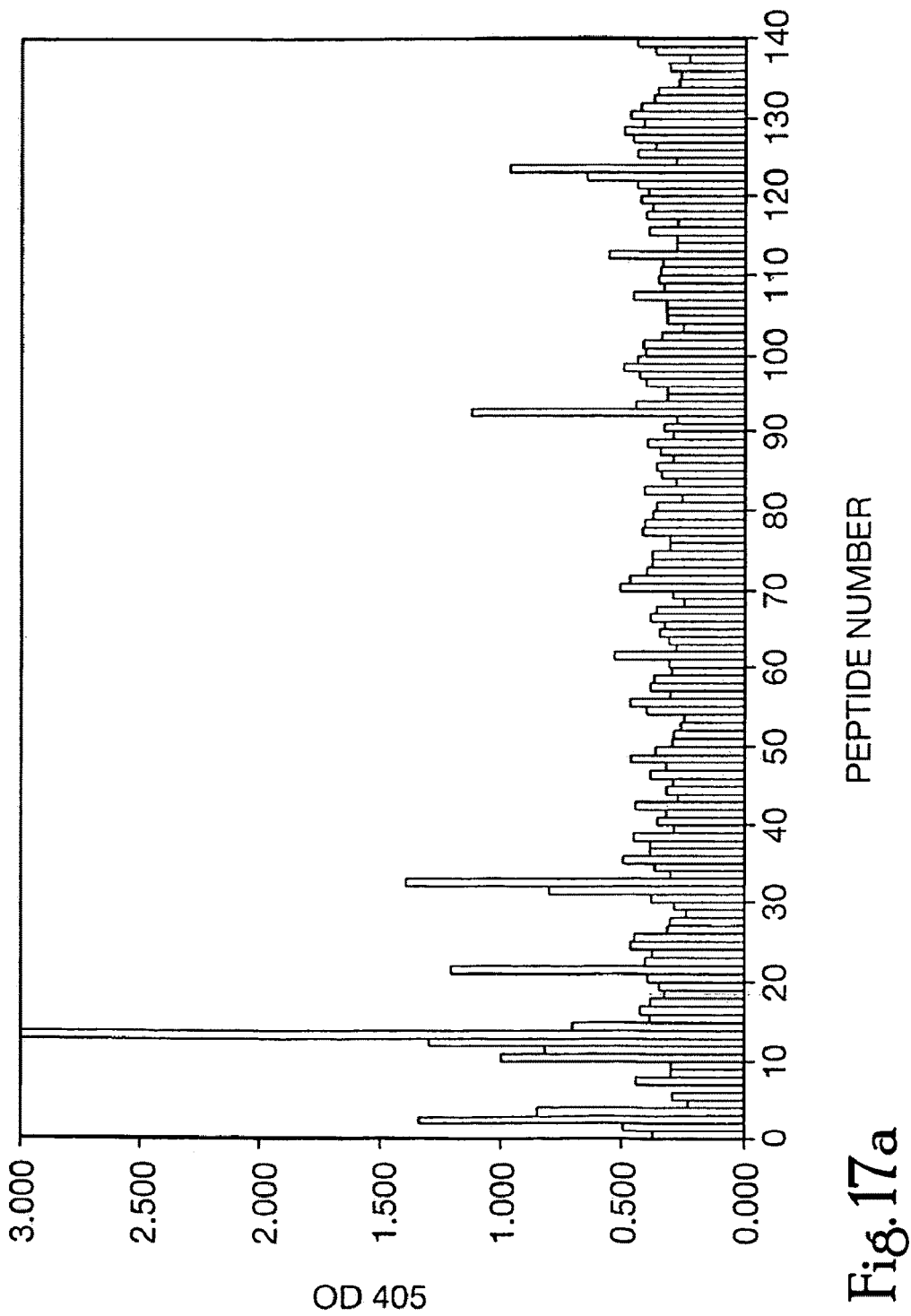
Figure 17B:
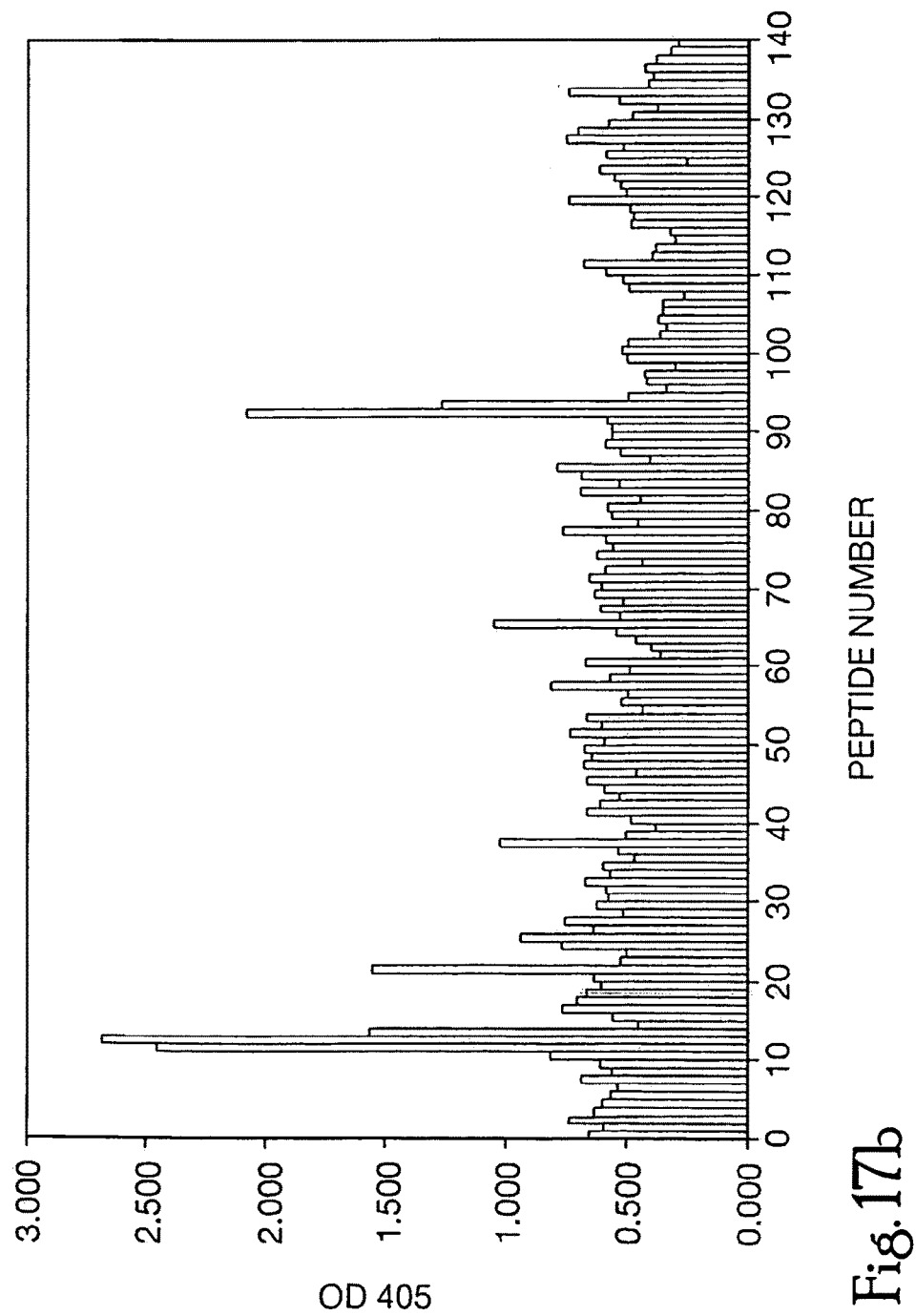
Figure 17C:
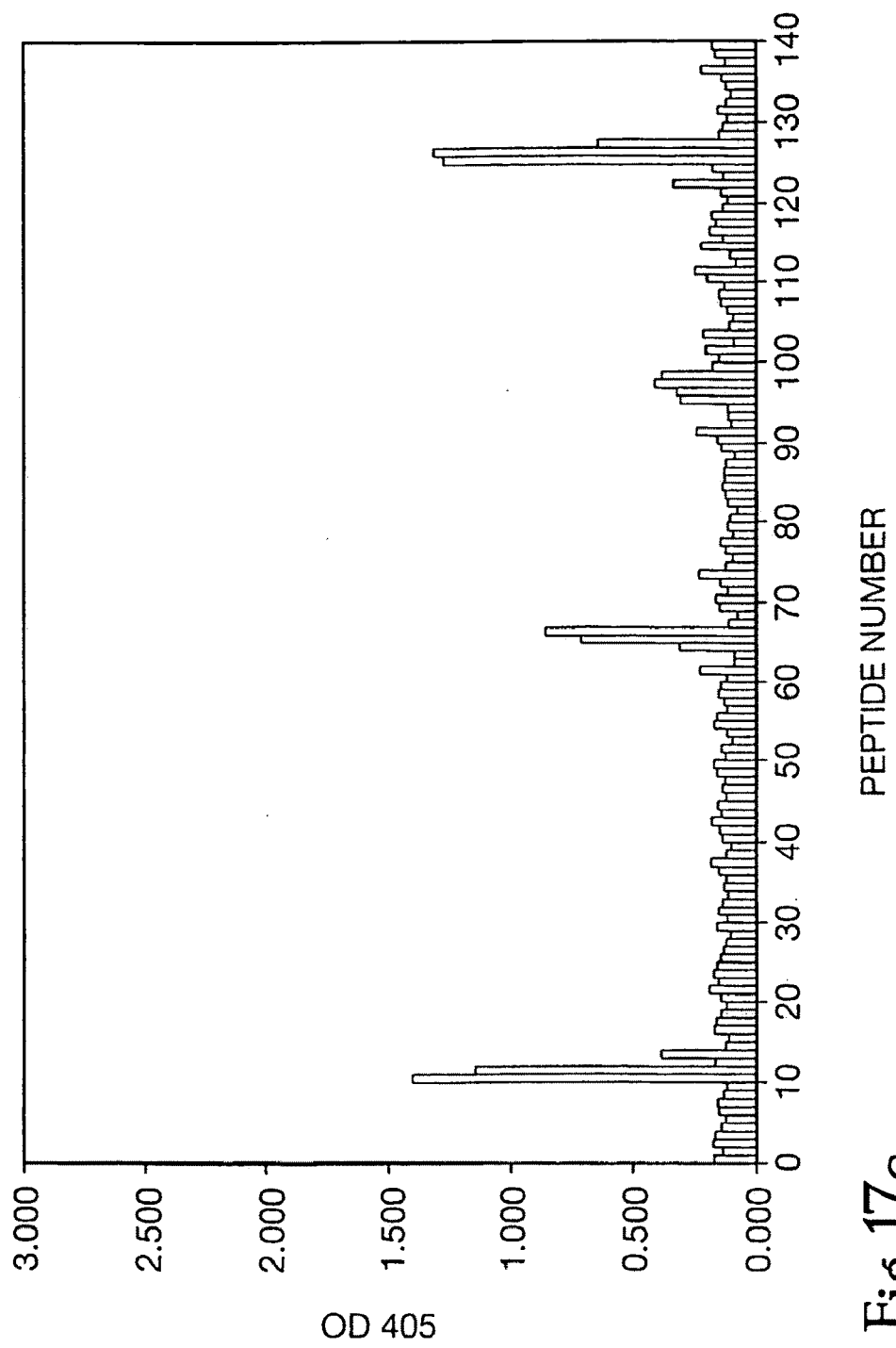

FIG. 17. ELISA assay results testing hyperimmune sera of monkeys (A)2Z2 (monkey 3), (B) 184(D) (monkey 1) and (C) 34 (monkey 2) to CFA/I primary structure immobilized on polyethylene pins. Monkey sera diluted 1:1000. Peptide number refers first amino acid in sequence of octapeptide on pin from CFA/I primary structure OD 405 refers to optical density wavelength at which ELISA plates were reat (405 nm).

FIG. 18. Complete sequence of CFA/I (147 amino acids) with B cell recognition site (boxed areas) as defined by each individual monkey response (2Z2, 184D, and 34). Derived from data in FIG. 17.

Figure 19:
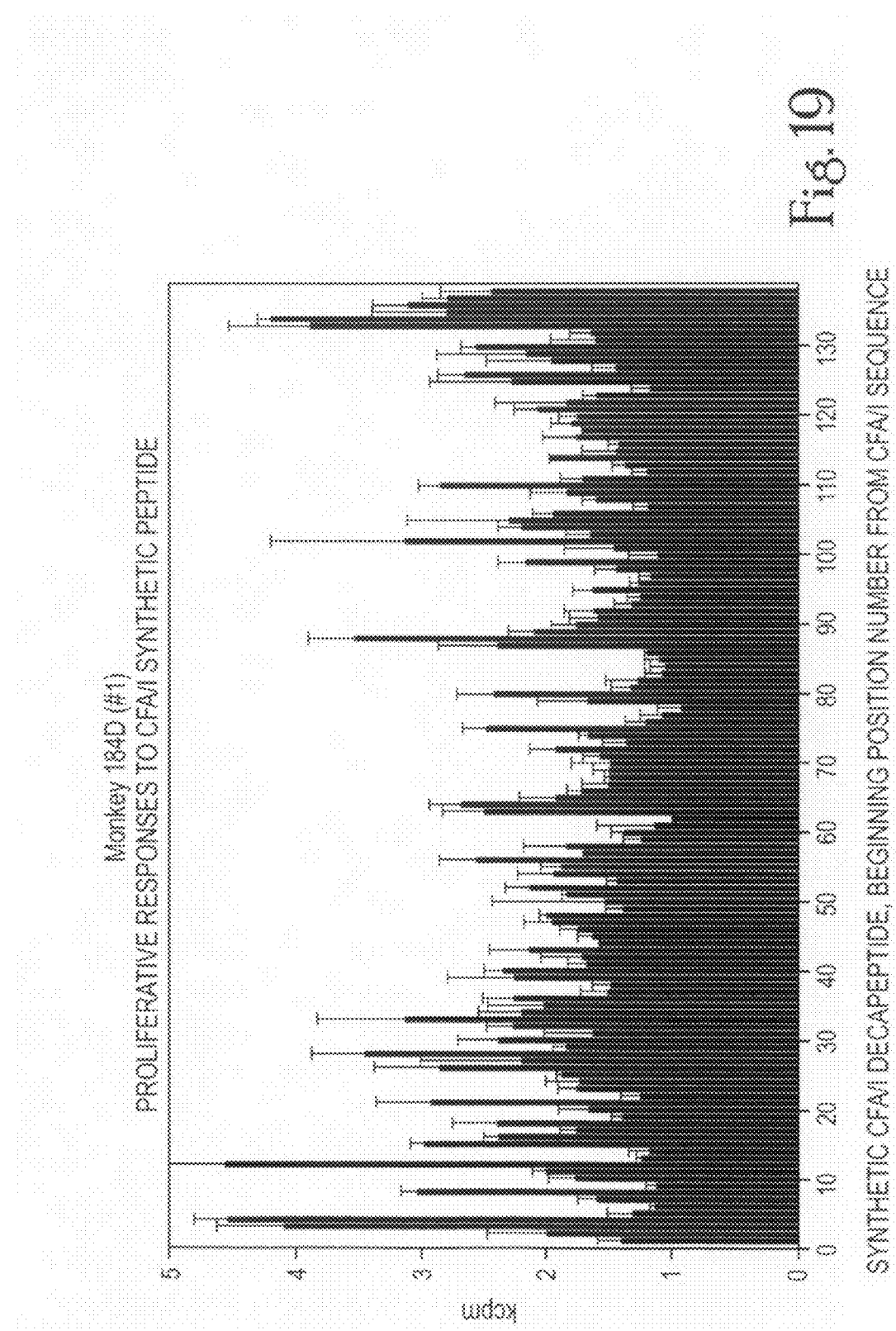
Figure 20:
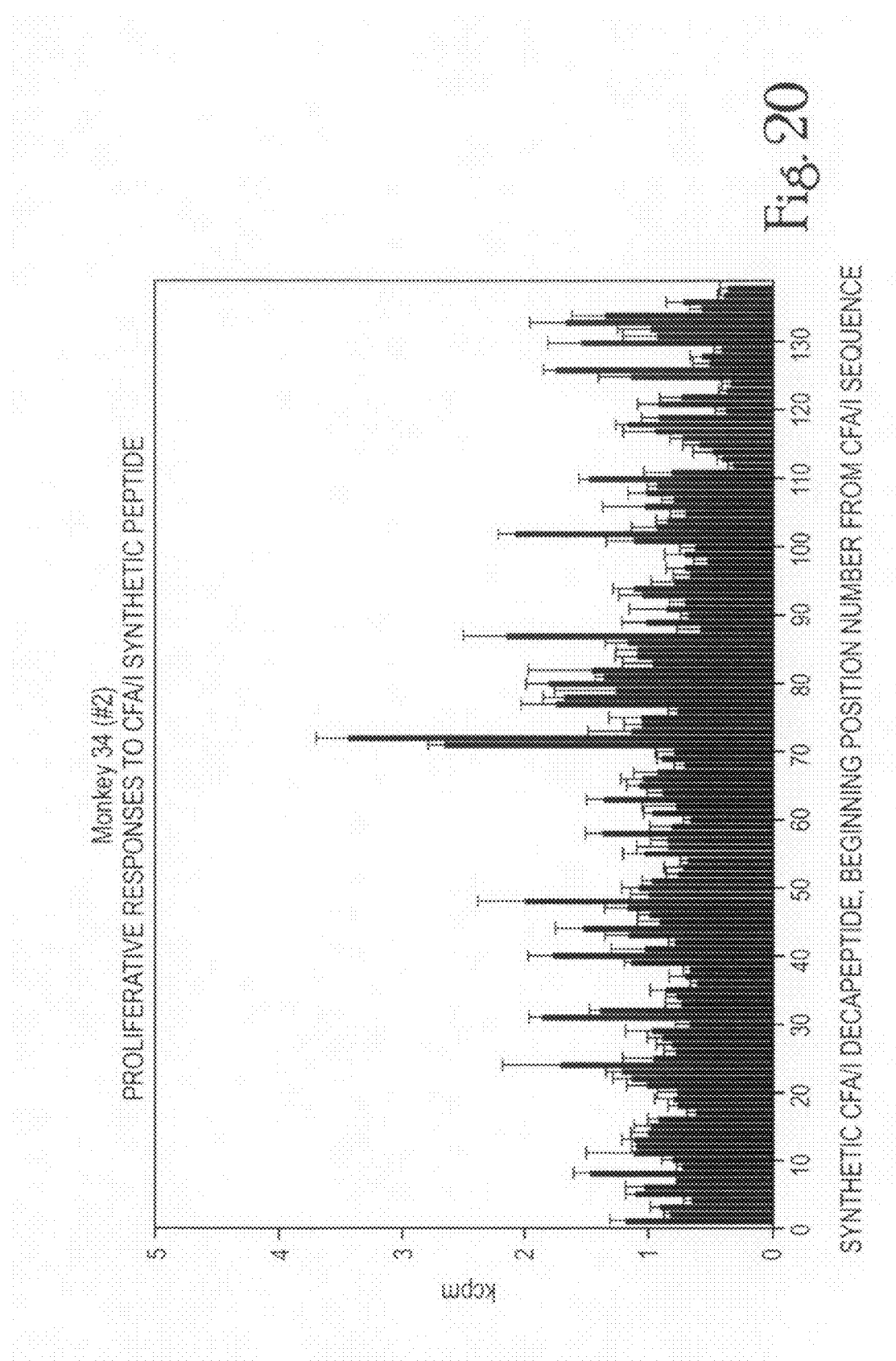
Figure 21:
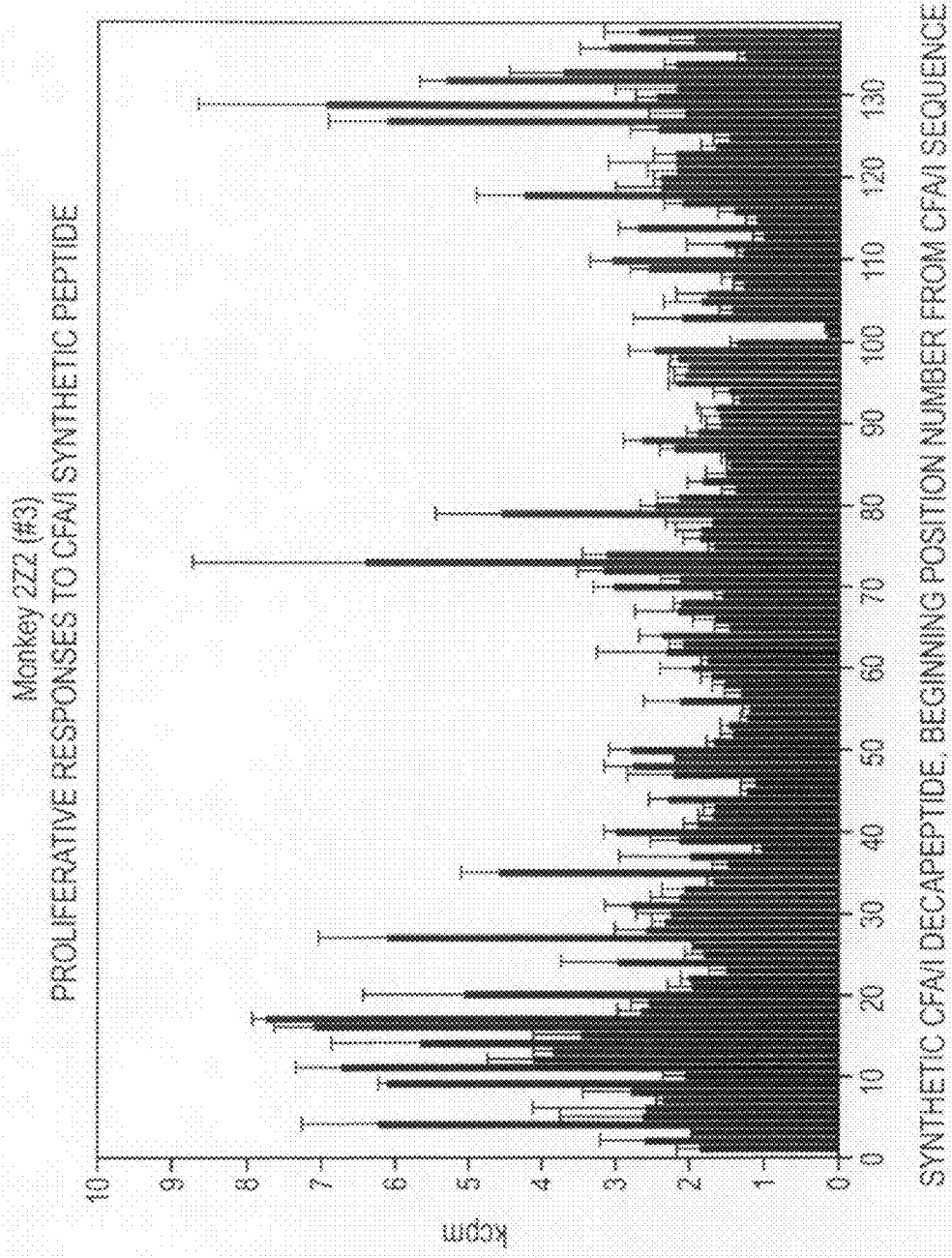

FIGS. 19-21. Lymphocyte proliferation to synthetic decapeptides of CFA/I. Each monkey was immunized with three i.m. injections of CFA/I subunits in adjuvant, and its spleen cells were cultured with synthetic decapeptides which had been constructed using the Pepscan technique. The decapeptides represented the entire CFA/I protein. Concentrations of synthetic peptide used included 6.0, 0.6, and 0.06 micrograms/ml. Values shown represent the maximum proliferative response produced by any of the three concentrations of antigen used±the standard deviation. The cpm of the control peptide for each of the three monkeys was 1,518±50, 931±28, and 1,553±33 respectively. The cpm of the media control for each of the three monkeys was 1,319±60, 325±13, and 1,951±245 respectively.

Figure 22:
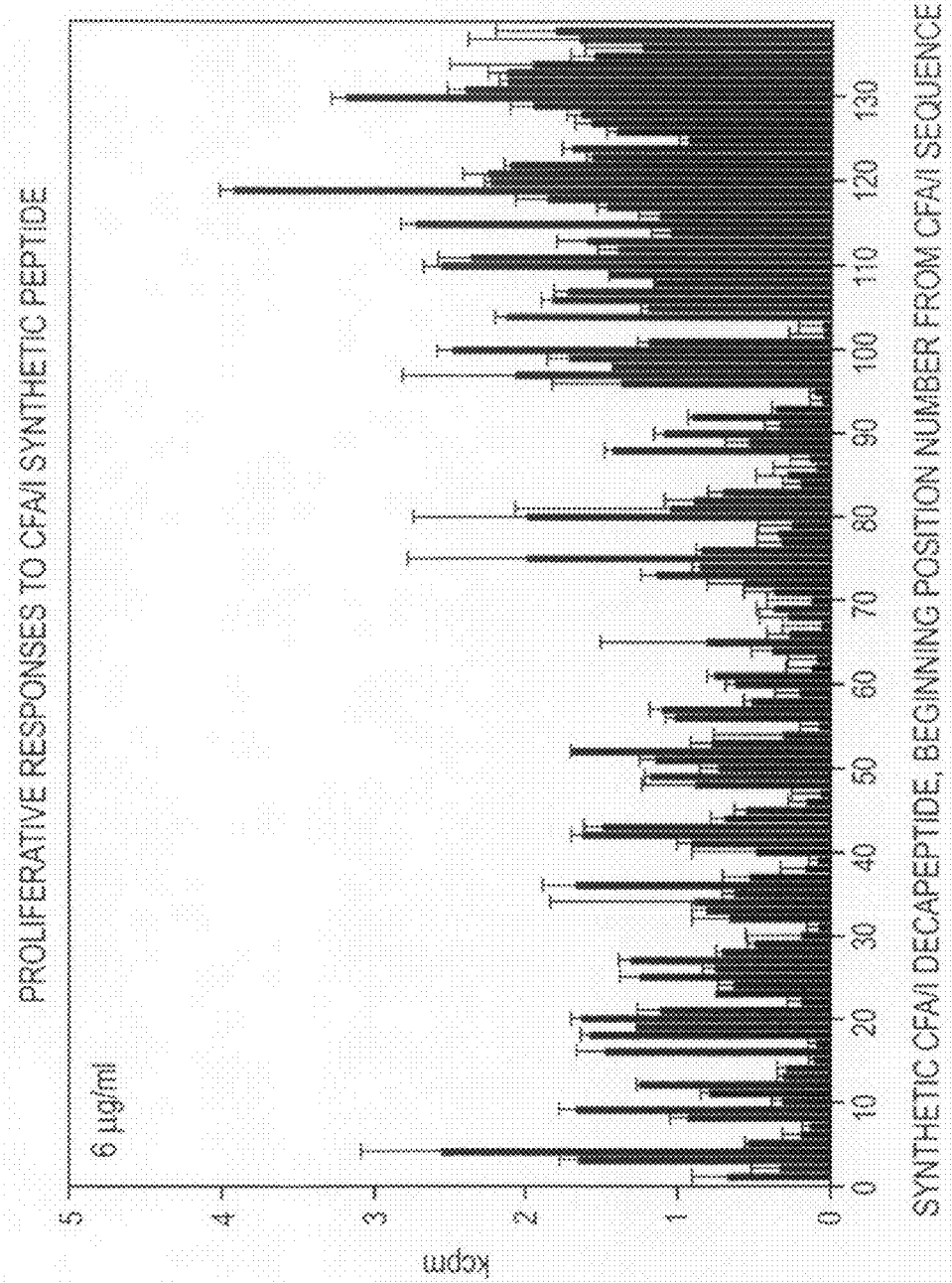
Figure 23:
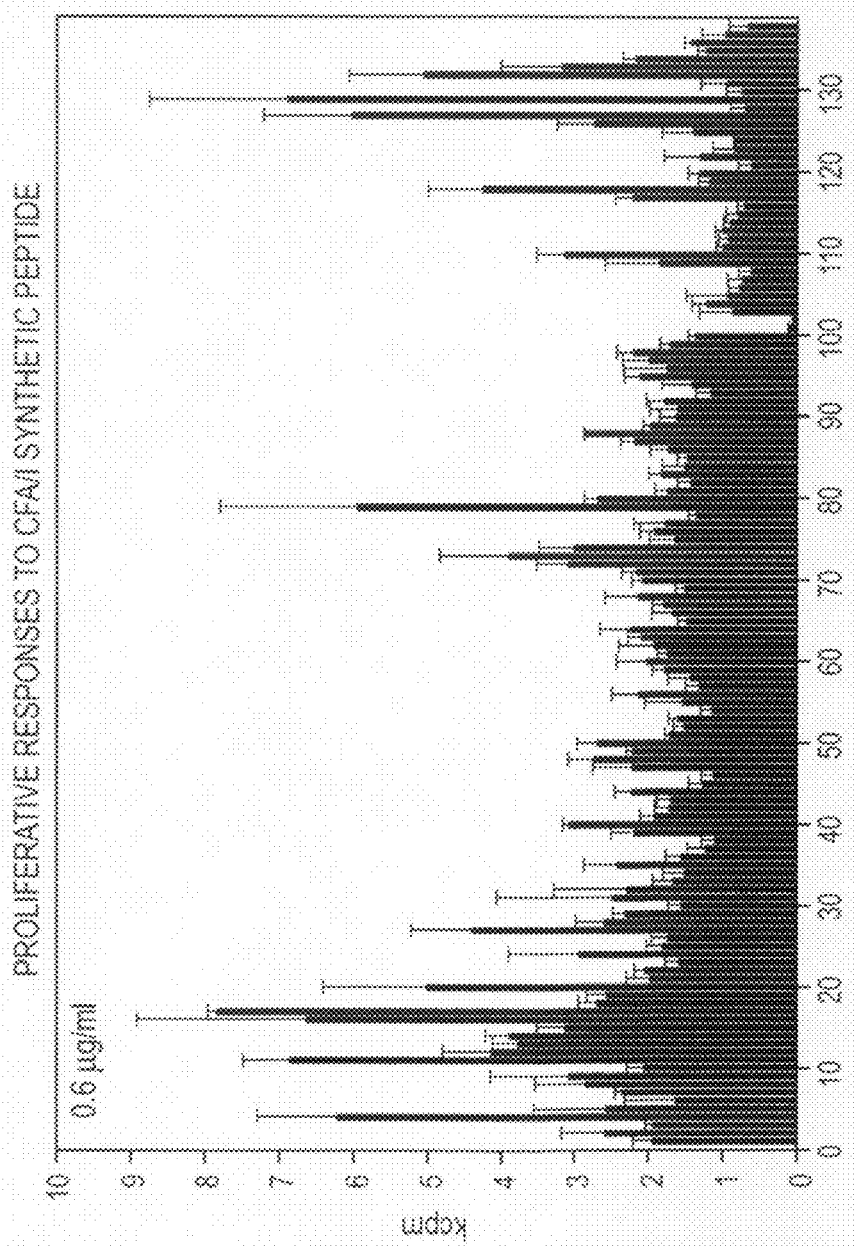

FIGS. 22-24. Lymphocyte proliferation to 6.0, 0.6, and 0.06 micrograms/ml synthetic decapeptides of CFA/I in one monkey. The monkey (2Z2) as immunized with three i.m. injections of CFA/I subunits in adjuvant, and its spleen cells were cultured with synthetic decapeptides which had been constructed using the Pepscan technique. The decapeptides represented the entire CFA/I protein. Values shown represent the proliferative response which occurred to 6.0 micrograms/ml (FIG. 22), 0.6 micrograms/ml (FIG. 23), or 0.06 micrograms/ml (FIG. 24) of antigen±the standard deviation. The cpm of the control peptide was 1,553±33 and the cpm of the media control was 1,951±245.

VII. DETAILED DESCRIPTION OF THE INVENTION

Applicants have discovered efficacious pharmaceutical compositions wherein the relative amounts of antigen to the polymeric matrix are within the ranges of 0.1 to 1% antigen (core loading) and 99.9 to 99% polymer, respectively. It is preferred that the relative ratio between the lactide and glycolide component of the poly(DL-lactide-co-glycolide) (DL-PLG) is within the range of 40:60 to 0:100. However, it is understood that effective core loads for certain antigens will be influenced by its microscopic form (i.e. bacteria, protozoa, viruses or fungi) and type of infection being prevented. From a biological perspective, the DL-PLG or glycolide monomer excipient are well suited for in vitro drug (antigen) release because they elicit a minimal inflamatory response, are biologically compatible, and degrades under physiologic conditions to products that are nontoxic and readily metabolized.

Surprisingly, applicants have discovered an extremely effective method for the protection against bacterial or viral infections in the tissue of a mammal (human or nonhuman animal) caused by enteropathogenic organisms comprising administering orally to said animal an immunogenic amount of a pharmaceutical composition consisting essentially of an antigen encapsulated within a biodegradable polymeric matrix. When the polymeric matrix is DL-PLG, the most preferred relative ratio between the lactide and glycolide component is within the range of 48:52 to 58:42. The bacterial infection can be caused by bacteria (including any derivative thereof) which include *Salmonella typhi, Shigella sonnei, Shigella flexneri, Shigella dysenteriae, Shigella boydii, Escheria coli, Vibro cholera, versinia, staphylococcus, clostridium* and *campylobacter*. Representative viruses contemplated within the scope of this invention, susceptible to treatment with the above-described pharmaceutical compositions, are quite extensive. For purposes of illustration, a partial listing of these viruses (including any derivative thereof) include hepatitis A, rotaviruses, polio virus human immunodeficiency viruses (HIV), Herpes Simplex virus type 1 (cold sores), Herpes Simplex virus type 2 (Herpesvirus genitalis), Varicella-zoster virus (chicken pox, shingles), Epstein-Barr virus (infectious mononucleosis; glandular fever; and Burkittis lymphoma), and cytomegalo viruses.

A further representation description of the instant invention is as follows:

A. (1) To homogeneously disperse antigens of enteropathic organisms within the polymeric matrix of biocompatible and biodegradable microspheres, 1 to 12 microns in diameter, utilizing equal molar parts of polymerized lactide and glycolide (50:50 DL-PLG, i.e. 48:52 to 58:42 DL-PLG) such that the core load is within the range of about 0.1 to 1% by weight. The microspheres containing the dispersed antigen can then be used to immunize the intestine to produce a humoral immune response composed of secretory antibody, serum antibody and a cellular immune response consisting of specific T-cells and B-cells. The immune response is directed against the dispersed antigen and will give protective immunity against the pathogenic organism from which the antigen was derived.

(2) AF/R1 pilus protein is an adherence factor that allows *E. coli* RDEC-1 to attach to rabbit intestinal brush borders thus promoting colonization resulting in diarrhea. AF/R1 pilus protein was homogeneously dispersed within a polymeric matrix of biocompatible and biodegradable microspheres, 1-12 microns in diameter (FIG. 1 and photograph 1); using equal molar parts of polymerized lactide and glycolide (50:50 DL-PLG) such that the core load was 0.62% by weight.

(3) The microspheres were found to contain immunogenic AF/RI by immunizing both rabbit spleen (FIG. 2) and Peyer's patch (FIG. 3) B-cells in vitro. The resultant cell supernatants contained specific IgM antibody which recognized the AF/R1. The antibody response was comparable to immunizing with AF/R1 alone.

Figure 10A:
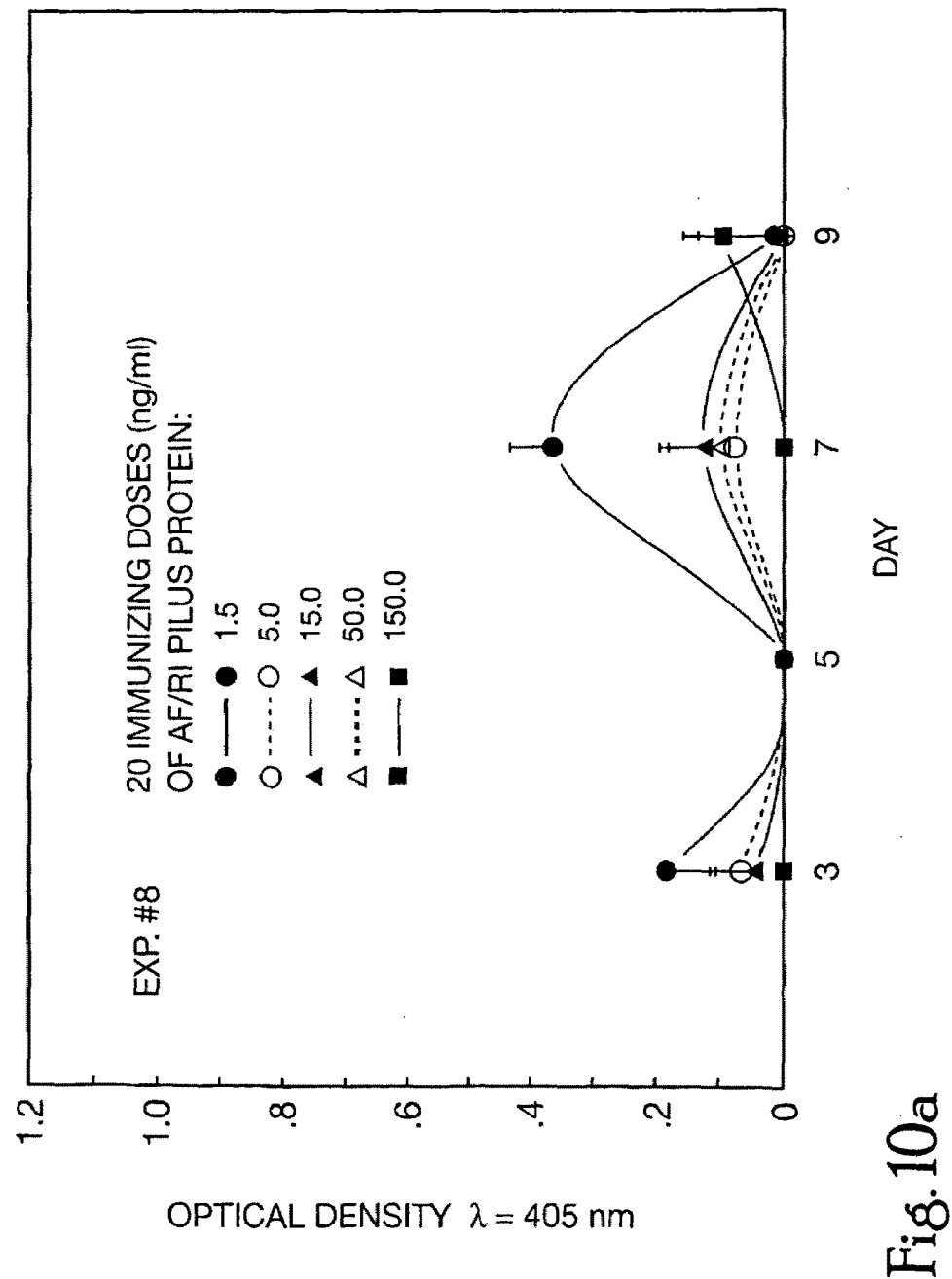
Figure 10C:
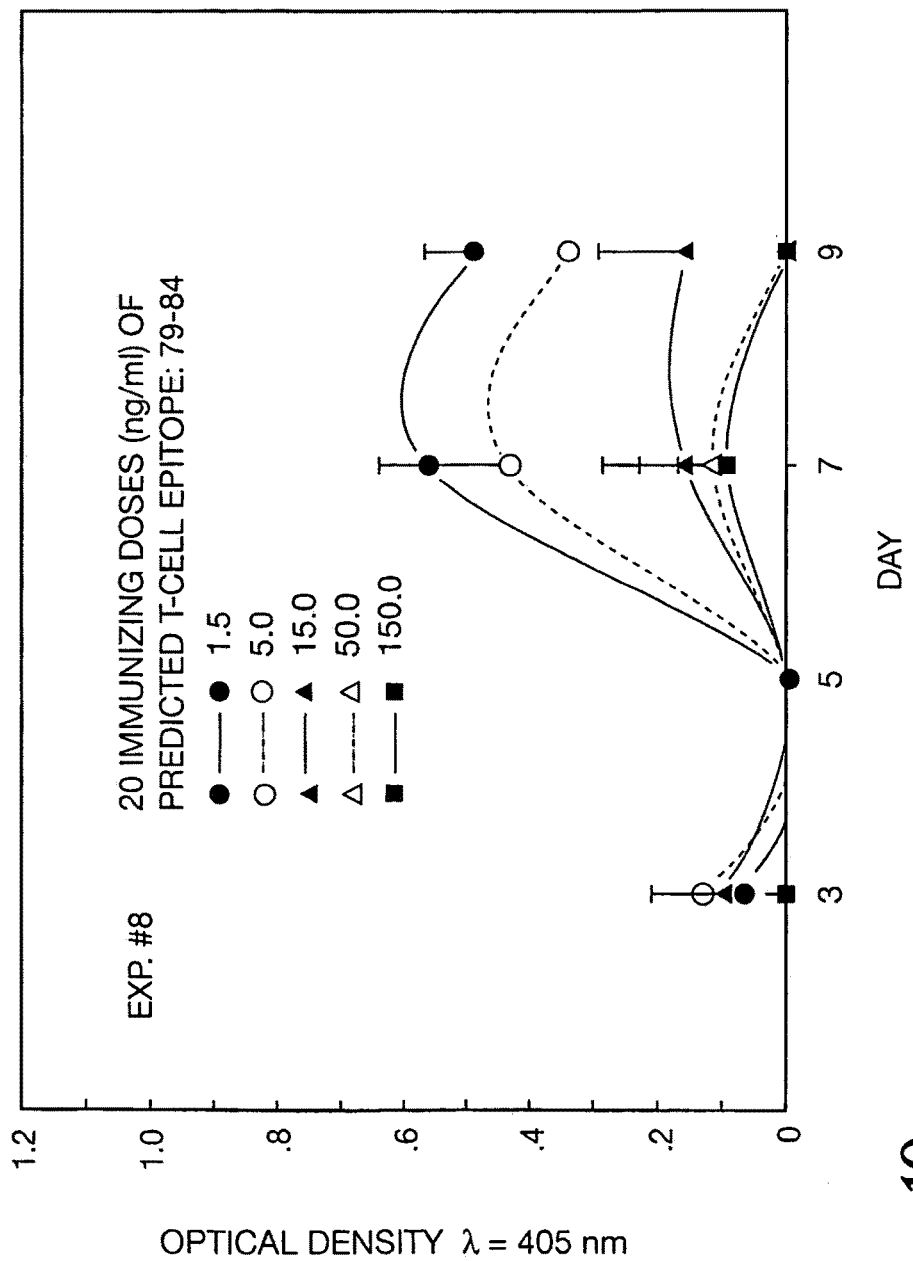
Figure 10D:
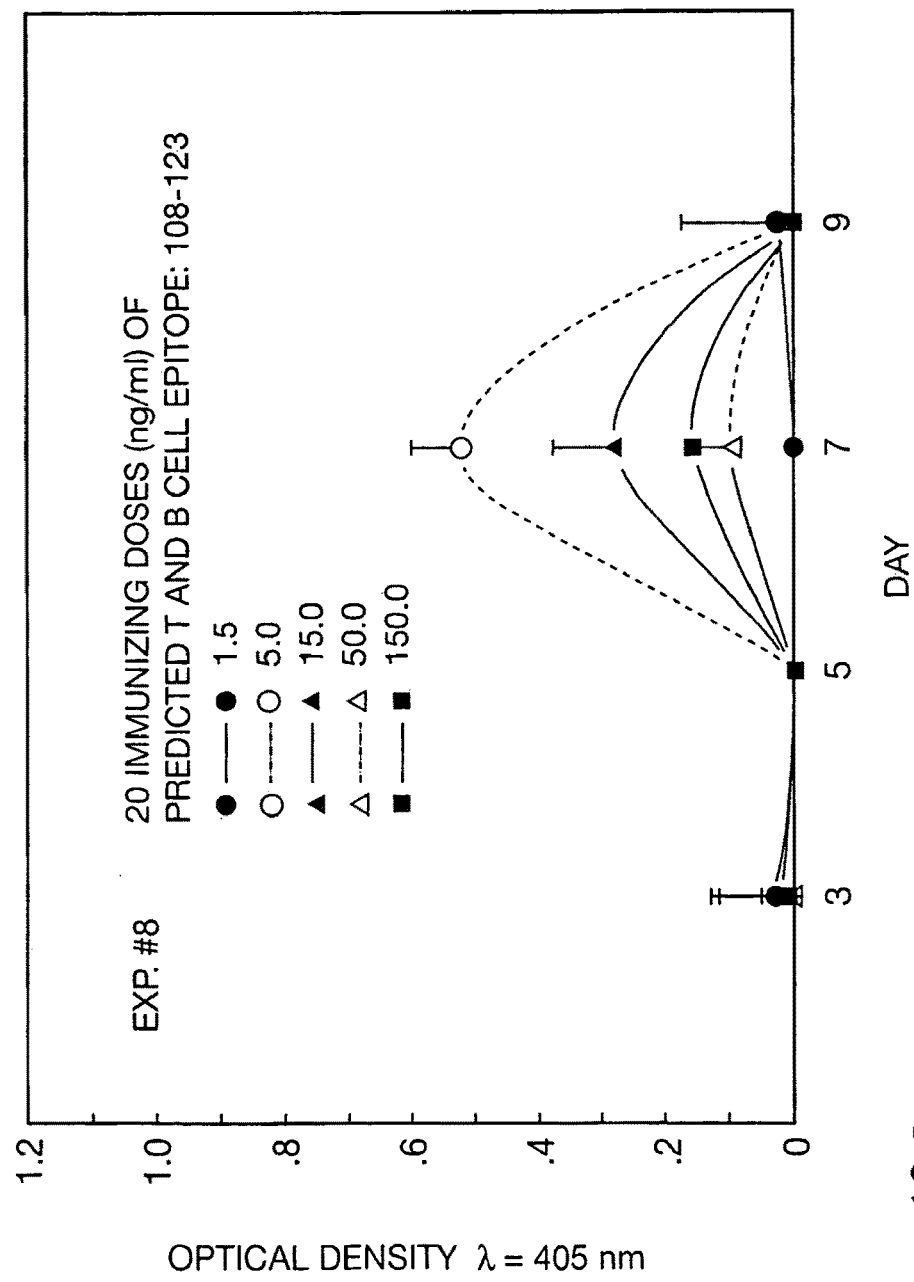
Figure 11:
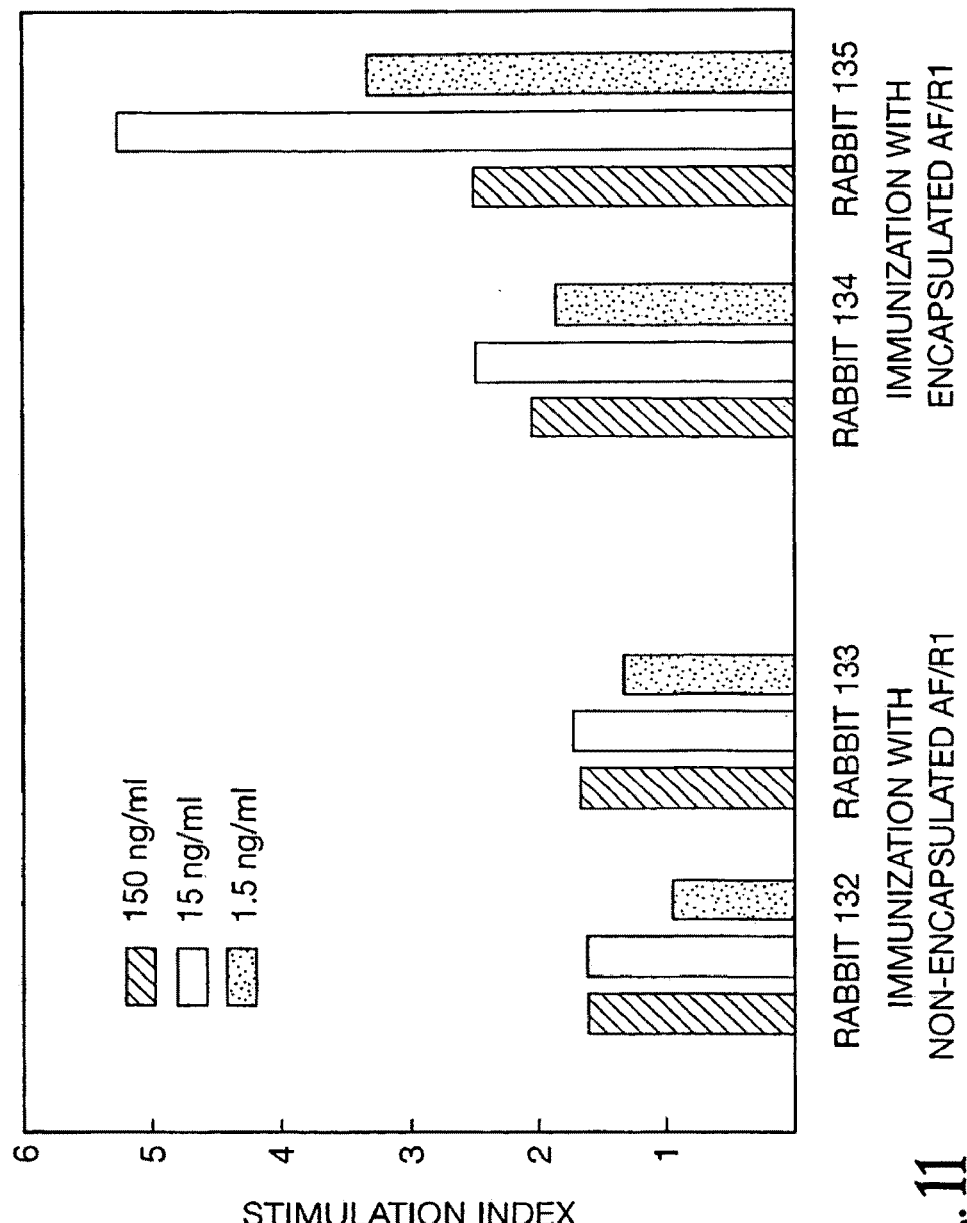
Figure 10B:
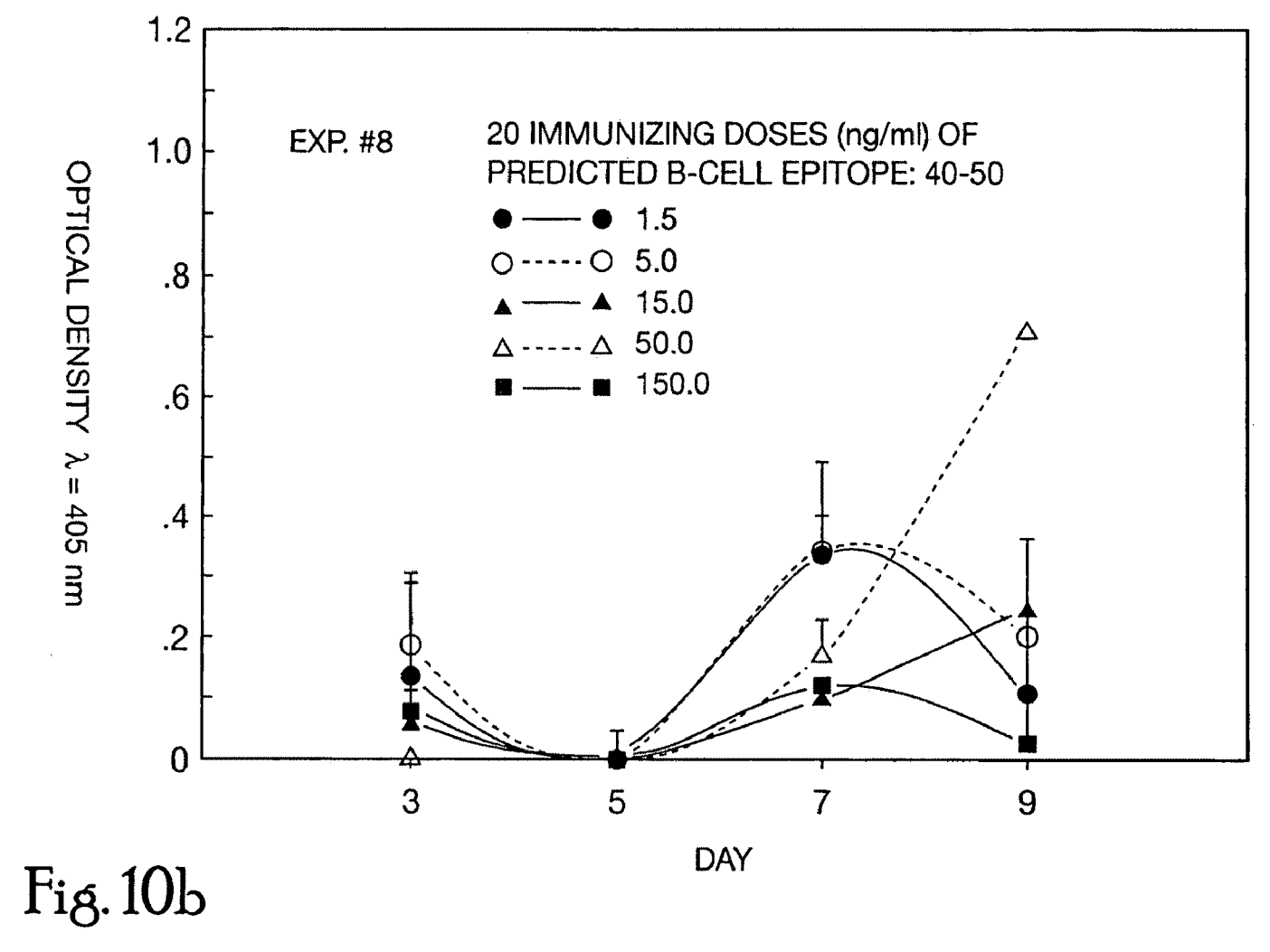

(4) Microspheres containing 50 micrograms of AF/R1 were used to intraintestinally (intraduodenally) immunize rabbits on two separate occasions 1 week apart. One week later, compared to rabbits receiving AF/R1 alone, the intestinal lymphoid tissue, Peyer's patches, demonstrated an enhanced cellular immune response to AF/R1 and to three AF/R1 linear peptide fragments 40-55, 79-94 and 108-123 by both lymphocyte transformation (T-cells) (FIGS. 4 and 5) and antibody producing B-cells (FIGS. 6 and 7). Similarly enhanced B-cell responses were also detected in the spleen (FIGS. 8 and 9). An enhanced T-cell response was also detected in the mesenteric lymph node and the spleen to one AF/R1 peptide fragment, 40-55 (FIGS. 10 and 11). The cellular immune response at two weeks was too early for either a serum or secretory antibody response (See Results in Table 1); but indicates that a secretory antibody response will develop such that the rabbits so immunized could be protected upon challenge with the *E. coli* RDEC-1.

B. Microspheres do not have to be made up just prior to use as with liposomes. Also liposomes have not been effective in rabbits for intestinal immunization of lipopolysaccharide antigens.

C. (1) Only a small amount of antigen is required (ugs) when dispersed within microspheres compared to larger amounts (mgms) when antigen is used alone for intestinal immunization.

(2) Antigen dispersed within microspheres can be used orally for intestinal immunization whereas antigen alone used orally even with gastric acid neutralization requires a large amount of antigen and may not be effective for intestinal immunization.

(3) Synthetic peptides with and without attached synthetic adjuvants representing peptide fragments of protein antigens can also be dispersed within microspheres for oral-intestinal immunization. Free peptides would be destroyed by digestive processes at the level of the stomach and intestine. Any surviving peptide would probably not be taken up by the intestine and therefore be ineffective for intestinal immunization.

(4) Microspheres containing antigen maybe placed into gelatin-like capsules for oral administration and intestinal release for improved intestinal immunization.

(5) Microspheres promote antigen uptake from the intestine and the development of cellular immune (T-cell and B-Cell) responses to antigen components such as linear peptide fragments of protein antigens.

(6) The development of intestinal T-cell responses to antigens dispersed within microspheres indicate that T-cell immunological memory will be established leading to long-lived intestinal immunity. This long-lived intestinal immunity (T-cell) is very difficult to establish by previous means of intestinal immunization. Failure to establish long-lived intestinal immunity is a fundamental difficulty for intestinal immunization with non-viable antigens. Without intestinal long-lived immunity only a short lived secretory antibody response is established lasting a few weeks after which no significant immunological protection may remain.

D. (1) Oral intestinal immunization of rabbits against *E. coli* RDEC-1 infection using either whole killed organisms, pilus protein preparations or lipopolysaccharide preparations.

(2) Microspheres containing adherence pilus protein AF/R1 or its antigen peptides for oral intestinal immunization of rabbits against RDEC-1 infection.

(3) Oral-intestinal immunization of humans against enterotoxigenic *E. coli* infection using either whole killed organisms, pilus protein preparations or lipopolysaccharide preparations.

(4) Microspheres containing adherence pilus proteins CFA/I, II, III and IV or their antigen peptides for oral intestinal immunization of humans against human enterotoxigenic *E. coli* infections.

(5) Oral-intestinal immunization of humans against other enteric pathogens as *salmonella, shigella*, camphlobacter, hepatitis-A virus, rota virus and polio virus.

(6) Oral-intestinal immunization of animals and humans for mucosal immunological protection at distal mucosal sites as the bronchial tree in lungs, genitourinary tract and breast tissue.

E. (1) The biocompatible, biodegradable co-polymer has a long history of being safe for use in humans since it is the same one used in resorbable suture material.

(2) By using the microspheres, we are now able to immunize the intestine of animals and man with antigens not normally immunogenic for the intestinal mucosa because they are either destroyed in the intestine, unable to be taken up by the intestinal mucosa or only weakly immunogenic if taken up.

(3) Establishing long-lived immunological memory in the intestine is now possible because T-cells are immunized using microspheres.

(4) Antigens that can be dispersed into microspheres for intestinal immunization include the following: proteins, glycoproteins, synthetic peptides, carbohydrates, synthetic polysaccharides, lipids, glycolipids, lipopolysaccharides (LPS), synthetic lipopolysaccharides and with and without attached adjuvants such as synthetic muramyl dipeptide derivatives.

(5) The subsequent immune response can be directed to either systemic (spleen and serum antibody) or local (intestine, Peyer's patch) by the size of the microspheres used for the intestinal immunization. Microspheres 5-10 microns in diameter remain within macrophage cells at the level of the Peyer's patch in the intestine and lead to a local intestinal immune response. Microspheres 1-5 microns in diameter leave the Peyer's patch contained within macrophages and migrate to the mesenteric lymph node and to the spleen resulting in a systemic (serum antibody) immune response.

(6) Local or systemic antibody mediated adverse reactions because of preexisting antibody especially cytophyllic or IgE antibody may be minimized or eliminated by using microspheres because of their being phagocytized by macrophages and the antigen is only available as being attached to the cell surface and not free. Only the free antigen could become attached to specific IgE antibody bound to the surface of mast cells resulting in mast cell release of bioactive amines necessary for either local or systemic anaphylaxis.

(7) Immunization with microspheres containing antigen leads to primarily IgA and IgG antibody responses rather than an IgE antibody response, thus preventing subsequent adverse IgE antibody reactions upon reexposure to the antigen.

In addition to the above, the encapsulation of the following synthetic peptides are contemplated and considered to be well within the scope of this invention:

(1) AF/R1 40-55;
(2) AF/R1 79-94;
(3) AF/R1 108-123;
(4) AF/R1 1-13;
(5) AF/R1 pepscan 16AA;
(6) CFA/I 1-13; and
(7) CFA/I pepscan 16AA.
(8) Synthetic Peptides containing CFA/I Pilus Protein T-cell Epitopes (Starting Sequence # given)
(SEQ ID NO: 1) 4 (Asn-Ile-Thr-Val-Thr-Ala-Ser-Val-Asp-Pro),
(SEQ ID NO: 2) 8(Thr-Ala-Ser-Val-Asp-Pro-Val-Ile-Asp-Leu),
(SEQ ID NO: 3) 12 (Asp-Pro-Val-Ile-Asp-Leu-Leu-Gln-Ala-Asp),
(SEQ ID NO: 4) 15 (Ile-Asp-Leu-Leu-Gln-Ala-Asp-Gly-Asn-Ala),
(SEQ ID NO: 5) 20 (Ala-Asp-Gly-Asn-Ala-Leu-Pro-Ser-Ala-Val),
(SEQ ID NO: 6) 26 (Pro-Ser-Ala-Val-Lys-Leu-Ala-Tyr-Ser-Pro),
(SEQ ID NO: 7) 72 (Leu-Asn-Ser-Thr-Val-Gln-Met-Pro-Ile-Ser),
(SEQ ID NO: 8) 78 (Met-Pro-Ile-Ser-Val-Ser-Trp-Gly-Gly-Gln),
(SEQ ID NO: 9) 87 (Gln-Val-Leu-Ser-Thr-Thr-Ala-Lys-Glu-Phe),
(SEQ ID NO: 10) 126 (Ala-Gly-Thr-Ala-Pro-Thr-Ala-Gly-Asn-Tyr,), and
(SEQ ID NO: 11) 133 (Gly-Asn-Tyr-Ser-Gly-Val-Val-Ser-Leu-Val), and mixtures thereof
(9) Synthetic Peptides Containing CFA/I Pilus Protein B-cell (antibody) Epitopes (Starting Sequence # given)
(SEQ ID NO: 12) 3 (Lys-Ana-Ile-Thr-Val-Thr-Ala-Ser-Val),
(SEQ ID NO: 13) 11 (Val-Asp-Pro-Val-Ile-Asp-Leu-Leu-Gln-Ala-Asp),
(SEQ ID NO: 14) 22 (Gly-Asn-Ala-Leu-Pro-Ser-Ala-Val),
(SEQ ID NO: 15) 32 (Ala-Tyr-Ser-Pro-Ala-Ser-Lys-Thr-Phe-Lys-Thr-Phe-Glu-Ser-Tyr-Arg-Val),
(SEQ ID NO: 16) 32 (Ala-Tyr-Ser-Pro-Ala-Ser-Lys-thr-Phe),
(SEQ ID NO: 17) 38 (Lys-Thr-Phe-Glu-Ser-Tyr-Arg-Val),
(SEQ ID NO: 18) 66 (Pro-Gln-Leu-Thr-Asp-Val-Leu-Asn-Ser),
(SEQ ID NO: 19) 93 (Ala-Lys-Glu-Phe-Glu-Ala-Ala-Ala),
(SEQ ID NO: 20) 124 (Lys-Thr-Ala-Gly-Thr-Ala-Pro-Thr),
(SEQ ID NO: 21) 127 (Lys-Thr-Ala-Gly-Thr-Ala-Pro-Thr),
(SEQ ID NO: 22) 124 (Lys-Thr-Ala-Gly-Thr-Ala-Pro-Thr-Ala-Gly-Asn-Tyr-Ser), and mixtures thereof.
(9) Synthetic Peptides Containing CFA/I pilus Protein T-cell And B-cell (antibody) Epitopes (Starting Sequence # given)
(SEQ ID NO: 23) 3 (Lys-Asn-Ile-Thr-Val-Thr-Ala-Ser-Bal-Asp-Pro)
(SEQ ID NO: 24) 8 (Thr-Ala-Ser-Bal-Asp-Pro-Bal-Ile-Asp-Leu-Leu-Gln-Ala-Asp),
(SEQ ID NO: 13) 11 (Bal-Asp-Pro-Bal-Ile-Asp-Leu-Leu-Gln-Ala-Asp),
(SEQ ID NO: 5) 20 (Ala-Asp-Gly-Asn-Ala-Leu-Pro-Ser-Ala-Val),
(SEQ ID NO: 22) 124 (Lys-Thr-Ala-Gly-Thr-Ala-Pro-Thr-Ala-Gly-Asn-Tyr-Ser), and
(SEQ ID NO: 25) 126 (Ala-Gly-Thr-Ala-Pro-Thr-Ala-Gly-Asn-Tyr-Ser), and mixtures thereof.

We contemplate that the peptides can be used in vaccine constructed for systemic administration.

VIII. EXAMPLES

The peptides in (8), (9), and (10) above can be made by classical solution phase synthesis, solid phase synthesis or recombinant DNA technology. These peptides can be incorporated in an oral vaccine to prevent infection by CFA/I bearing enteropathogenic *E. coli*.

The herein offered examples provide methods for illustrating, without any implied limitation, the practice of this invention in the prevention of diseases caused by enteropathogenic organisms.

The profile of the representative experiments have been chosen to illustrate the effectiveness of the immunogenic polymeric matrix-antigen composites.

All temperatures not otherwise indicated are in degrees Celcius (° C.) and parts or percentages are given by weight.

IX. MATERIALS AND METHODS

Animals. New Zealand White male rabbits were purchased from Hazelton Research Products (Denver, Pa.), and were shown to be free of current RDEC-1 infection by culture of rectal swabs. Animals were 1-2 kg of body weight and lacked agglutinating anti-AF/R1 serum antibody at the time of the study.

Antigens. AF/R1 pili from *E. coli* RDEC-1 (015:H:K nontypable) were purified by an ammonium sulfate precipitation method. The final preparation migrated as a single band on SDS-polyacrylamide gel electrophoresis and was shown to be greater than 95% pure by scanning with laser densitometry when stained with coomassie blue. Briefly, equal molar parts of DL-lactide and glycolide were polymerized and then dissolved to incorporate AF/R1 into spherical particles. The microspheres contained 0.62% protein by weight and ranged in size from 1 to 12 micrometers. Both the microencapsuled and non-encapsulated AF/R1 were sterilized by gamma irradiation (0.3 megarads) before use.

Synthetic peptides (16 amino acids each) were selected by theoretical criteria from the amino acid sequence of AF/R1 as deduced from the nucleotide sequence. Three sets of software were used for the selections. Software designed to predict B cell epitopes based on hydrophilicity, flexibility, and other criteria was developed by the University of Wisconsin Genetics Computer Group. Software designed to predict T cell epitopes was based on the Rothbard method was written by Stephen Van Albert (The Walter Reed Army Institute of Research, Washington, D.C.). Software designed to predict T cell epitopes based on the Berzofsky method is published as the AMPHI program. The selected peptides were synthesized by using conventional Merrifield solid phase technology. AF/R1 40-55 (SEQ ID NO: 28) (Thr-Asn-ala-Cly-thr-Asp-Ile-Gly-Ala-Asn-Lys-Ser-Phe-thr-Leu-Lys) was chosen as a probable B cell epitope for two reasons: (a) due to its high hydrophilic and flexibility indices, and (b) because it was not predicted to be a T cell epitope by either the Rothbard or Berzofsky method. AF/F1 79-94 (SEQ ID NO: 29) (Val-Asn-Gly-Ile-Gly-Asn-Leu-Ser-Gly-Lys-Ala-Ile-Asp-Ala-His-Val) was selected as a probable T cell epitope by both methods and because of its relatively low hydrophilic and flexibility indices.

AF/R1 108-123 (SEQ ID NO: 26) (Asp-Thr-Asn-Ala-Asp-Lys-Glu-Ile-Lys-Ala-Gly-Gln-Asn-Thr-Val-Asp) was selected as both a T and B cell epitope. AF/R1 40/47/79-86 was produced in continuous synthesis (SEQ ID NO: 27) (Thr-Asn-Ala-Cly-Thr-Asp-Ile-Gly-Val-Asn-Gly-Ile-Gly-Asn-Leu-Ser) and represents a hybrid of the first eight amino acids from the predicted B cell epitope and the T cell epitope. The purity of each peptide was confirmed by C-8 reverse phase HPLC, and all peptides were desalted over a Sephadex G-10 column before use. Using a standard ELISA method, all peptides were assayed for their ability to specifically bind anti-AF/R1 IgG antibody in hyperimmune serum from a rabbit which had received intramuscular injections of AF/R1 pili in Freund adjuvant. Only the peptide chosen as a probable B cell epitope (AF/R1 40-55) was recognized by the hyperimmune serum.

Example

Immunization. Rabbits were primed twice with 50 micrograms of either microencapsulated or non-encapsulated AF/R1 by endoscopic intraduodenal inoculation seven days apart by the following technique. All animals were fasted overnight and sedated with an intramuscular injection of xylazine (10 mg) and Ketamine HCl (50 mg). An Olympus BF type P10 endoscope was advanced under direct visualization through the esophagus, stomach, and pylorus, and a 2 mm ERCP catheter was inserted through the biopsy channel and threaded 2-3 cm into the small intestine. Inoculums of pili or pili embedded in microspheres were injected through the catheter into the duodenum and the endoscope was withdrawn. Animals were monitored daily for signs of clinical illness, weight gain, or colonization by RDEC-1.

Example 2

Lymphocyte Proliferation. Seven days following the second priming, the rabbits were again sedated with a mixture of xylazine and katamine HCl, and blood was drawn for serum preparation by cardiac puncture. Animals were then euthanized with an overdose of pentothal and tissues including Peyer's patches from the small bowel, MLN, and spleen were removed. Single cell suspension were prepared and washed in Dulbeco's modified Eagle medium (Gibco Laboratories, Grand Island, N.Y.) which had been supplemented with penicillin (100 units/ml), streptomycin (100 micrograms/ml), L-glutamine (2 mM), and HEPES Buffer (10 mM) all obtained from Gibco Laboratories, as well as MEM non-essential amino acid solution (0.1 mM), MEM [50×] amino acids (2%), sodium bicarbonate (0.06%), and $5\times10^{-5}$ micrograms 2-ME all obtained from Sigma Chemical Company (St. Louis, Mo.) [cDMEM]. Erythrocytes in the spleen cell suspension were lysed using standard procedures in an ammonium chloride lysing buffer. Cell suspension were adjusted to $5\times10^6$ cells per ml in cDMEM, and autologous serum was added to yield a final concentration of 0.5%. Cells (0.1 ml) were placed in 96-well flat bottom culture plates (Costar, Cambridge, Mass.) along with 0.1 ml of various dilutions of antigen and were incubated at 37° C. in 5% $CO_2$. In other experiments, cultures were conducted in a 24-well plates. In these experiments, $5\times10^6$ cells were cultured with or without antigen in a 2 ml volume. After 4 days, 100 microliters aliquots of cells were transferred to 96-well plates for pulsing and harvesting. Previous experiments have demonstrated that optimal concentrations of antigen range from 150 ng/ml to 15 micrograms/ml in the 96-well plate assay and 1.5 ng/ml to 150 ng/ml in the 24-well plate assay. These were the concentrations employed in the current study. All cultures were pulsed with 1 Ci [$^3$H]thymidine (25 Ci/mmol, Amersham, Arlington Heights, Ill.) on day 4 of culture and were harvested for scintillation counting 6 hours later.

Statistics. All cultures were conducted in replicates of four, and standard deviations of the counts per minute (cpm) generally range from 5-15% of the average cpm. In experiments where comparison of individual animals and groups of animals is desirable, data is shown as a stimulation index (SI) to facilitate the comparison. SI were calculated by dividing the mean of cultures with antigen by the mean of cultures without antigen (media control). Statistical significance (p value) was determined by comparing the maximum response for each antigen to the media control using the Student's t test.

IX. RESULTS

Figure 13:
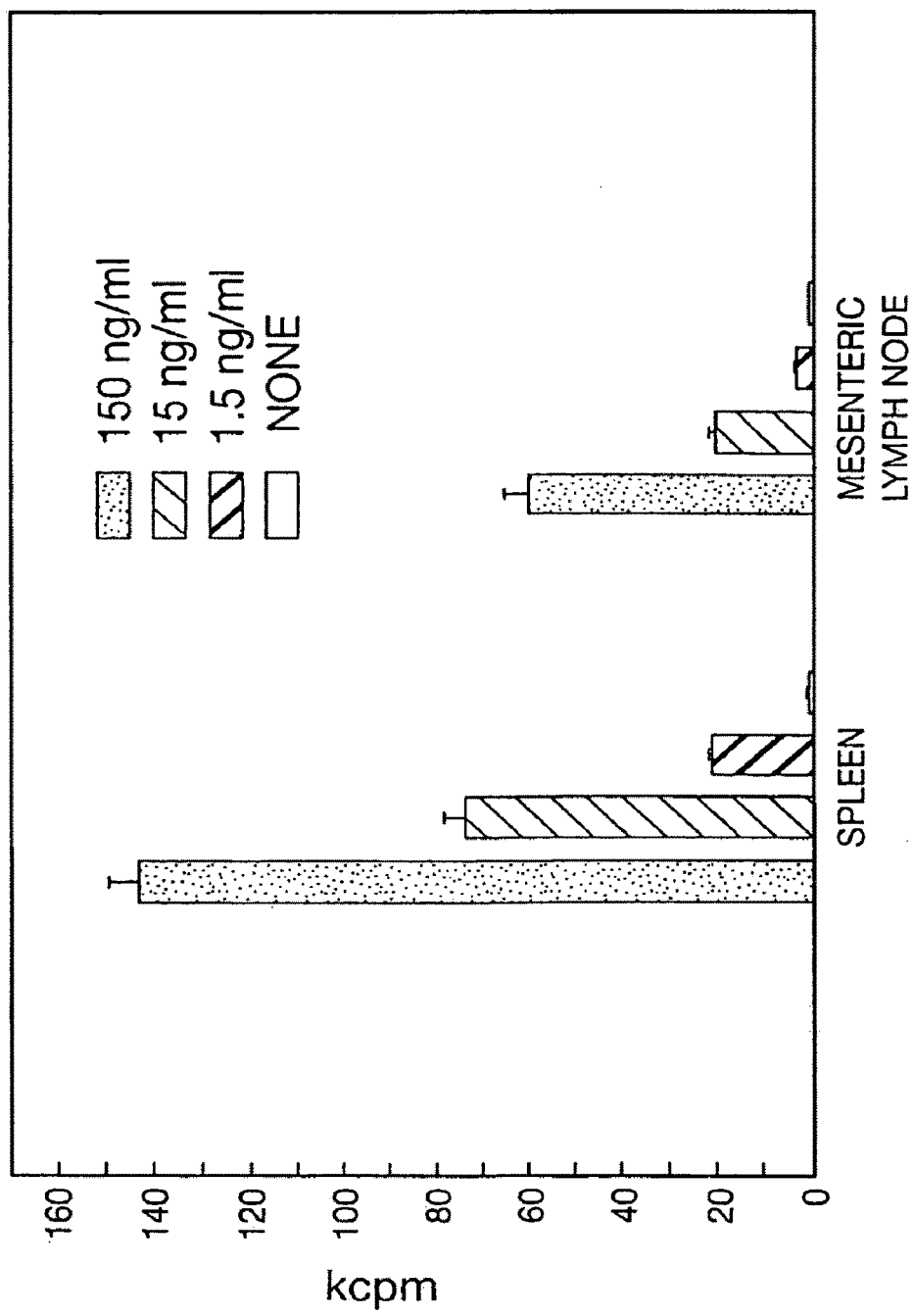
FIG. 13 is a graph showing lymphocyte proliferation of spleen and MLN cells in response to protein and peptide antigens of AF/R1.
Figure 14:
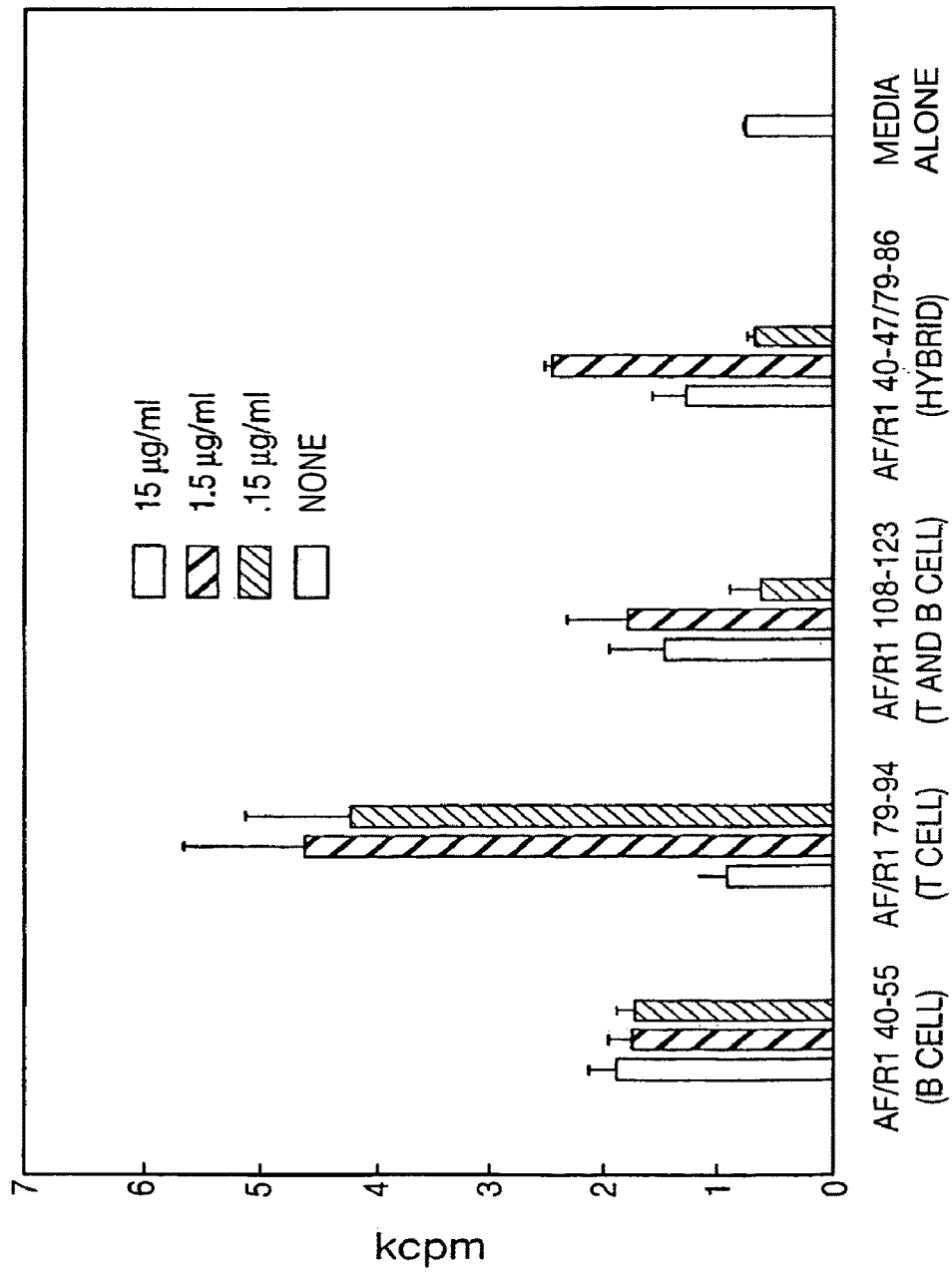
FIG. 14 is a graph showing lymphocyte proliferation of spleen cells to all the synthetic AF/R1 peptides tested as compared to cell cultures without antigen.

Lymphocyte proliferation in response to protein and peptide antigens of AF/R1. To determine if lymphoid tissues from AF/R1 immune animals respond in vitro to the antigens of AF/R1, the immunity in a rabbit with preexisting high levels of anti-AF/R1 serum IgG was boosted twice by injection of 50 micrograms of purified AF/R1 pili i.p. seven days apart. A week after the final boost, in vitro lymphocyte proliferation of spleen and MLN cells demonstrated a remarkable response to AF/R1 pili (FIG. 13). In response to the synthetic peptides, there was a small, but significant proliferation of the spleen cells to all the AF/R1 peptides tested as compared to cell cultures without antigen (FIG. 14). Cells from the spleen and Peyer's patches of non-immune animals failed to respond to either AF/R1 or the synthetic peptides.

Figure 5:
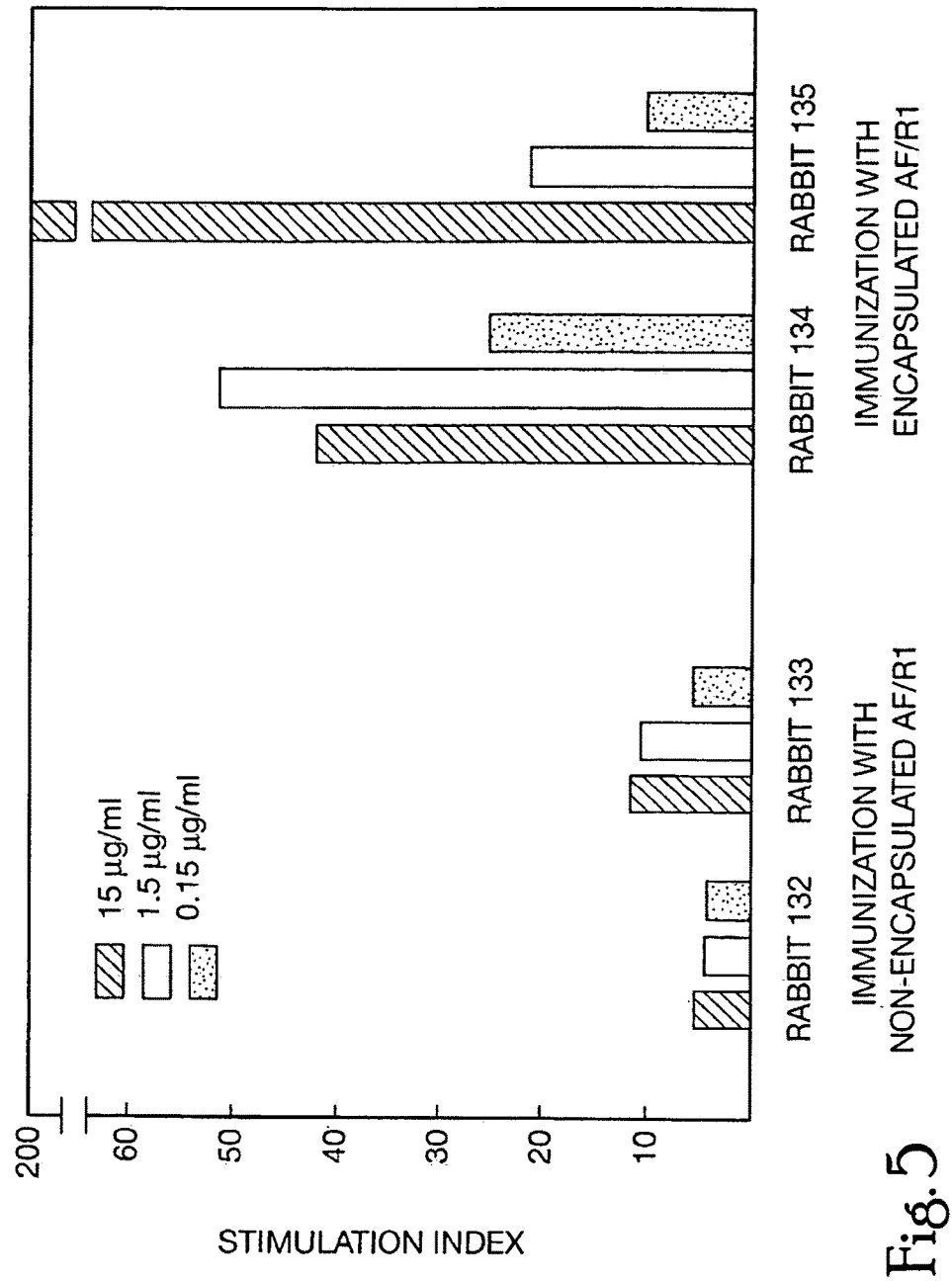
Figure 6A:
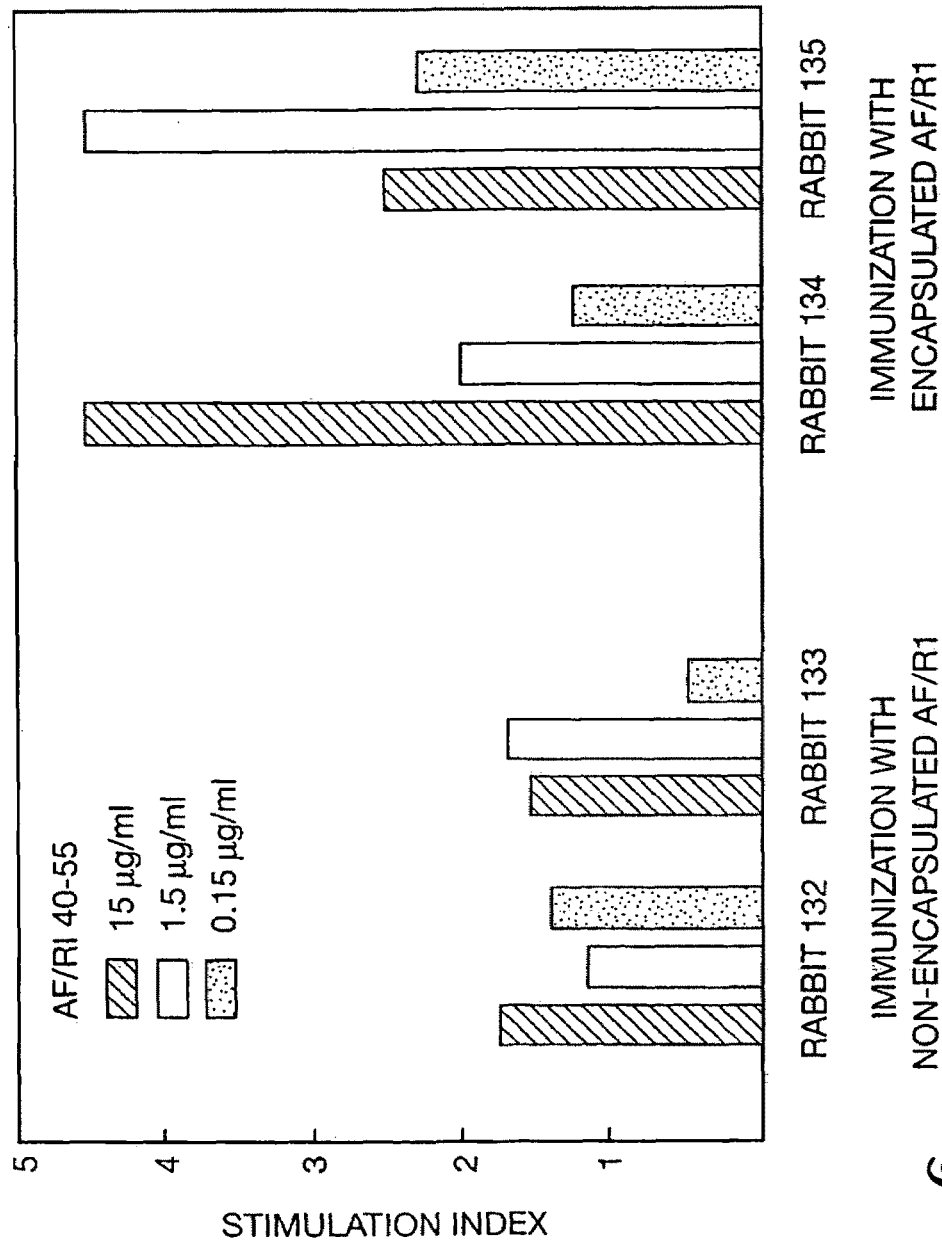
Figure 6B:
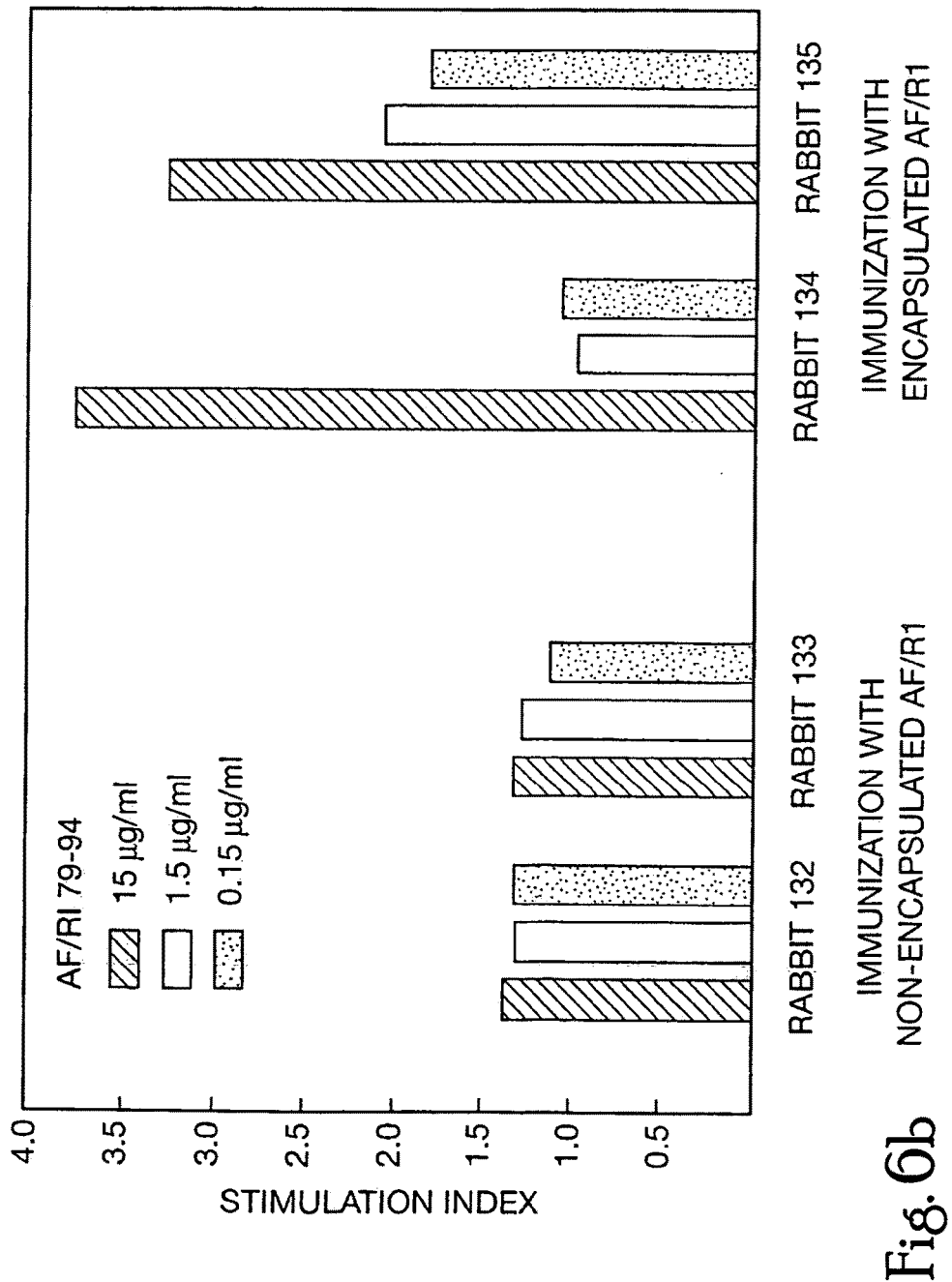
Figure 6C:
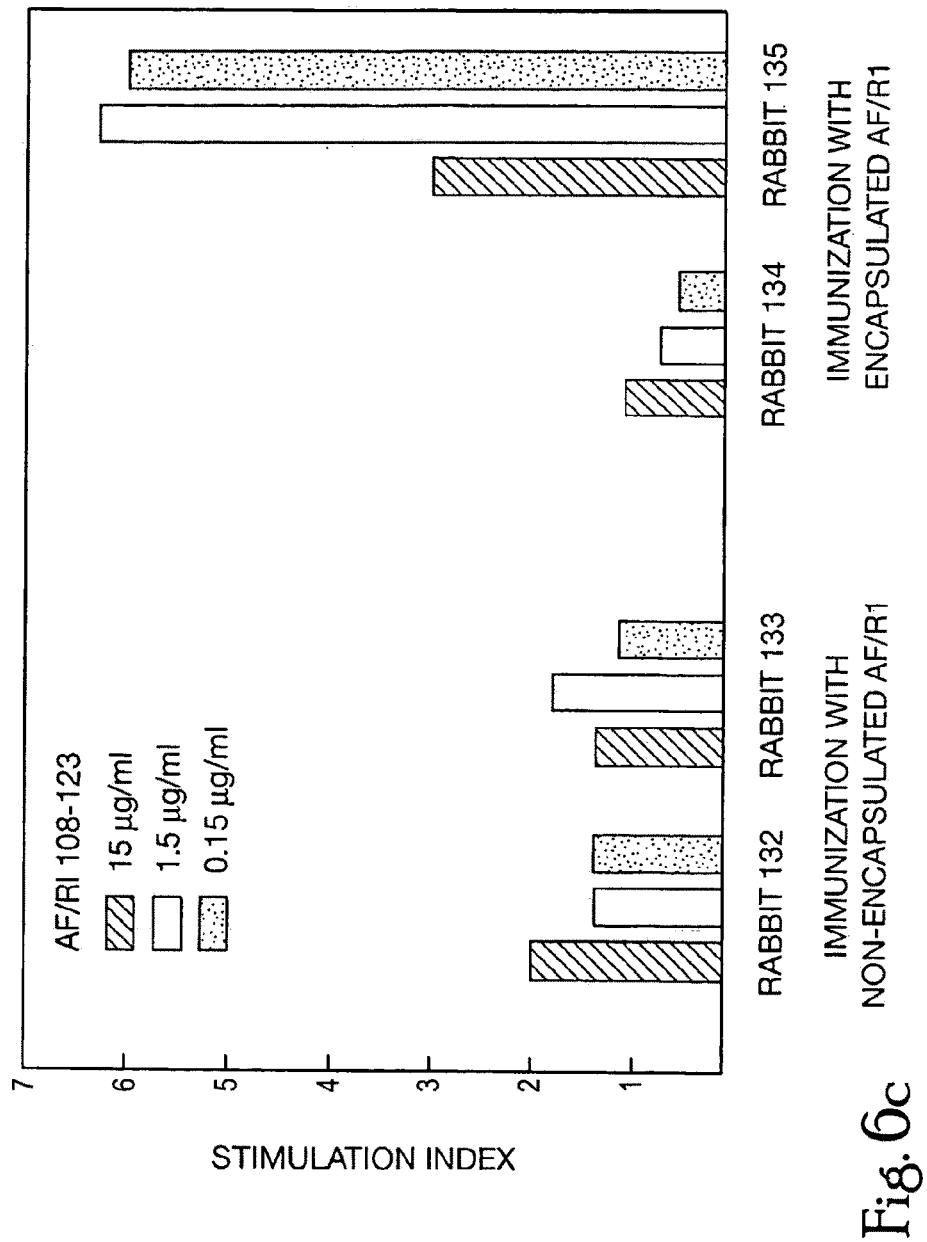
Figure 6D:
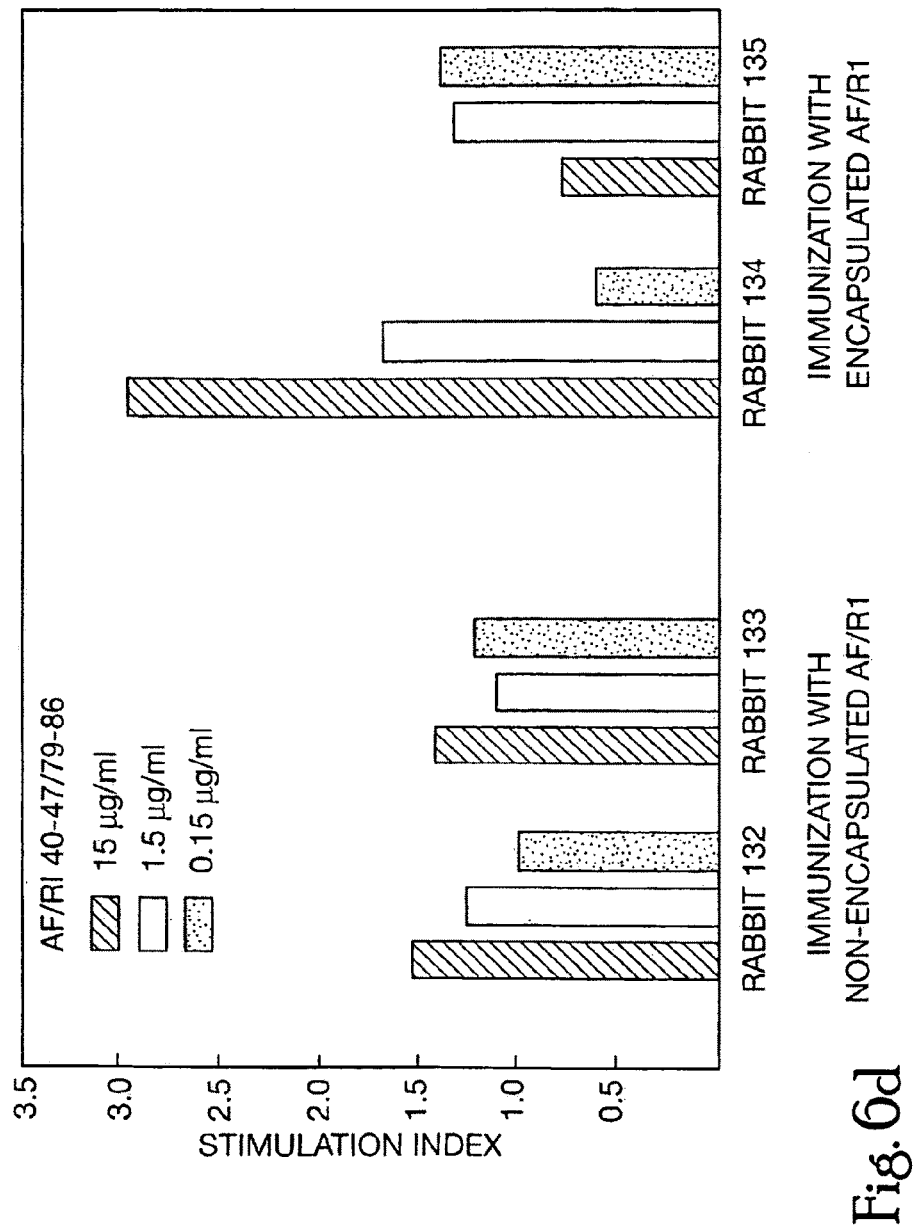
Figure 7A:
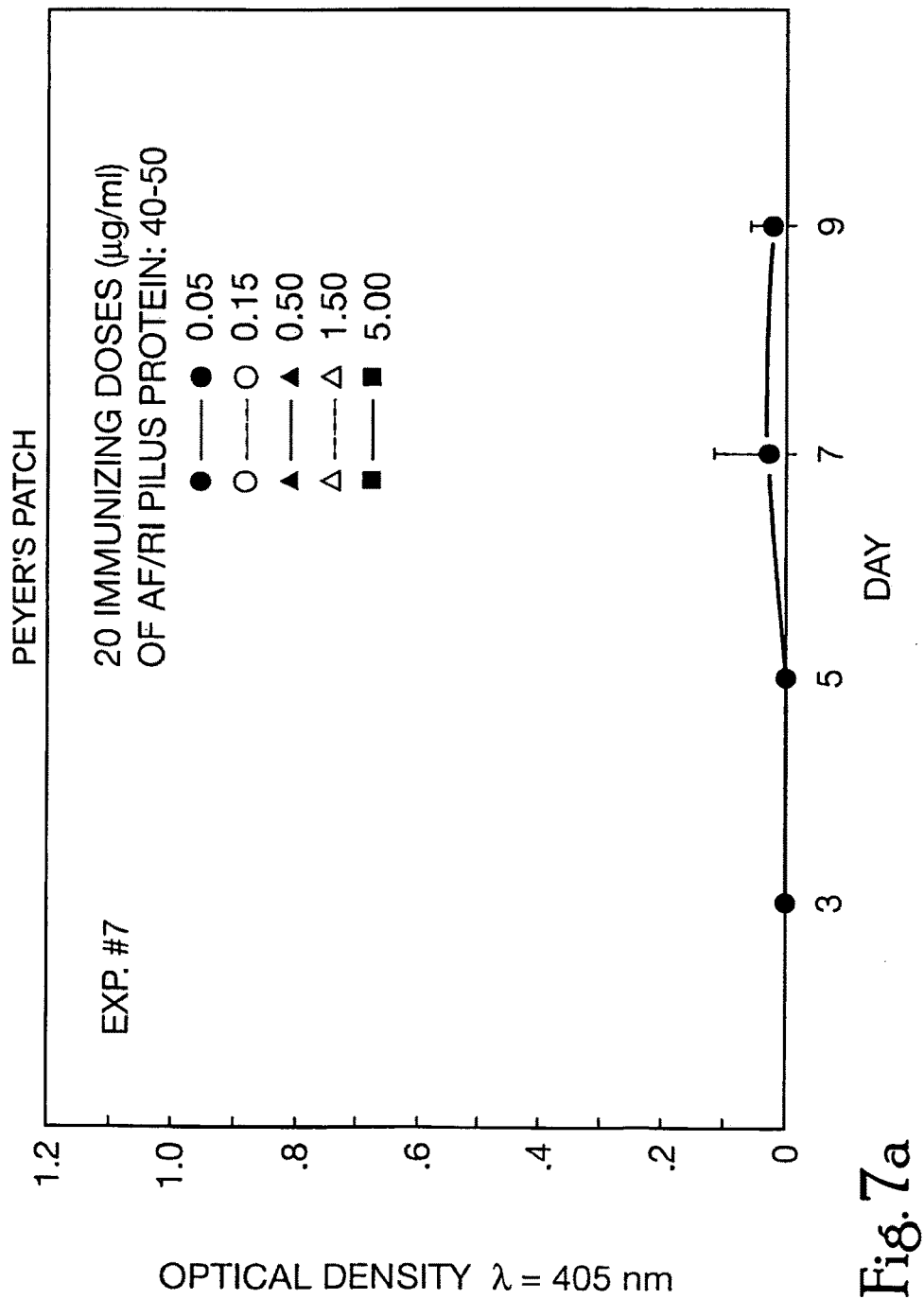
Figure 7B:
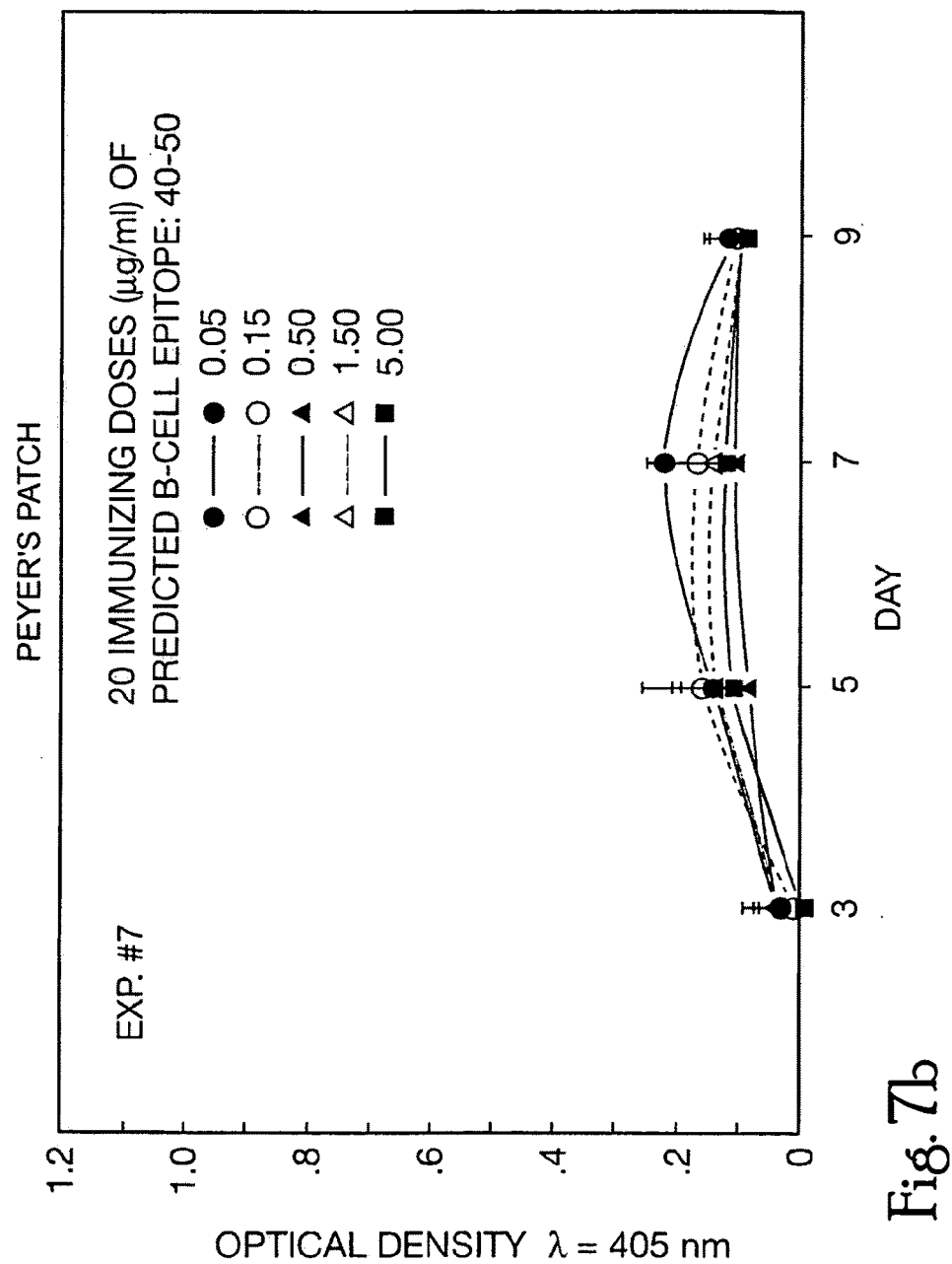
Figure 7C:
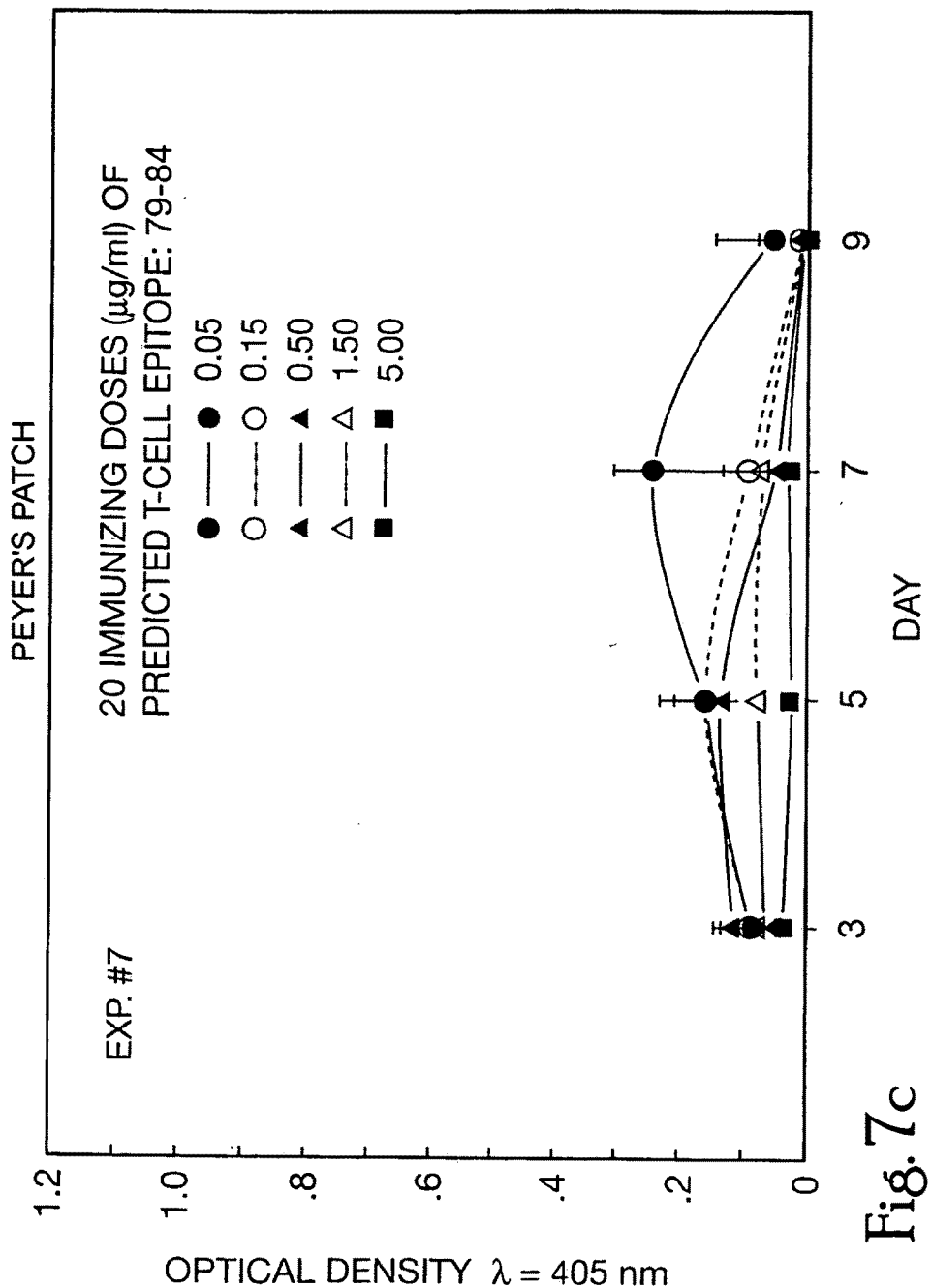
Figure 7D:
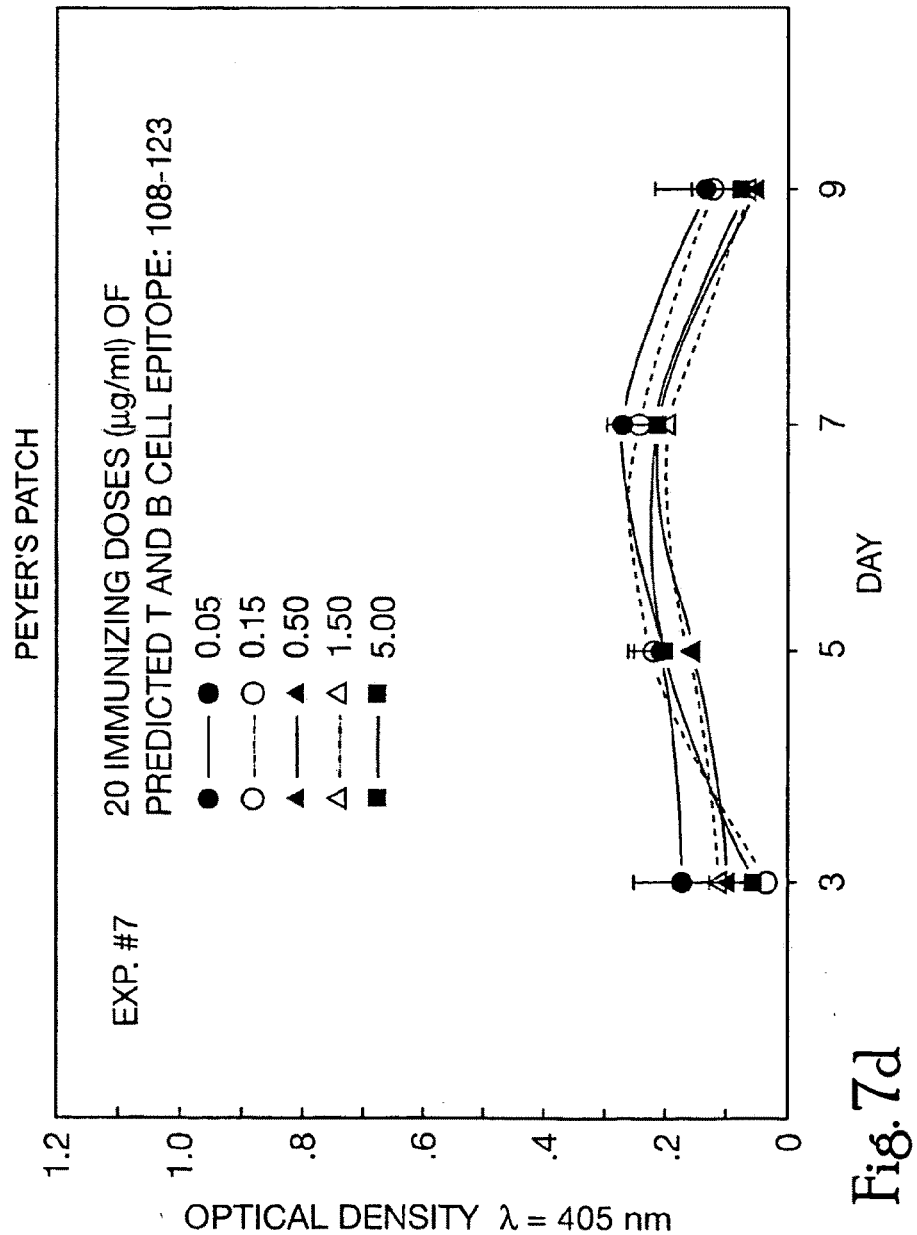
Figure 8A:
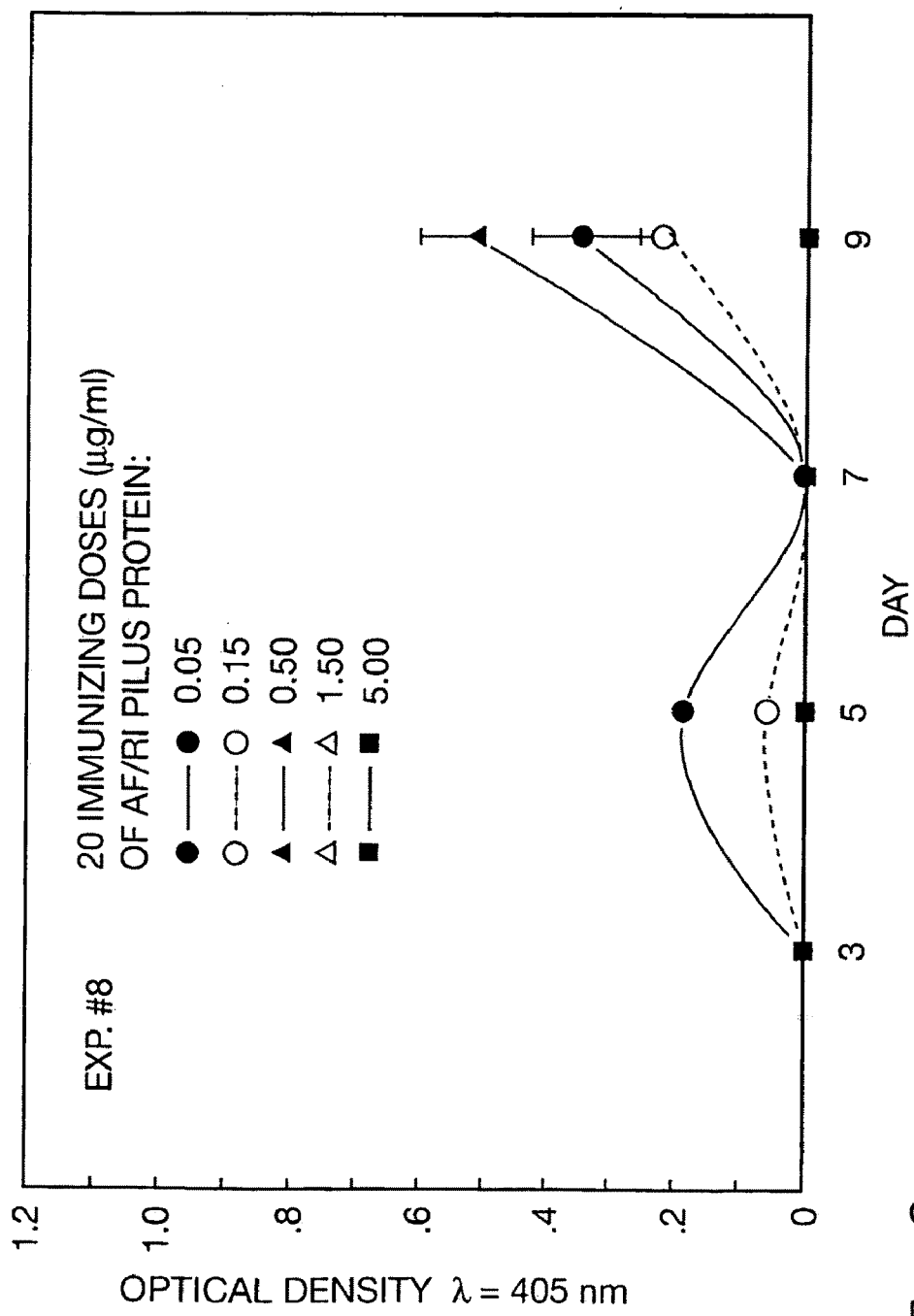
Figure 8B:
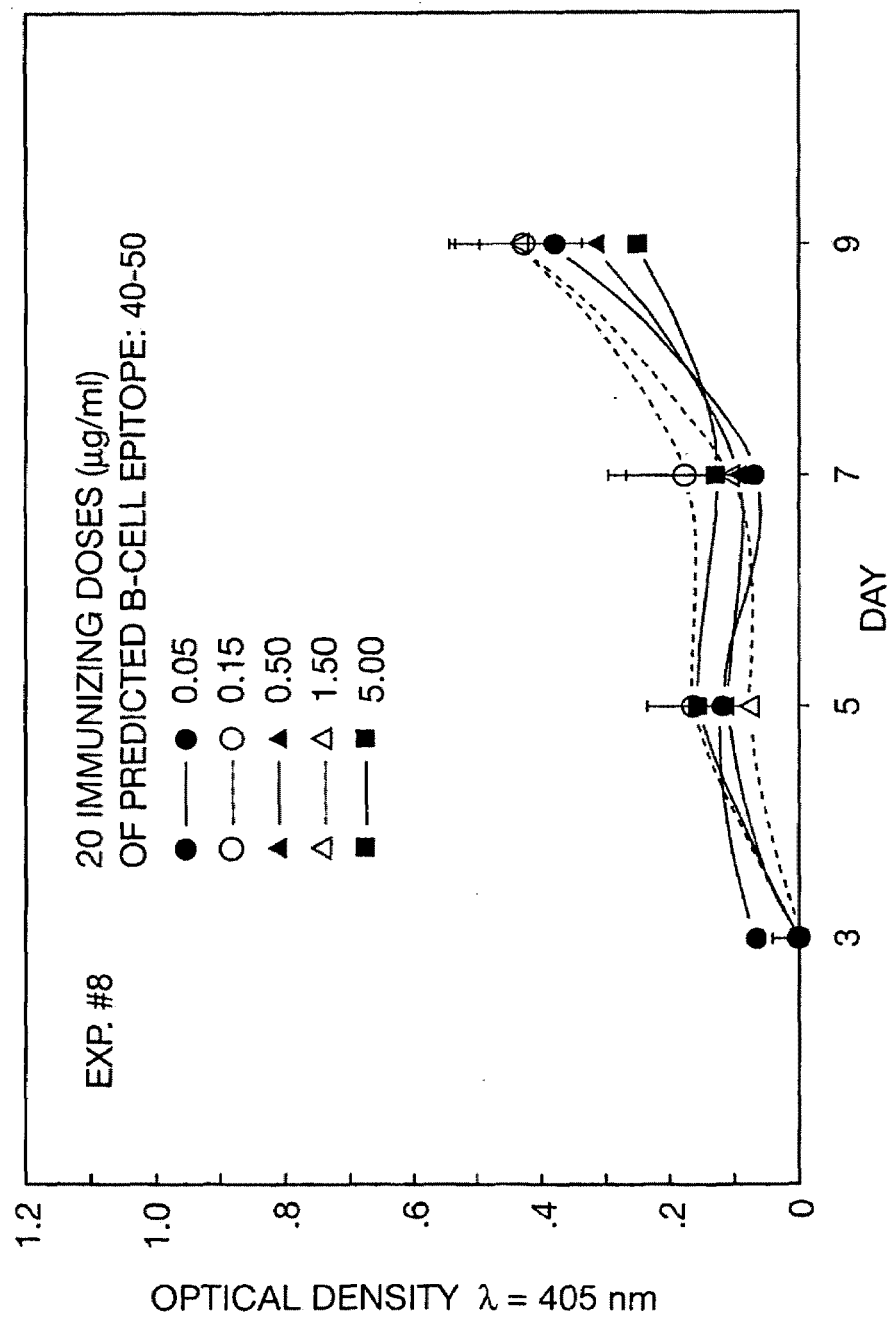
Figure 8C:
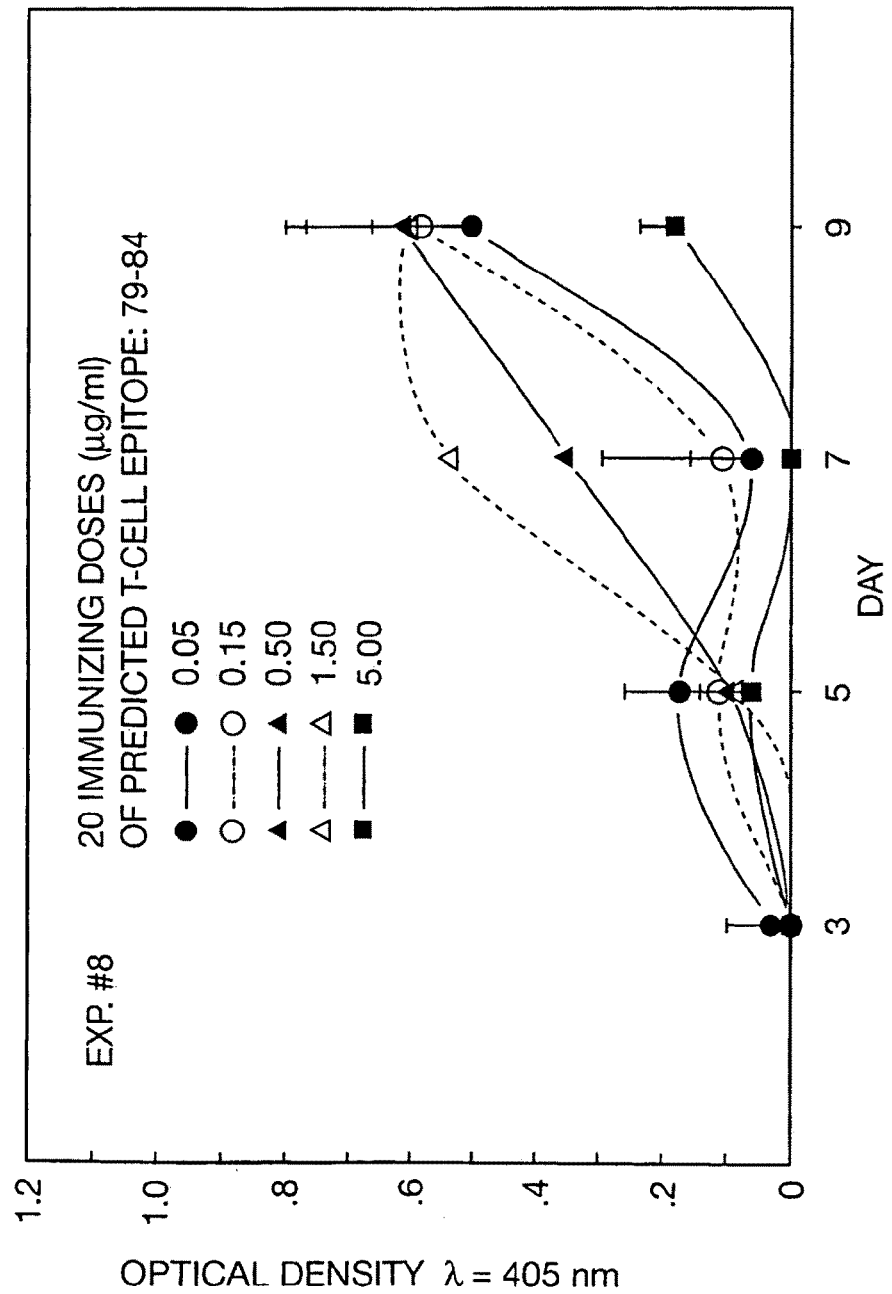
Figure 8D:
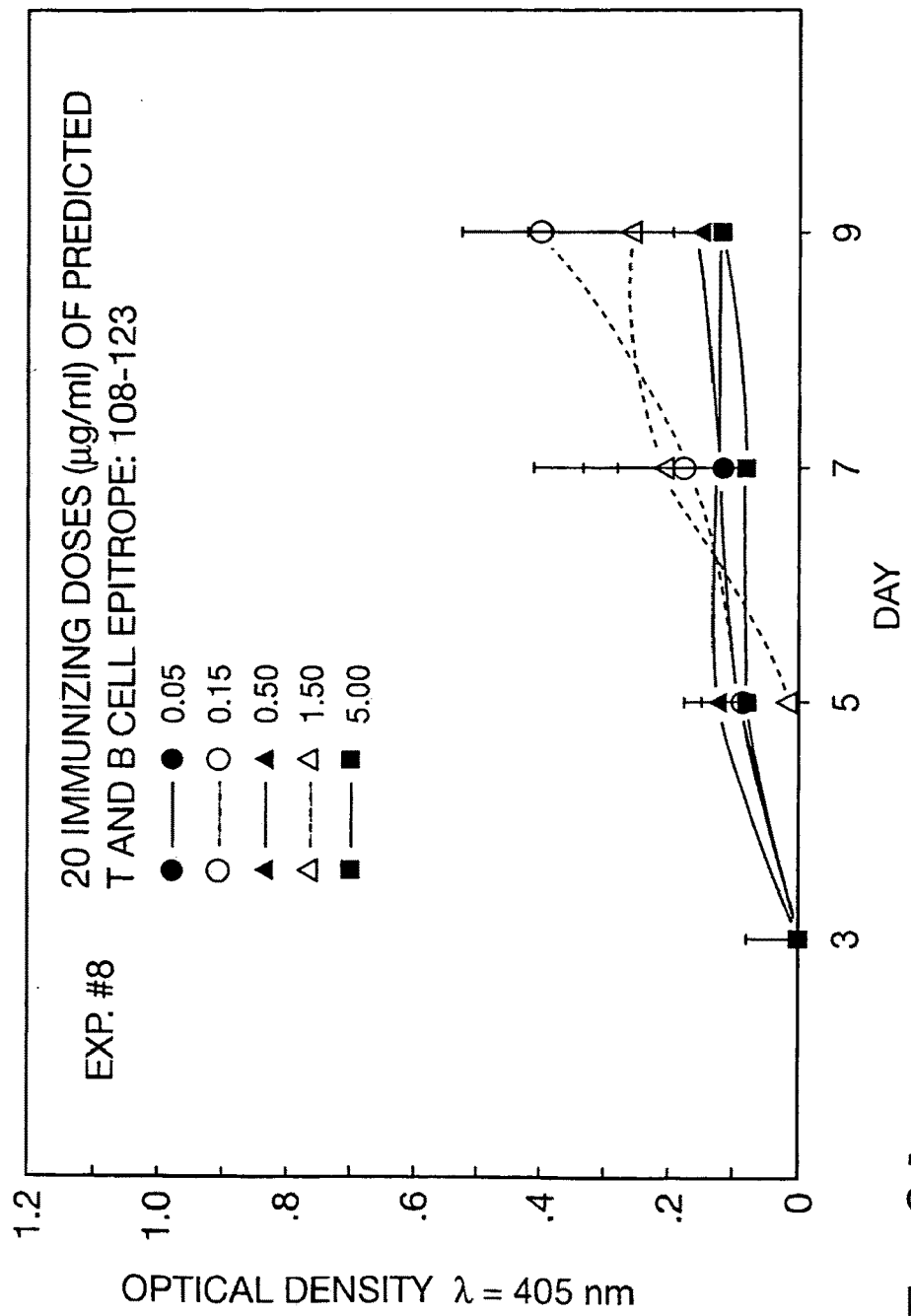
Figure 9A:
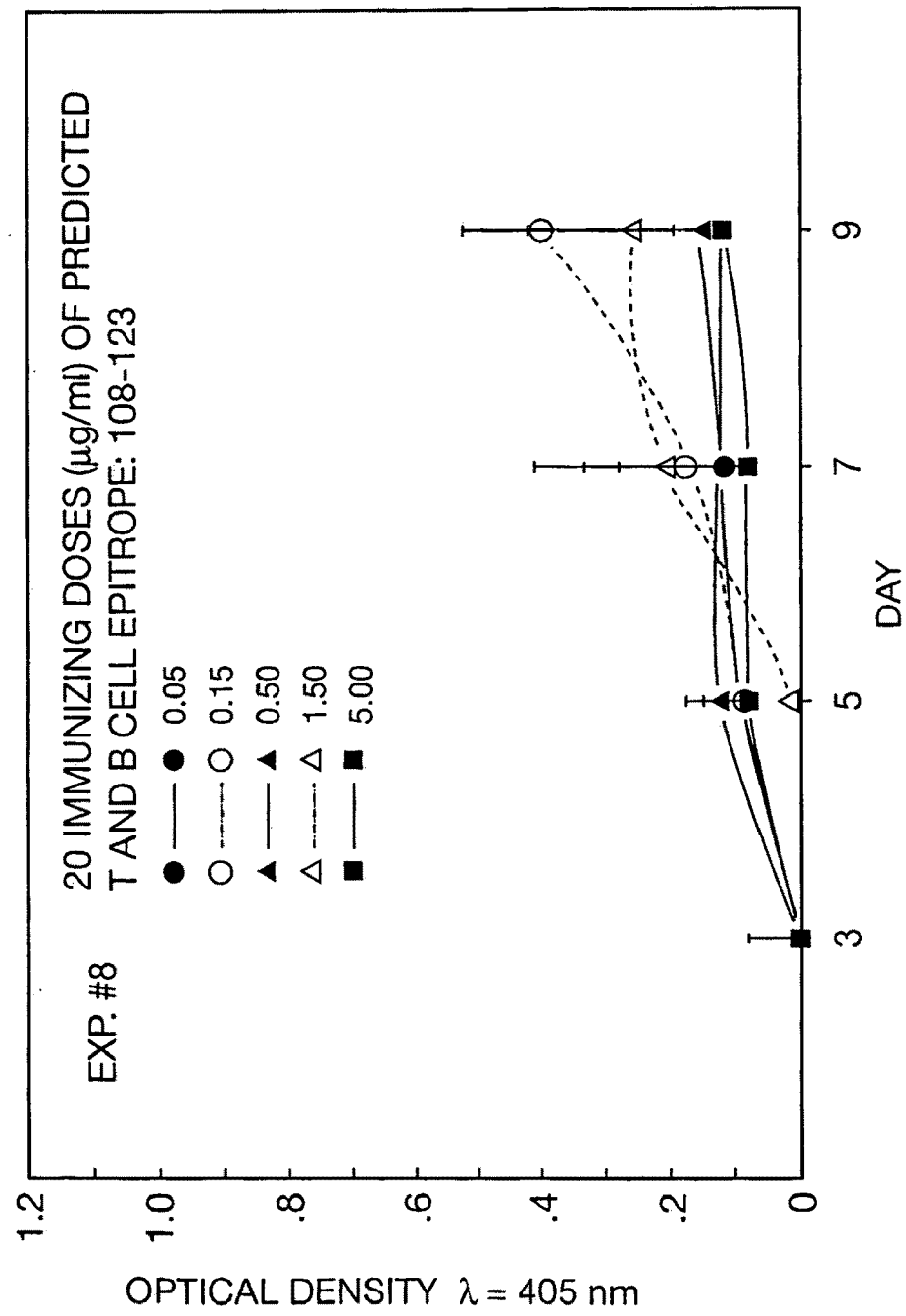
Figure 9B:
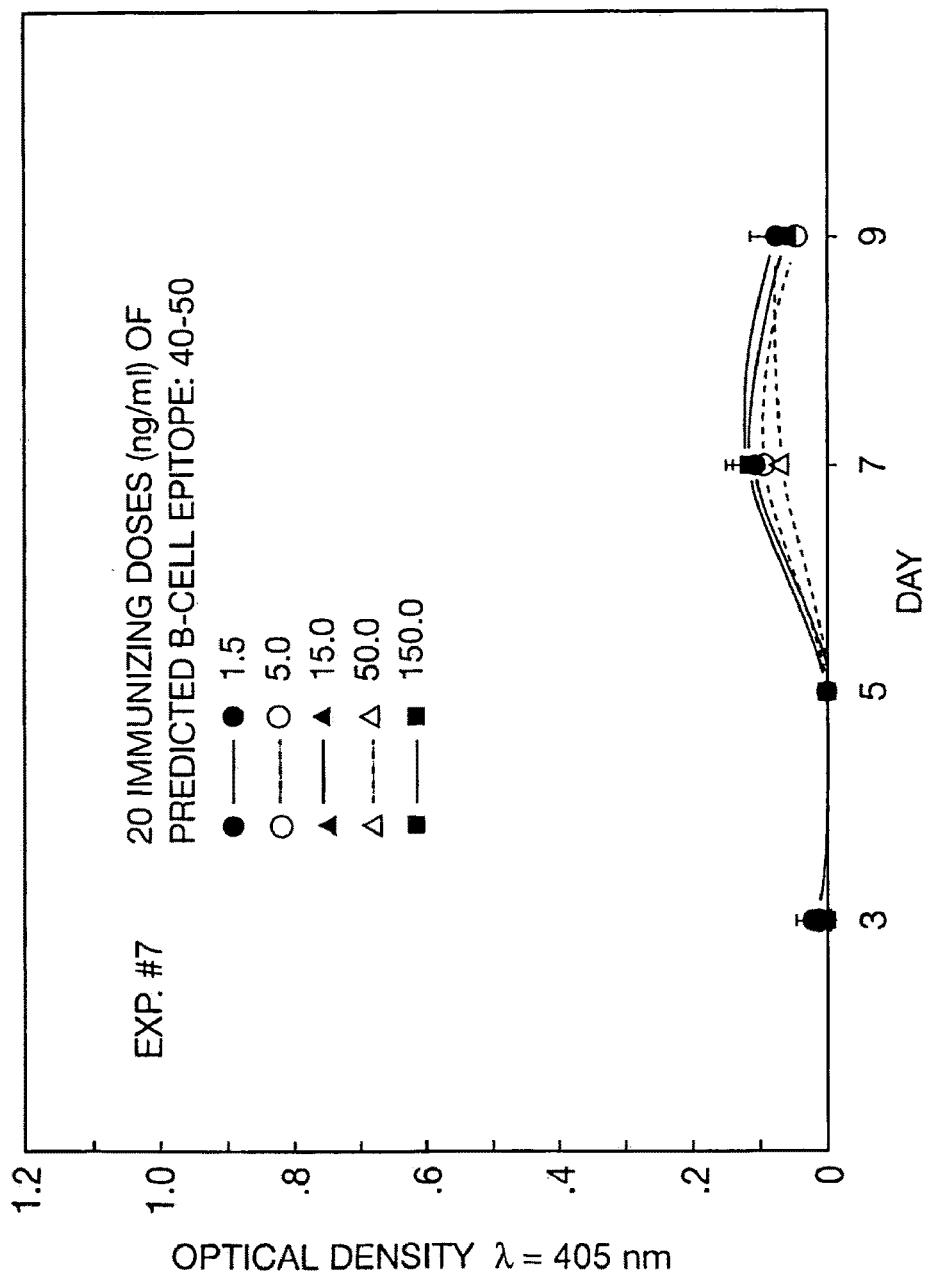
Figure 9C:
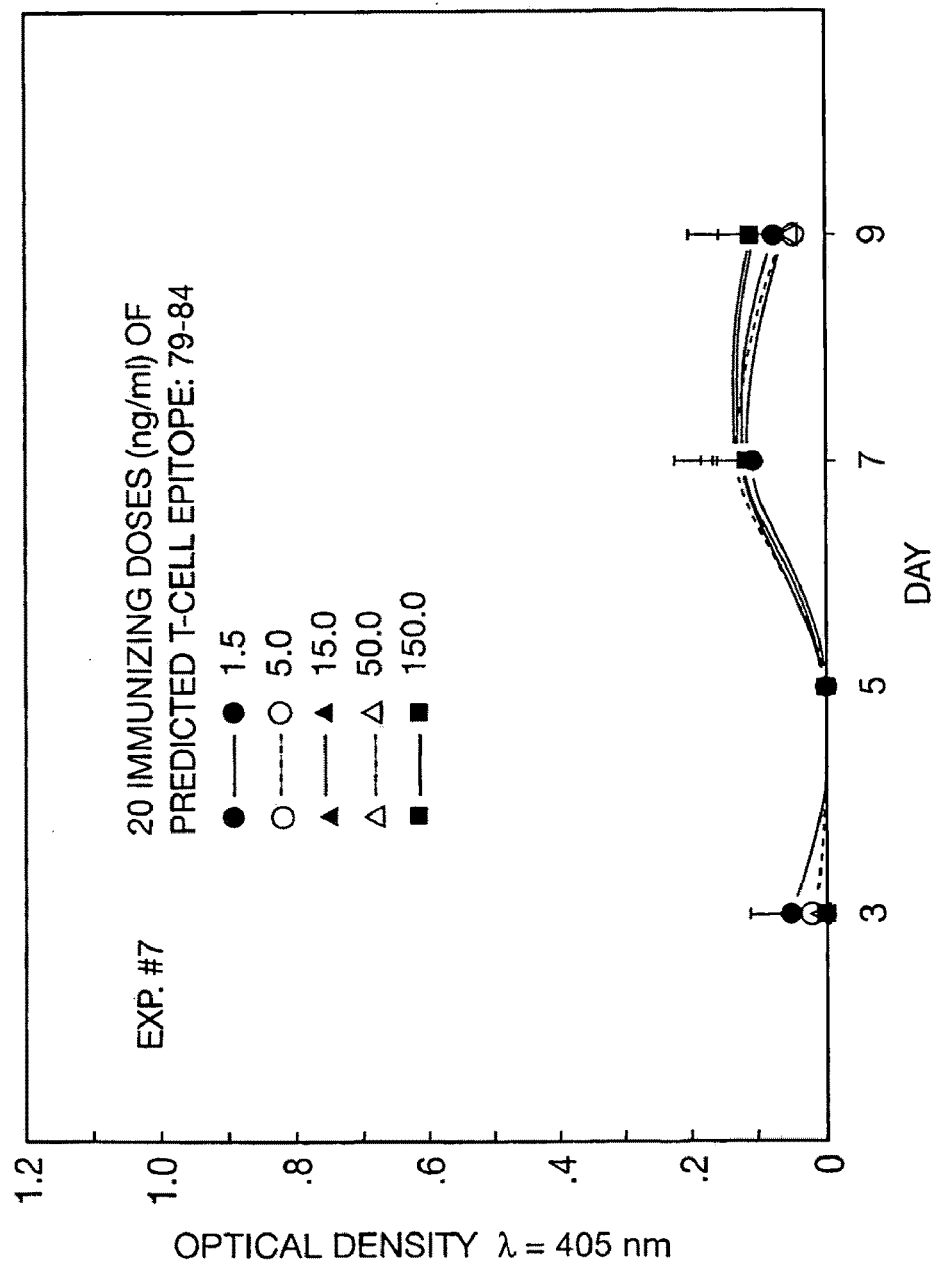
Figure 9D:
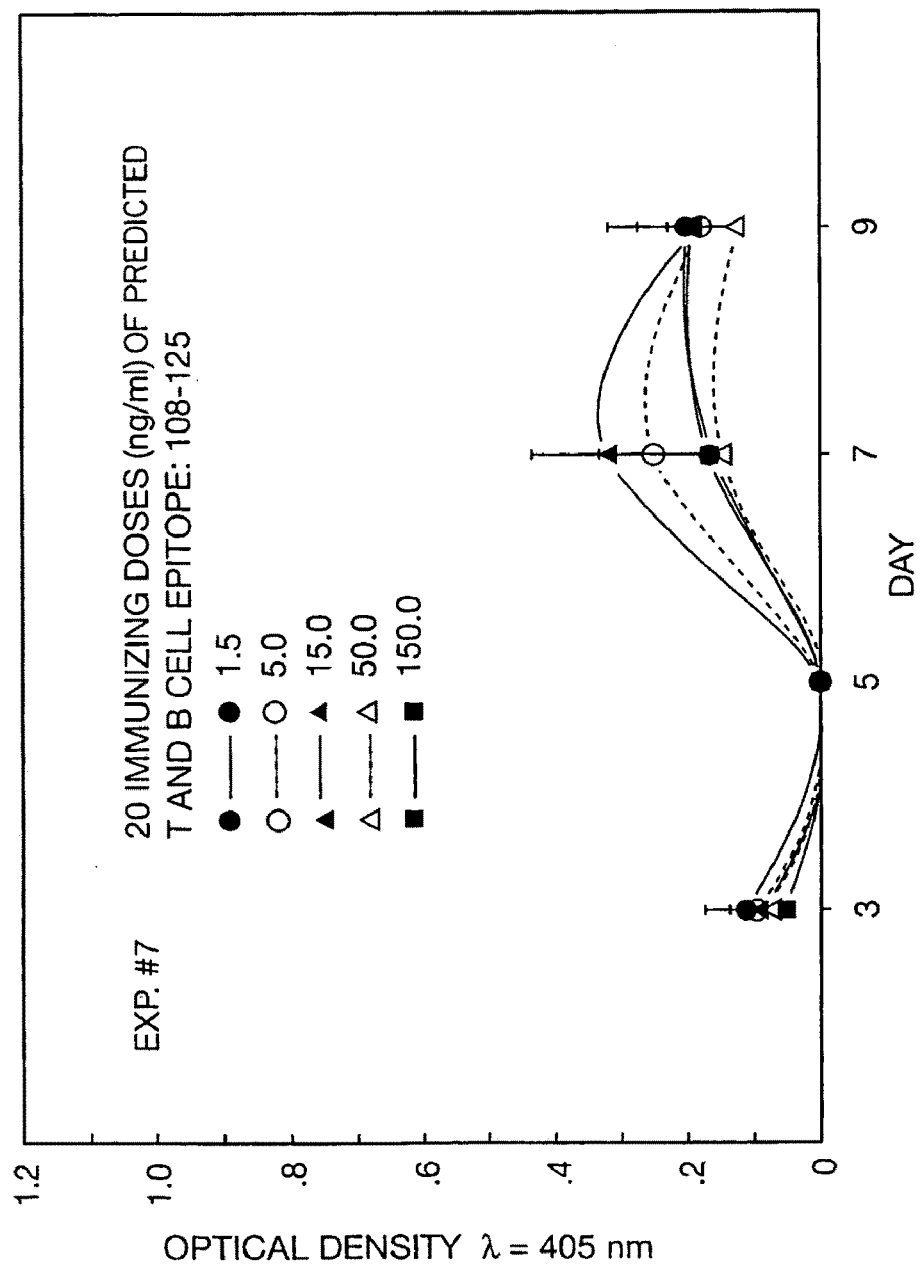

Microencapsulation of AF/R1 potentiates the mucosal cellular immune response. To evaluate the effect that microencapsulation of AF/R1 may have on the cellular mucosal immune response to that antigen, naive rabbits were primed twice with 50 micrograms of either microencapsulated or non-encapsulated AF/R1 by endoscopic intraduodenal inoculation seven days apart. All rabbits were monitored daily and showed no evidence of clinical-illness or colonization by RDEC-1. One week following the last priming, the rabbits were sacrificed and lymphoid tissues were cultured in the presence of AF/R1 pili or peptide antigens. In rabbits which had received non-encapsulated AF/R1, Peyer's Patch cells demonstrated a low level but significant proliferation in vitro in response to AF/R1 pili (FIG. 5), but not to any of the AF/R1 synthetic peptides (FIGS. 6a-6d). However, in rabbits which had received microencapsulated AF/R1, Peyer's Patch cells demonstrated a markedly enhanced response not only to AF/R1 (FIG. 5), but now responded to the AF/R1 synthetic peptides 40-55 and 79-94 (FIGS. 6a and 6b). In addition, one of two rabbits primed with microencapsulated AF/R1 (rabbit 135) responded to AF/R1 108-123, but not AF/R1 40-47/79-86 (FIGS. 6c and 6d). In contrast, the other rabbit in the group (rabbit 134) responded to AF/R1 40-47/79-86, but not to AF/R1 108-123 (FIGS. 6d and 6c).

Figure 15:
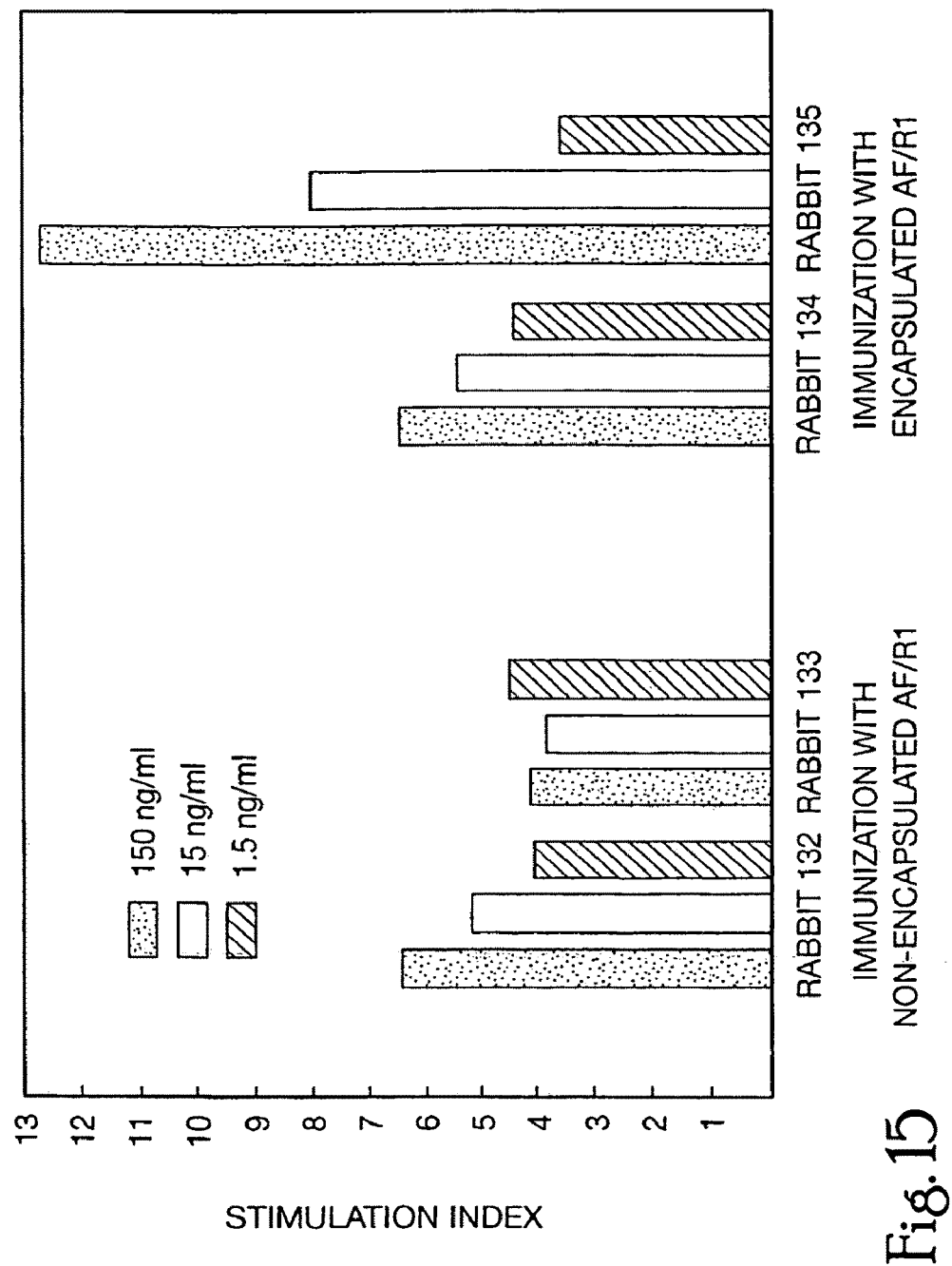
FIG. 15 is a graph showing proliferation of rabbit MLN cells in vitro in response to AF/R1 pili.

Response of MLN cells to the antigens of AF/R1. Studies have shown that cells undergoing blastogenesis in the MLN also tend to home into mucosal areas, but experiments requiring in vitro lymphocyte proliferation of rabbit MLN cells are difficult to conduct and to interpret due to non-specific high background cpm in the media controls. Our studies have shown that this problem can be avoided by conducting the proliferative studies in 24-well plates, and then moving aliquots of cells into 96-well plates for pulsing with [$^3$H]thymidine as described in materials and methods. This method of culture was employed for the remainder of the studies. The MLN cells of all rabbits demonstrated a significant proliferation in vitro in response to AF/R1 pili regardless of whether they had been immunized with microencapsulated or non-encapsulated AF/R1 (FIG. 15). However, only the rabbits which had received microencapsulated AF/R1 were able to respond to the AF/R1 synthetic peptide 40-55 (FIG. 11). The MLN cells of rabbit 134 also responded to AF/R1 79-94 ($p<0.0001$), AF/R1 108-123 ($p<0.0001$), and AF/R1 40-47/79-86 ($p=0.0004$); however, none of the other rabbits demonstrated a MLN response to those three peptides (data not shown).

Figure 12:
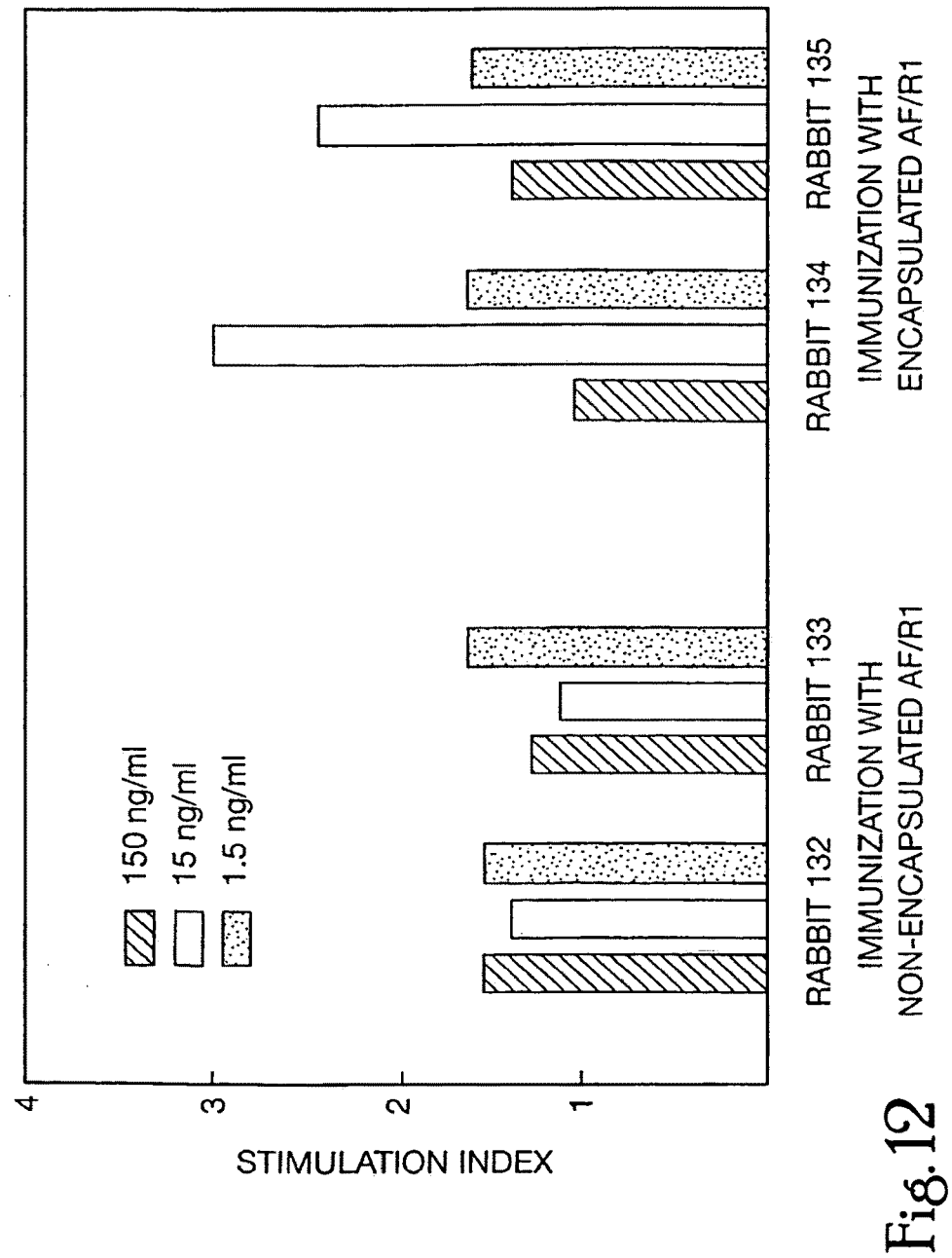

Response of spleen cells to the antigens of AF/R1. Proliferative responses of spleen cells to AF/R1 were very weak in all animals tested (data not shown). However, in results which paralleled the responses in MLN cells, there was a significant response to AF/R1 40-55 in rabbits which had been primed with microencapsulated AF/R1 (FIG. 12). There was no response to the other AF/R1 synthetic peptides by spleen cells in either group of animals. The weak response of spleen cells to AF/R1 provides further evidence that these animals were naive to AF/R1 before the study began, and indicates that the observed responses were not due to non-specific stimulative factors such as lipopolysaccharide.

XI. SUMMARY

We have shown that there is an enhanced in vitro proliferative response to both protein and its peptide antigens by rabbit Peyer's patch cells following intraduodenal inoculation of antigen which had been homogeneously dispersed into the polymeric matrix of biodegradable, biocompatible microspheres. The immunopotentiating effect of encapsulating purified AF/R1 pili as a mucosal delivery system may be explained by one or more of the following mechanisms: (a) Microencapsulation may help to protect the antigen from degradation by digestive enzymes in the intestinal lumen. (b) Microencapsulation has been found to effectively enhance the delivery of a high concentration of antigen specifically into the Peyer's patch. (c) Once inside the Peyer's patch, microencapsulation appears to facilitate the rapid phagocytosis of the antigen by macrophages, and the microspheres which are 5-10 micrometers become localized within the Peyer's patch. (d) Microencapsulation of the antigen may improve the efficiency of antigen presentation by decreasing the amount of enzymatic degradation that takes place inside the macrophage before the epitopes are protected by combining with Class II major histocompatibility complex (MHC) molecules. (e) The slow, controlled-release of antigen may produce a depot effect that mimics the retention of antigen by the follicular dendritic cell. (f) If the antigen of interest is soluble, microencapsulation changes the antigen into a particulate form which appears to assist in producing an IgA B cell response by shifting the cellular immune response towards the $T_H$ and thereby not encouraging a response by the $T_S$. There is evidence that the GALT may be able to discriminate between microbial and non-microbial (food) antigens in part by the form of the antigen when it is first encountered, and thus bacterial antigens do not necessarily have special antigenic characteristics that make them different from food antigens, but they are antigenic because of the bacterial context in which they are presented. The particulate nature of microspheres may serve to mimic that context. It may be important to note that we also observed a significant response to AF/R1 in animals inoculated with non-encapsulated pili; thus, some of this antigen which was still in its native form was able to enter the Peyer's patch. This may be explained by the fact that AF/R1 is known to mediate the attachment of RDEC-1 to the Peyer's patch M-cell. If the antigen employed in this type of study was not able to attach to micrometer M-cells, one would expect to see an even greater difference in the responses of animals which had received microencapsulated versus non-encapsulated antigen.

The microspheres used in these experiments included a size range from 1 to 12 micrometers. The 1 to 5 micrometer particles have been shown to disseminate to the MLN and spleen within migrating macrophages; thus, the observed proliferative responses by cells from the MLN and spleen may reflect priming of MLN or splenic lymphocytes by antigen-presenting/accessory cells which have phagocytosed 1 to 5 micrometer antigen-laden microspheres in the Peyer's patch and then disseminated onto the MLN. Alternatively, these responses may be a result of the normal migration of antigen stimulated lymphocytes that occurs from the Peyer's patch to the MLN and on into the general circulation before homing to mucosal sites. Proliferative responses by MLN cells are of interest because it has been shown that cells undergoing blastogenesis in the MLN tend to migrate onto mucosal areas. However, studies involving in vitro lymphocyte proliferation of rabbit MLN cells can be very difficult to conduct and to interpret due to non-specific high background cpm in the media controls. By simultaneously conducting experiments using different protocols, we have found that this problem can be prevented by avoiding the use of fetal calf serum in the culture and by initially plating the cells in 24-well plates. Using this method, the blasting lymphocytes are easily transferred to a 96-well plate where they receive the [$^3$H]thymidine, while fibroblasts and other adherent cells remain behind and thus do not inflate the background cpm.

The proliferative response to the peptide antigens was of particular interest in these studies. The rabbits that received non-encapsulated AF/R1 failed to respond to any of the peptides tested either at the level of the Peyer's patch, the MLN, or the spleen. In contrast, Peyer's patch-cells from the animals that received microencapsulated AF/R1 responded to all the peptides tested with two exceptions: Rabbit 134 did not respond to AF/R1 108-123, and rabbit 135 did not respond to AF/R1 40-47/79-86. The reason for these non-responses is not clear, but it probably is not due to MHC restrictions as evidenced by the fact that rabbit 134 was able to respond to AF/R1 108-123 at the level of the MLN. The non-responses may be due to varying kinetics of sensitized T cell migration in different rabbits, or they may reflect differences in the efficiency of antigen presentation by cells from different lymphoid tissues of these animals. Of all the synthetic peptides tested, only AF/R1 40-55, (the one selected as a probable B cell epitope), was recognized by serum from an AF/R1 hyperimmune rabbit. In addition, this peptide was the only one that was uniformly recognized by Peyer's patch, MLN, and spleen cells from both rabbit. In addition, this peptide was the only one that was uniformly recognized by Peyer's patch, MLN, and spleen cells from both rabbits that were immunized with microencapsulated AF/R1. The recognition by anti-AF/R1 serum antibodies indicates that the amino acid sequence of this peptide includes an immunodominant B cell epitope. Thus AF/R1 40-55 may readily bind to antigen-specific B cells thereby leading to an efficient B cell presentation of this antigen to sensitized T cells. Even though AF/R1 40-55 was not selected as a probable T cell epitope by either the Rothbard or Berzofsky methods, the current study clearly indicates that this peptide can also stimulate a proliferative immune response. Although further studies are required to definitively show that the proliferating cells are indeed T cells, the responses observed in this study are most likely due to the blast transformation of cells from the lineage. Therefore, AF/R1 40-55 appears to contain a T cell epitope in addition to the immunodominant B cell epitope, and this area of the AF/R1 protein may thereby play an important role in the overall immune response and subsequent protection against RDEC-1.

The proliferative responses of spleen cells was low in all animals tested; however, we feel that this may be simply a matter of the kinetics of cellular migration. The rabbits in this study were sacrificed only two weeks after their first exposure to antigen. This relatively short time period may not have provided sufficient time for cells that were produced by Peyer's patch and MLN blasts to have migrated as far as the spleen in sufficient numbers.

An ideal mucosal vaccine preparation would not only assist in the uptake and presentation of the immunogen of interest, but it would also be effective without requiring carrier molecules or adjuvants which may complicate vaccine production or delay regulatory approval. The incorporation of antigen into microspheres appears to provide an ideal mucosal delivery system for oral vaccine immunogens because the observed immunopotentiating effect is achieved without the need for carriers of adjuvants. This ability may prove to be of great value, particularly to enhance the delivery of oral synthetic peptide vaccines to the GALT.

TABLE 1

Linear B-Cell Epitopes of CFA/I in Monkeys

| Sequence Position | Individuals Responding | Consensus Site |
|---|---|---|
| 1. 11-21 | 3 | (SEQ ID NO: 30) VDPVIDLLQ |
| 2. 93-101 | 2 | (SEQ ID NO: 19) AKEFEAAA |
| 3. 124-136 | 2 | (SEQ ID NO: 31) GPAPT |
| 4. 66-74 | 2 | (SEQ ID NO: 32) PQLTDVLN |
| 5. 22-29 | 2 | (SEQ ID NO: 14) GNALPSAV |

TABLE 1-continued

Linear B-Cell Epitopes of CFA/I in Monkeys

| Sequence Position | Individuals Responding | Consensus Site |
|---|---|---|
| 6. 32-40 | 1 | KTF* |
| 7. 38-45 | 1 | |
| 8. 3-11 | 1 | |

*Overlap between epitope 6 and 7

TABLE 2

Prediction of T cell epitopes within the CFA/I molecule[a]

| Predicted Amphipathic Segments | | |
|---|---|---|
| 7 aa blocks | 11 aa blocks | Rothbard Criteria |
| 22-25 | 8-11 | 16 |
| 34-38 | 32-44 | 30 |
| 40-46 | 51-71 | 38 |
| 50-53 | 86-92 | 44 |
| 56-62 | 102-108 | 57 |
| 64-71 | 130-131 | 61 |
| 104-108 | 135-137 | 70 |
| 131-137 | | 116 |
| | | 124 |
| | | 127 |
| | | 137 |

[a]The sequence numbers of the first amino acid of the predicted T cell epitopes are shown. Software designed to predict T cell epitopes based on the Berzofsky method was published as the AMPHI program. It predicts amphipathic amino acid segments by evaluating 7 or 11 residues as a block and assigning a score to the middle residue of that block. Software designed to predict T cell epitopes based on the Rothbard method was written by Stephen Van Albert (The Walter Reed Army Institute of Research, Washington, D.C.).

TABLE 3

Amino acid sequence of immunodominant T cell epitopes[a]

| Residue Numbers | Amino Acids |
|---|---|
| 8-17 | (SEQ ID NO: 2) Thr Ala Ser Val Asp Pro Val Ile Asp Leu |
| 40-49 | (SEQ ID NO: 33) Phe Glu Ser Tyr Arg Val Met Thr Gln Val |
| 72-81 | (SEQ ID NO: 7) Leu Asn Ser Thr Val Gln Met Pro Ile Ser |
| 134-143 | (SEQ ID NO: 34) Asn Tyr Ser Gly Val Val Ser Leu Val Met |

[a]Of the 19 decepeptides that supported a significant proliferative response and contained a serine at either position 2, 3, or 4, nine has a serine specifically at position 3. Some of the most robust responses were to the peptides that contained a serine residue at the third position. The amino acid sequence of four such decapeptides which are believed to be immunodominant T cell epitopes is shown.

FIGS. 11 and 12 serve to illustrate that inclusion of *Escherichia coli* pilus antigen in microspheres enhances cellular immunogenicity.

A primary mucosal immune response, characterized by antipilus IgA, follows infection of rabbits with *E. coli* RDEC-1. However, induction of an optimal primary mucosal response by enteral vaccination with pilus antigen depends on immunogenicity of pilus protein, as well as such factors as its ability to survive gastrointestinal tract (GI) transit and to target immunoresponsive tissue. We tested the effect of incorporating AF/R1 pilus antigen into resorbable microspheres upon its ability to induce primary mucosal and systemic antibody responses after direct inoculation into the GI tract. METHODS: rabbits were inoculated with 50 micrograms of AF/R1 pilus antigen alone or incorporated into uniformly sized (5-10 microns) resorbably microspheres (MIC) of poly (DL-lactide-coglycolide). Inoculation was by intra-duodenal (ID) intubation via endoscopy or directly into the ileum near a Peyer's patch via the RITARD procedure (with the cecum ligated to enhance recovery of gut secretions and a reversible ileal tie to slow antigen clearance). ID rabbits were sacrificed at 2 weeks for collection of gut washes and serum. RITARD rabbits were bled and purged weekly for 3 weeks with Co-lyte to obtain gut secretions. Anti-pilus IgA and IgG were measured by ELISA.

TABLE 1

|  | RITARD-PILI | RITARD-MIC | ID-PILI | ID-MIC |
|---|---|---|---|---|
| Anti-pilus IgA (fluid) | *7/8 | 4/8 | 1/2 | 0/3 |
| Anti-pilus IgG (serum) | 0/8 | 3/8 | 0/2 | 1/3 |

RESULTS:
*pos/test

Native pilus antigen led to a mucosal IgA response in 7/8 RITARD rabbits. MIC caused a similar response in only 4/8, but the groups were not statistically different. MIC (but not pili) induced some systemic IgG responses (highest in animals without mucosal responses). Results in rabbits inoculated ID were similar for pili, but no mucosal response to ID-MIC was noted. SUMMARY: Inoculation with pilus antigen produces a primary mucosal IgA response. Microencapsulation does not enhance this response, although the antigen remains immunogenic as shown by measurable mucosal and some strong serum responses. It must be determined whether priming with antigen in microspheres can enhance secondary responses.

B Cell Epitope Data

Materials and Methods

CFA/I PURIFICATION—INTACT CFA/I pili were purified from H10407 (078:H-) as described by Hall et al, (1989) [20]. Briefly, bacteria grown on colonization factor antigen agar were subjected to shearing, with the shearate subjected to differential centrifugation and isopycnic banding on cesium chloride in the presence of N-lauryl sarkosine. CFA/I were dissociated to free subunits in 6M guanididinium HCl, 0.2 M ammonium bicarbonate (2 hr, 25°), passed through an ultrafiltration membrane (Amicon XM 50 stirred cell, Danvers, Mass.), with concentration and buffer exchange to PBS on a YM 10 stirred cell (Amicon). Examination of dissociated pili by electron microscopy demonstrated a lack of pilus structure.

Protein Sequencing—The primary structure of CFA/I has been determined by protein sequencing techniques (Klemm, 1982) and through molecular cloning methods (Karjalainen, et al 1989) [21]. In these two studies there was agreement in all but two of the 147 amino acid residues (at positions 53 and 74). To resolve the apparent discrepancies, CFA/I was enzymatically digested in order to obtain internal amino acid sequence. Trypsin or *S. aureus* V8 protease (sequencing grade, Boehringer Mannheim) was incubated with CFA/I at a 1:50 w:w ratio (Tris 50 mM, 0.1% SDS, pH 8.5 for 16 h at 37° (trypsin) or 24° C. (V8)). Digested material was loaded onto precast 16% tricine SDS-PAGE gels (Schagger and von Jagow, 1987) (Novex, Encinitis, Calif.) and run following manufacturers instructions. Separated samples were electrophoretically transferred to PVDF membranes (Westrans, Schleicher and Schuell, Keene, N.H.) following Matsiduria (1987) using the Novex miniblot apparatus. Blotted proteins were stained with Rapid Coomassie stain (Diversified Biotech, Newton Centre, Mass.). To obtain the desired fragment containing the residue of interest within a region accessible by automated gas phase sequencing techniques, molecular weights were estimated from standards of molecular weights 20,400 to 2,512 (trypsin inhibitor, myoglobin, and myoglobin cyanogen bromide fragments; Diversified Biotech) using the corrected molecular weights for the myoglobin fragments as given in Kratzin et al., (1989) [22]. The estimated molecular weights for the unknown CFA/I fragments were compared to calculated molecular weights of fragments as predicted for CFA/I from the sequence of CFA/I as analysed by the PEPTIDESORT program of a package developed by the University of Wisconsin Genetics Computer Group. Selected fragments were cut from the PVDF emebrane and subjected to gas phase sequencing (Applied Biosystem 470, Foster City, Calif.).

Monkey Immunization—Three rhesus monkeys (*Macaca mulatta*) were injected intramuscularly with 250 ug of dissociated CFA/I in complete Freund's adjuvant and subsequently with two injections of 250 ug of antigen in incomplete Freund's adjuvant at weekly intervals. Blood was drawn three weeks after primary immunization.

Peptide Synthesis—Continuous overlapping octapeptides spanning the entire sequence CFA/I were synthesized onto polyethylene pins by the method of Geysen et al. [16], also known as the PEPSCAN procedure. Derivitized pins and software were purchased from Cambridge Research Biochemicals (Valley Stream, N.Y.). Fmoc-amino acid pentafluorophenyl esters were purchased from Peninsular Laboratories (Belmont, Calif.) 1-hydroxybenzotriazole monohydrate (HYBT) was purchased from Aldrich, and reagent grade solvents from Fisher. To span the entire sequence of CFA/I with a single amino acid overlap of from one peptide to the next, 140 total pins were necessary, with a second complete set of 140 pins synthesized simultaneously.

ELISA procedure—Sera raised in monkeys to purified dissociated pili were incubated with the pins in the capture ELISA assay of Geysen et al., [16] with the preimmune sera of the same animal tested at the same dilution simultaneously with the duplicate set of pins. Dilution of sera used on the pins was chosen by initial titration of sera by standard ELISA assay and immunodot blot assay against the same antigen.

Results

It was essential to utilize the correct sequence of CFA/I in the synthesis of the pins for both T- and B-cell experiments to carry out the studies as planned. At issue were the amino acids at position 53 and 74; incorrect residues at those positions would effect 36 of 138 pins (26%) for T-cell epitope analysis and 30 of 140 pins (21%) for B-cell analysis. To resolve the discrepancy in the literature, purified CFA/I was proteolytically digested separately with trypsin and with *S. aureus* V8 protease (V8). These enzymes were chosen in order to give fragments with the residues of interest (53 and 74) relatively near to the N-terminus for automated Edman degradation (preferably 1-15 residues). These digests were separated on tricine SDS-PAGE gels (FIG. 16A) and molecular masses of fragments estimated. A fragment of 3459 calculated molecular mass is expected from the trypsin digest (corresponding to amino acids 62-94) and a fragment of 5889 calculated molecular mass is expected from the V8 digest (residues 42-95). These fragments were located within each digest (arrows in FIG. 16), and a companion gel with four lanes of each digest was run, electrophoretically transferred to PVDF, the bands excised and sequenced. N-terminal sequences of each fragment are given in FIG. 16B. The N-terminal eighteen residues from the trypsin fragment were determined that corresponded to positions 62-79 in CFA/I. Position 74, a serine residue was consistent with that determined by Karjalainen et al., (Karjalainen et al., 1989). Nineteen residues of the V8 fragment were determined, corresponding to residues 41-60 of the parent protein. The twelfth residue of the fragment contained an aspartic acid, also consistent with Karjalainen et al., (1989). All other residues sequenced were consistent with those published previously (including residues 1-29, not shown). For the following peptide synthesis were therefore utilized the complete amino acid sequence of CFA/I consistent with Karjalainen et al., (1989).

Sera from monkeys immunized with CFA/I subunits were tested in a modified ELISA assay, with the preimmunization sera tested simultaneously with duplicate pins. Assays results are displayed in FIG. 17. Monkey 2Z2 (FIG. 2A) responded strongly to six regions of the CFA/I sequence. Peptide 14 (the octapeptide 14-21) gave the strongest response with four pins adjacent to it (11, 12, 13, and 15) also appearing to bind significant antibody. The other 2Z2 epitopes are centered at peptides 3, 22, 33, 93, and 124. Monkey 184D (FIG. 17B) also responded strongly to peptide 14, although the maximum response was to peptide 13, with strong involvement of peptide 12 in the epitope. Additional epitopes recognized by 184d were centered at peptides 22, 33, 66, and 93. The third monkey serum tested, 34, responded to this region of the CFA/I primary structure, both at peptides 1, 12 and weakly at 14. Two other epitopes were identified by 34, centered at peptides 67 and 128. FIG. 18 illustrates the amino acids corresponding to the epitopes of CFA/I as defined by the response of these three monkeys aligned with the entire primary structure. The entire antigenic determinants are mapped and areas of overlap with other epitopes (consensus sites) are displayed. These epitopes are summarized in Table 1.

T Cell Epitope Data

Materials and Methods

Animals. Three healthy adult *Macaca mulatta* (Rehesus) monkeys (approximately 7 kg each) were used in this study. Their medical records were examined to assure that they had not been in a previous protocol which would preclude their use in this study. Each monkey was sedated with ketamine HCL1 at standard dosage and blood was drawn to obtain preimmune serum.

Antigen. CFA/I pili were purified from *E. coli* strain H107407 (serotype 078:H11) by ammonium sulfate precipitation using the method of Isaacson [17]. The final preparation migrated as a single band on SD-polyacrylamide gel electrophoresis and was shown to be greater than 95% pure by scanning with laser densitometry when stained with coomassie blue. The pili were then dissociated into CFA/I pilin subunits.

Immunization. Each monkey was given 25 mg of purified CFA/I pilin subunits, which had been emulsified in Complete Freund's Adjuvant, by single i.m. injection (0.5 ml). For each animal, the initial dose of antigen was followed by two similar injections in Incomplete Freund's Adjuvant at seven day intervals.

Peptide Antigens. The peptides were synthesized based on the published sequence of CFA/I [18] using the Geysen pin method (Pepscan procedure) [16] with equipment and software purchased from Cambridge Research Biochemicals, Inc. (Wilmington, Del.). Fmoc-amino acid pentafluorophenyl esters were purchased from Peninsula Laboratories (Belmont, Calif.) and used without further treatment or analysis. The activating agent 1-hydroxybenzotriazole monohydrate (HOBT) was purchased from Aldrich Chemical Company (Milwaukee, Wis.). Solvents were reagent grade from Fisher Scientific (Springfield, N.J.).

Two schemes were used to synthesize the peptides. Peptides for the B-cell tests were synthesized as octamers and remained linked to the resin. However, the peptides used to search for T-cell epitopes were synthesized as decamers with an additional Asp-Pro spacer between the pins and the peptides of interest. The Asp-Pro linkage is acid labile allowing cleavage of the decamers from the pins for T-cell proliferation assays [15]. The peptides were cleaved in 70% formic acid for 72 hours at 37 degrees C. The acid solution was removed by evaporation (Speed-Vac, Savant Instruments, Framingdale, N.Y.) followed by rehydration with distilled deionized water and lyophilizaiton. The resulting cleaved peptides were used without further treatment or analysis. The yield was approximately 10 ug per pin, approximately 10 percent on a molar basis of the total amount of proline on each pin as determined by quantitative amino acid analysis.

Residues 12 and 13 on the CFA-1 protein are Asp and Pro, respectively, the same sequence used to cleave the peptides from the pins. Therefore, to prevent truncated peptides from the native sequence during the cleavage process, two substitutions were made for Asp-12. One substitution was a glutamic acid residue for the aspartic acid, a substitution to retain the carboxylic acid functional group. The second substitution was an asparagine residue to conserve the approximate size of the side chain while retaining some hydrophilicity. Each substitution was tested in the T-cell proliferation assay. Both substitutions as well as the native sequence were analyzed by ELISA. For both the T cell and B cell assays, additional sequences not found on the protein were synthesized and used as control peptides.

Lymphocyte proliferation. At day 10-14 following the final inoculation of antigen, the monkeys were again sedated with ketamine HCl, and 50 ml of blood was drawn from the femoral artery for serum preparation. Animals were then euthanized with an overdose of pentothal and spleen was removed. Single cell suspensions were prepared and washed in Dulbecco's modified Eagle medium (Gibco Laboratories, Grand Island, N.Y.) which had been supplemented with penicillin (100 units/ml), streptomycin (100 ug/ml), L-glutamine (2 mM), and HEPES Buffer (10 mM) all obtained from Gibco Laboratories, as well as MEM non-essential amino acid solution (0.1 mM), MEM [50x] amino acids (2%), sodium bicarbonate (0.06%), and $5 \times 10^{-5}$ M 2-ME all obtained from Sigma Chemical Company (St. Louis, Mo.) [cDMEM]. Erythrocytes in the spleen cell suspension were lysed using standard procedures in an ammonium chloride lysing buffer. Cell suspensions were adjusted to $10^7$ cells per ml in cDMM, and autologous serum was added to yield a final concentration of 1.0%. Cells (0.05 ml) were plated in 96-well flat bottom culture plates (Costar; Cambridge, Mass.) along with 0.05 ml of various dilutions of antigen in cDMEM without serum (yielding a 0.5% final concentration of autologous serum) and were incubated at 37 degrees C in 5% $CO_2$. Each peptide was tested at 6.0, 0.6, 0.06 ug/ml. All cultures were pulsed with 1 uci [$^3$H]thymidine (25 Ci/mmol, Amersham, Arlington Hights, Ill.) on day 4 of culture and were harvested for scintillation counting 6 hours later.

ELISA

Epitope prediction. Software designed to predict B cell epitopes based on hydrophilicity, flexibility, and other criteria was developed by the University of Wisconsin Genetics Computer Group [19]. Software designed to predict T cell epitopes based on the Rothbard method [7] was written by Stephen Van Albert (The Walter Reed Army Institute of Research, Washington, D.C.). Software designed to predict T cell epitopes based on the Berzofsky method was published as the AMPHI program [9]. It predicts amphipathic amino acid segments by evaluating 7 or 11 residues as a block and assigning the score to the middle residue of that block.

Statistics. All lymphocyte proliferations were conducted in replicates of four, and standard deviations of the counts per minute (cpm) are shown. Statistical significance (p value) for the proliferative assay was determined using the Student's t test to compare the cpm of quadruplicate wells cultured with the CFA/I peptides to the cpm of wells cultured with a control peptide.

Results

Prediction of T cell epitopes within the CFA/I molecule. To identify possible T cell epitopes within the CFA/I molecule, amphipathic amino acid segments were predicted by evaluating 7 or 11 residues as a block using the AMPHI program [9]. Possible t cell epitopes were also identified using criteria published by Rothbard and Taylor [7]. The sequence numbers of the first amino acid of the predicted segments are shown in Table 1.

Figure 1:
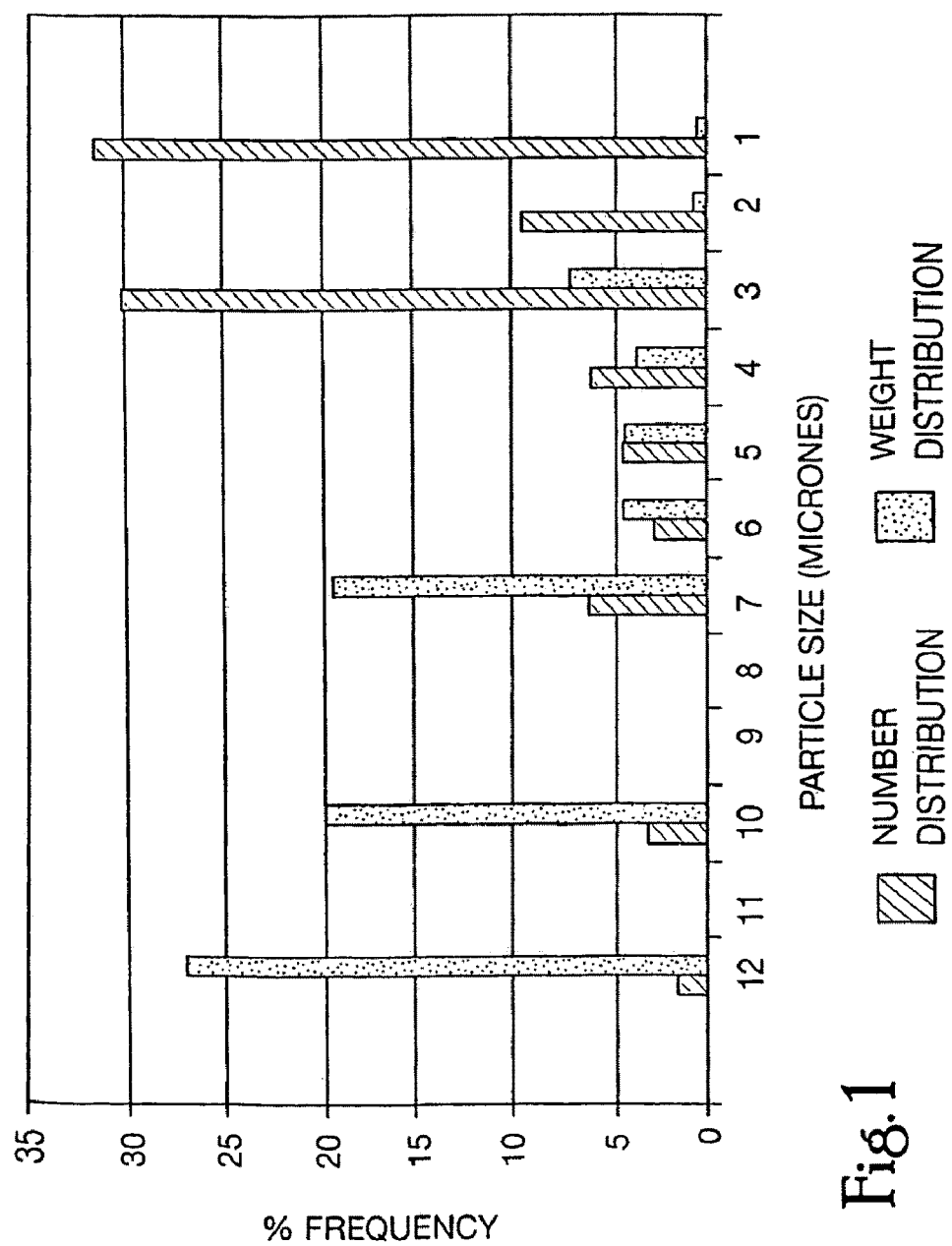
Figure 2:
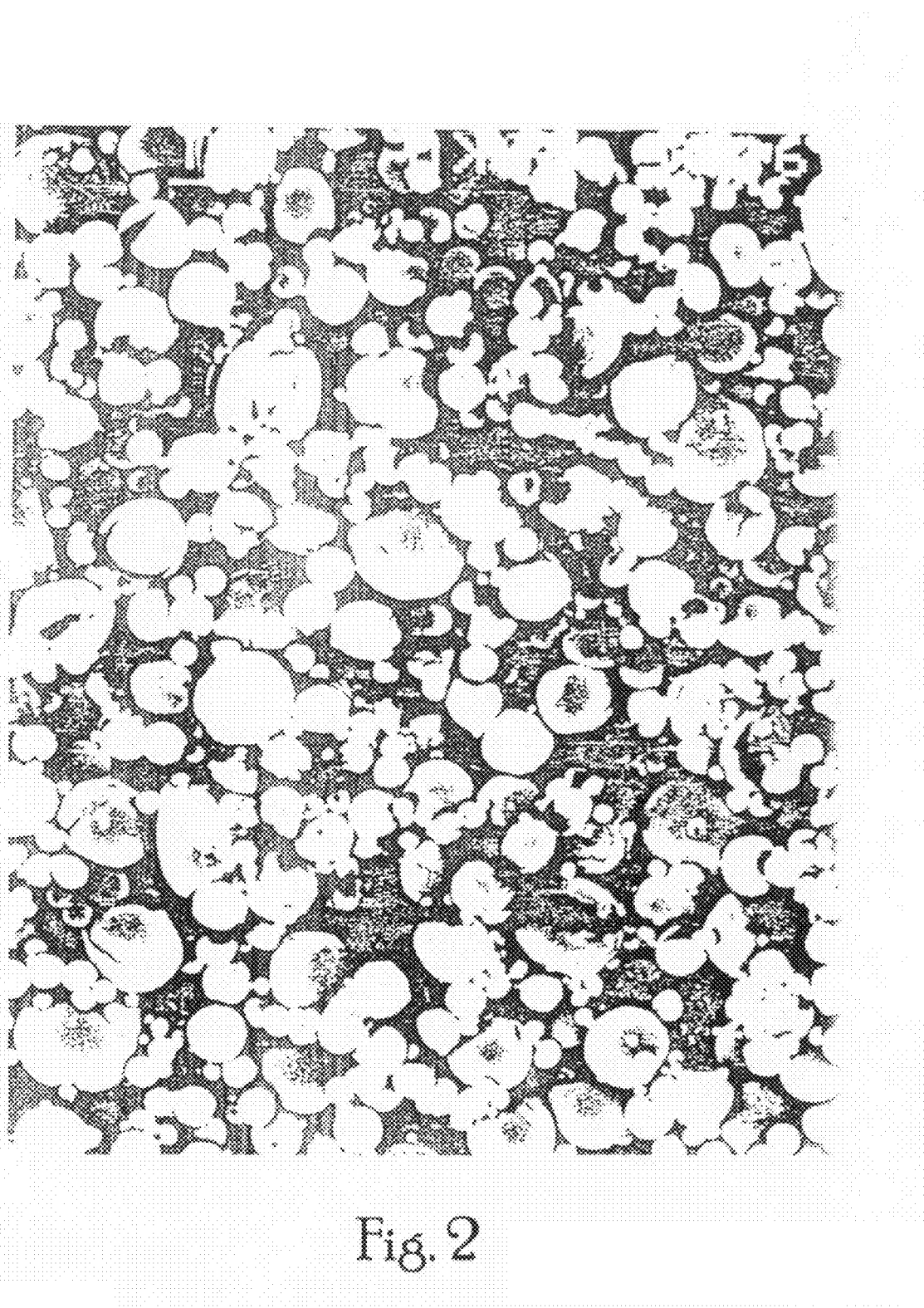
Figure 3A:
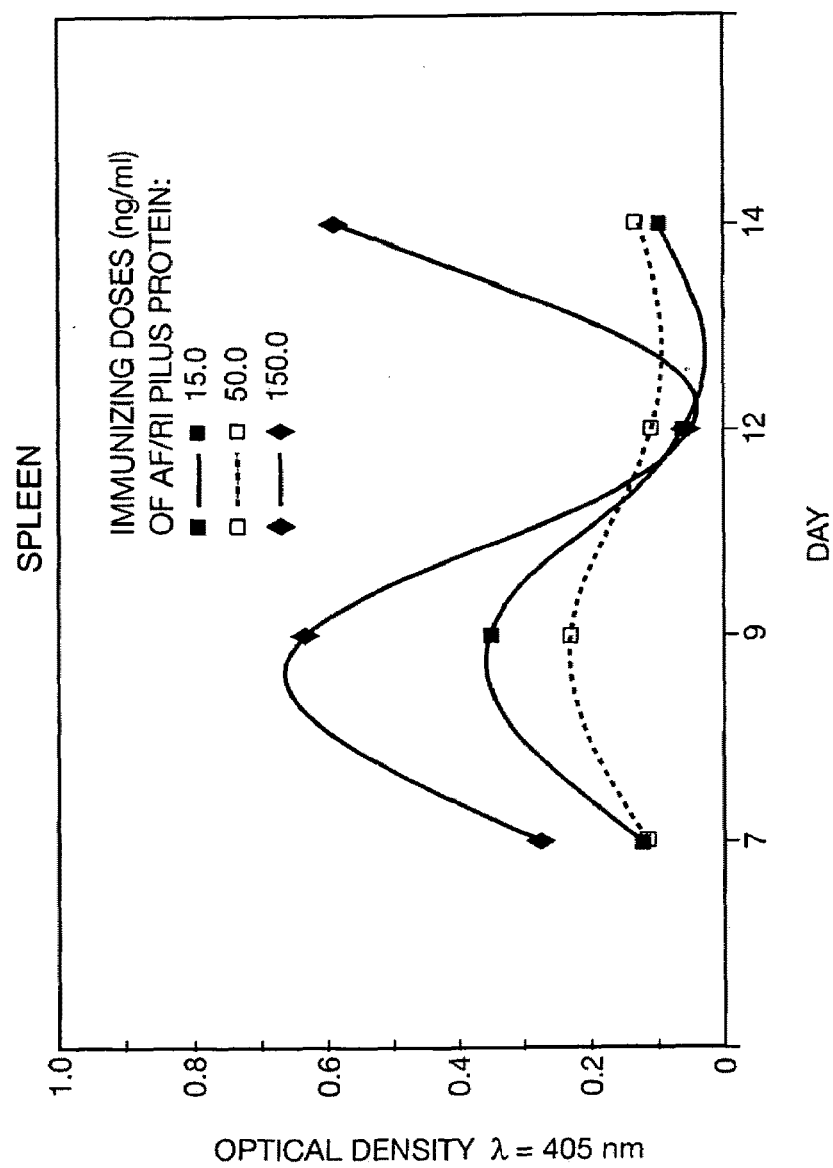
Figure 3B:
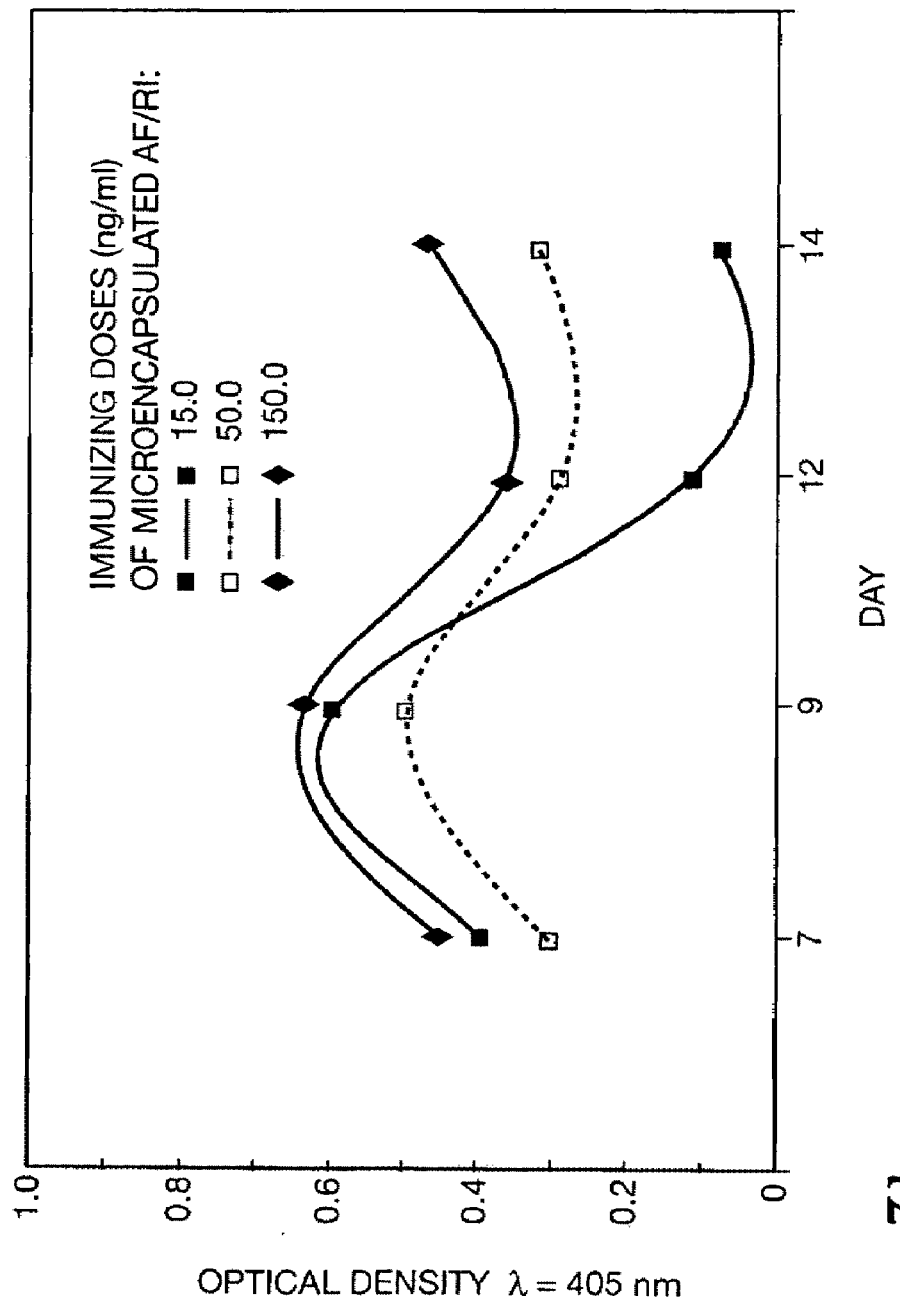
Figure 4A:
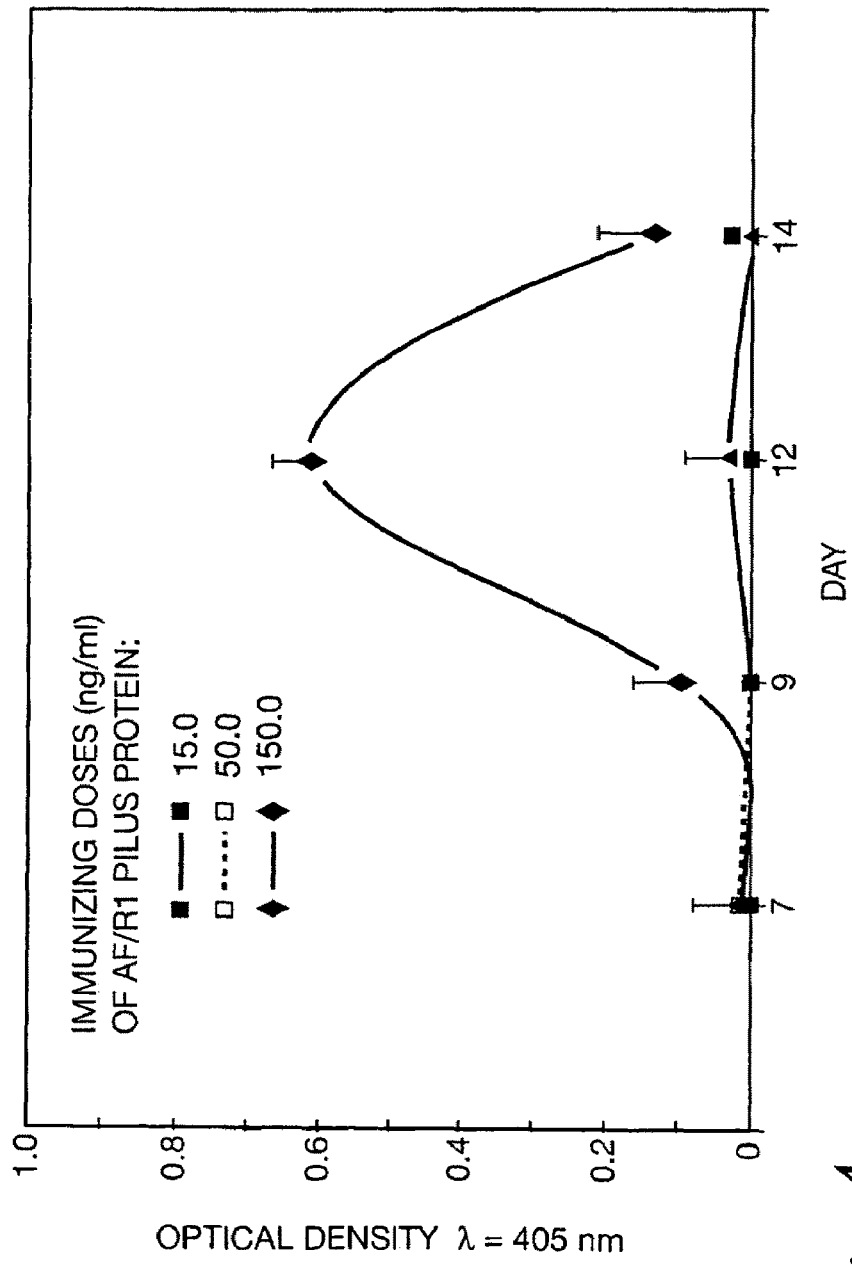
Figure 4B:
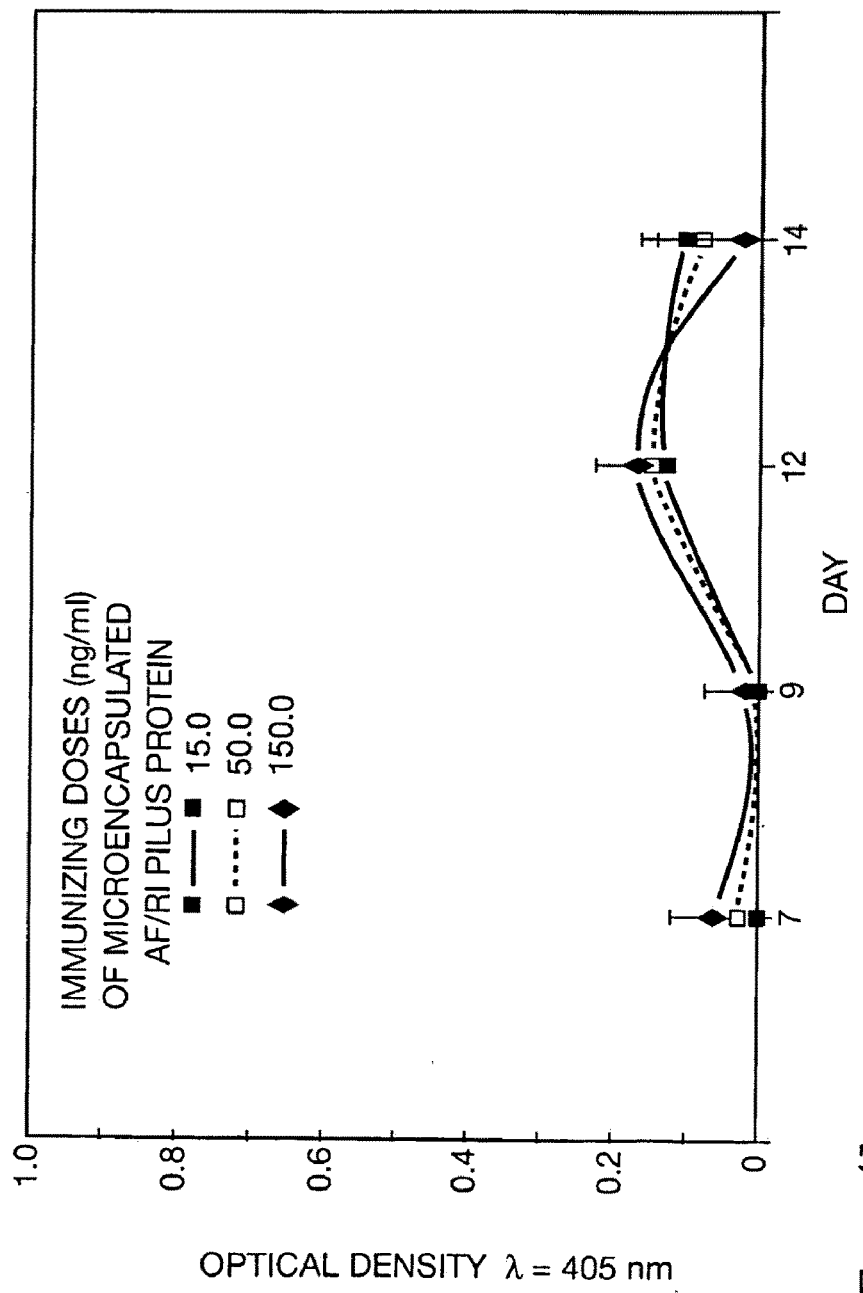

Lymphocyte proliferation of monkey spleen cells to CFA/I synthetic peptides. To determine which segments of the CFA/I protein are able to stimulate proliferation of CFA/I immune primate lymphocytes in vitro, three Rhesus monkeys were immunized with CFA/I subunits, and their splenic lymphocytes were cultured with synthetic overlapping decapeptides which represented the entire CF/I sequence. Concentrations of peptides used as antigen were 6.0, 0.6, and 0.6 ug/ml. Proliferative responses to the decapeptides were observed in each of the three monkeys (FIGS. 1-3). The majority of the responses occurred at the 0.6 and 0.06 ug/ml concentrations of antigen and within distinct regions of the protein (peptides beginning with residues 8-40, 70-80, and 27-137). A comparison of the responses at the 6.0, 0.6 and 0.06 ug/ml concentrations antigenic peptide for one monkey (2&2) are shown (FIGS. 4-6). Taking into account all concentrations of antigen tested, spleen cells from monkey 184D demonstrated a statistically significant response to decapeptides beginning with CFA/I amino acid residues 3, 4, 8, 12, 15, 21, 26, 28, 33, 88, 102, 10, 133, 134, and 136 (FIG. 19). Monkey 34 had a significant response to decapeptides beginning with residues 24, 31, 40, 48, 71, 72, 77, 78, 80, 87, and 102, 126 and 133 (FIG. 20); monkey 2Z2 responded to decapeptides which began with residues 4, 9, 11, 12, 13, 14, 15, 16, 17, 20, 27, 35, 73, 79, 18, 127, 129, 132, and 133 (FIG. 19). Peptides beginning with amino acid residues 3 through 2 were synthesized with either a glutamic acid or an asparagine substituted for the aspartic acid residue at position twelve to prevent truncated peptides. The observed responses to peptides beginning with residue 8 (monkey 184d), and residues 9, 11, 12 (monkey 2Z2) occurred in response to peptides that had the glutamic acid substitution. However, the observed responses to peptides beginning with residue 3, 4, and 12 (monkey 184D), a well as residue 4 (monkey 2Z2) occurred in response to peptides that had the asparagine substitution. Monkey 34 did not respond to any of the peptides that had the substitution at position twelve. All other responses shown were to the natural amino acid sequence of the CFA/I protein. Statistical significance was determined by comparing the cpm of quadruplicate wells cultured with the CFA/I peptides to the cpm of wells cultured with the CFA/I peptides to the cpm of wells cultured with a control peptide.

Analysis of decapeptides that supported proliferation of lymphocytes from CFA/I immune animals. Of the 39 different peptides that supported proliferative responses, thirty contained a serine residue, 19 contained a serine at either position 2, 3, or 4, and nine had a serine specifically at position 3. Some of the most robust responses were to the peptides that contained a serine residue at the third position. The amino acid sequence of four such peptides is shown in Table 3.

LITERATURE CITED

1. Mooi, F. R., and F. K. de Graaf. 1985. Molecular biology of fimbriae of enterotoxigenic *Escherichia coli*. Curr. Top. Microbiol. Immunol. 118:119-138.
2. Evans, D. G., D. J. Jr. Evans, S. Clegg, and J. A. Pauley. 1979. Purification and characterization of the CFA/I antigen of enterotoxigenic *Escherichia coli*. Infect. Immun. 25:738-748.
3. Evans, D. G., D. J. Jr. Evans, W. S. Tjoa, and H. L. Dupont. 1978. Detection and characterization of colonization factor enterotoxigenic *Escherichia coli* isolated from adults with diarrhea. Infect. Immun. 19:727-736.
4. McConnell, M. M., H. Chart, and B. Rowe. 1989. Antigenic homology within human enterotoxigenic *Escherichia coli* fimbrial colonization factor antigens —CFA/I, coli-surface-associated antigens (Cs)1, Cs2, Cs4, and Cs17, FEMS Micro. Lett. 61:105-108.
5. Cheney, C. P., and E. C. Boedeker. 1983. Adherence of an enterotoxigenic *Escherichia coli* strain, serotype 078:H11, to purified human intestinal brush borders. Infect. Immun. 39:1280-11284.
6. Miles, M. A., G. R. Wallace, and J. L. Clarke. 1989. Multiple peptide synthesis (Pepscan method) for the systematic analysis of B- and T-cell epitopes: application to parasite proteins. Parasitology Today 5:397-400.
7. Rothbard, J. B., and W. R. Taylor. 1988. A sequence pattern common to T cell epitopes. EMBO. J. 7:93-100.
8. DeLisi, C., and J. A. Berzofsky. 1985. T-cell antigenic sites tend to be amphipathic structures. Proc. Natl. Acad. Sci, USA 82:7048-7052.
9. Margalit, H., J. L. Spounge, J. L. Cornette, K. B. Cease, C. DeLisi, and J. A. Berzofsky. 1987. Prediction of Immunodominant helper T cell antigenic sites from the primary sequence. J. Immunol. 138:2213-2229.
10. Berzofsky, J. A. 1988. Structural basis of antigen recognition by T lymphocytes. J. Clin. Invest. 82:1811-1817.
11. Stille, C. J., L. J. Thomas, V. E. Reyes, and R. E. Humphreys. 1987. Hydrophobic strip-of-helix algorithm for selection of T cell-presented peptides. Mol. Immunol. 24:1021-1027.
12. Lozzi, L., M. Rustici, M. Corti, M. G. Cusi, P. E. Valensin, L. Bracci, A. Santucci, P. Soldani, A. Spreafico, and P. Neri. 1990. Structure of rebella El glycoprotein epitopes established by multiple peptide synthesis. Arch. Virol. 110:271-276.
13. Troalen, F., A. Razafindratsita, A. Puisieux, T. Voeltzel, C. Bohuon, D. Bellet, and J. M. Bidart. 1990. Structural probing of human lutropin using antibodies raised against synthetic peptides constructed by classical and multiple antigen peptide system approaches. Mol. Immunol. 27:363-368.
14. Tan, X. H., M. Ratnam, S. M. Huang, P. L. Smith, and J. H. Freisheim. 1990. Mapping the antigenic epitopes of human dihydrofolate reductase by systematic synthesis of peptides on solid supports. J. Biol. Chem. 265:8022-8026.
15. Van der Zee, R., W. Van Eden, R. H. Meloen, A. Noordzij, and J. Van Embden. 1989. Efficient mapping and characterization of a T cell epitope by the simultaneous synthesis of multiple peptides. Eur. J. Immunol. 19:43-47.
16. Geysen, H. M., R. H. Meloen, and S. J. Barteling. 1984. Use of peptide synthesis to probe viral antigens for epitopes to a solution of a single amino acid. Proc. Natl. Acad. Sci. USA 81:3998-4002.
17. Isaacson, R. E. 1977. K99 surface antigen of *Escerichia coli*: Purification and partial characterization. Infect. Immun. 15:272-279.
18. Klemm, P. 1982. Primary structure of the CFA1 fimbrial protein from human enterotoxigenic *Escherichia coli* strains. Eur. 124:339-348.
19. Devereux, J., P. Haeberli, and O, Smithies. 1984. A comprehensive set of sequence analysis programs for the VAX. Nucleic Acids Res. 12:387-395.
20. Hall, R. H., D. J. Maneval, J. H. Collins, J. L. Theibert and M. M. Levine. (1989). Purification and analysis of colonization factor antigen I, coli surface antigen 1, and coli surface antigen 3 fimbriae from enterotoxigenic *Escherichia coli*. J. Bacteriol. 171, 6372-4.
21. Karjalainen, T. K., D. G. Evans, M. So and C. H. Lee. (1989). Molecular cloning and nucleotide sequence of the colonization factor antigen I gene of *Escherichia coli*. Infect Immun. 57, 1126-30.
22. Kraitzen, H. D., J. Wiltfang, M. Karas, V. Neuhoff, and N. Hilschmann. (1989) Gas-phase sequencing after electroblotting on polyvinylidene difluoride membranes assigns correct molecular weights to myoglobin molecular weight markers. Anal. Biochem. 183, 1-8.
23. Matsiduria, P. 1987. Sequence from picomole quantities of proteins electroblotted onto polyvinylidene diflouride membranes. J. Biol. Chem. 262, 10035-10038.
24. Schagger, H. and G. von Jagow. 1987. Tricine-sodium dodecyl sulfate-polyacrylamide gel electrophoresis for the separation of proteins in the range of 1 to 100 kKa. Anal. Biochem. 166, 368-379.

We claim:

1. A method for inducing an immune response in mammals comprising administering a pharmaceutical composition comprising an antigenic synthetic peptide containing CFA/I pilus protein T-cell epitopes encapsulated within a biodegradable polymeric matrix comprising poly (DL-lactide-co-glycolide) having a relative ratio between the amount of lactide and glycolide components within the range of 48:52 to 58:42, wherein the CFA-I pilus protein T-cell epitopes consist of the amino acid sequence:
   (SEQ ID NO: 1) [4] (Asn-Ile-Thr-Val-Thr-Ala-Ser-Val-Asp-Pro),
   (SEQ ID NO: 11) (Gly-Asn-Tyr-Ser-Gly-Val-Val-Ser-Leu-Val), and mixtures thereof.

2. The method in accordance with claim 1 wherein said antigenic synthetic peptide is present in an amount of 0.1% to 1% by weight of said composition and said polymer is present in an amount of 99% to 99.9% by weight of said composition.

3. A composition for inducing an immune response in mammals comprising of an antigenic synthetic peptide containing CFA-1 pilus protein T-Cell epitopes encapsulated within a biodegradable-biocompatible poly(DL-lactide-co-glycolide) polymeric matrix, wherein said antigenic synthetic peptide is present in an amount of 0.1% to 1% by weight of said vaccine and said polymer is present in an amount of 99% to 99.9% by weight of said vaccine, wherein the CFA/I pilus protein T-cell epitopes consist of the amino acid sequence:
   (SEQ ID NO: 1) [4] (Asn-Ile-Thr-Val-Thr-Ala-Ser-Val-Asp-Pro),
   (SEQ ID NO: 11) (Gly-Asn-Tyr-Ser-Gly-Val-Val-Ser-Leu-Val), and mixtures thereof.

4. The composition according to claim 3 wherein the polymeric matrix is poly(DL-lactide-co-glycolide).

5. The composition according to claim 4 wherein the relative ratio of lactide to glycolide component is within the range of 40:60 to 0:100.

6. The composition according to claim 5 wherein the relative ratio of lactide to glycolide components is within the range of 48:52 to 58:42.

\* \* \* \* \*

```
                        SEQUENCE LISTING

<160> NUMBER OF SEQ ID NOS: 39

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Asn Ile Thr Val Thr Ala Ser Val Asp Pro
 1               5                  10

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Thr Ala Ser Val Asp Pro Val Ile Asp Leu
 1               5                  10

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Asp Pro Val Ile Asp Leu Leu Gln Ala Asp
 1               5                  10

<210> SEQ ID NO 4
```

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ile Asp Leu Leu Gln Ala Asp Gly Asn Ala
 1               5                  10

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ala Asp Gly Asn Ala Leu Pro Ser Ala Val
 1               5                  10

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Pro Ser Ala Val Lys Leu Ala Tyr Ser Pro
 1               5                  10

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Leu Asn Ser Thr Val Gln Met Pro Ile Ser
 1               5                  10

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Met Pro Ile Ser Val Ser Trp Gly Gly Gln
 1               5                  10

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9
```

```
Gln Val Leu Ser Thr Thr Ala Lys Glu Phe
  1               5                  10

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ala Gly Thr Ala Pro Thr Ala Gly Asn Tyr
  1               5                  10

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Asn Tyr Ser Gly Val Val Ser Leu Val
  1               5                  10

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Lys Ala Ile Thr Val Thr Ala Ser Val
  1               5

<210> SEQ ID NO 13
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Val Asp Pro Val Ile Asp Leu Leu Gln Ala Asp
  1               5                  10

<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Asn Ala Leu Pro Ser Ala Val
  1               5

<210> SEQ ID NO 15
<211> LENGTH: 17
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 15

Ala Tyr Ser Pro Ala Ser Lys Thr Phe Lys Thr Phe Glu Ser Tyr Arg
 1               5                  10                  15
Val

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ala Tyr Ser Pro Ala Ser Lys Thr Phe
 1               5

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Lys Thr Phe Glu Ser Tyr Arg Val
 1               5

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Pro Gln Leu Thr Asp Val Leu Asn Ser
 1               5

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ala Lys Glu Phe Glu Ala Ala Ala
 1               5

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Lys Thr Ala Gly Thr Ala Pro Thr
 1               5
```

```
<210> SEQ ID NO 21
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Thr Ala Pro Thr Ala Gly Asn Tyr Ser
 1               5                  10

<210> SEQ ID NO 22
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Lys Thr Ala Gly Thr Ala Pro Thr Ala Gly Asn Tyr Ser
 1               5                  10

<210> SEQ ID NO 23
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Lys Asn Ile Thr Val Thr Ala Ser Val Asp Pro
 1               5                  10

<210> SEQ ID NO 24
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Thr Ala Ser Val Asp Pro Val Ile Asp Leu Leu Gln Ala Asp
 1               5                  10

<210> SEQ ID NO 25
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ala Gly Thr Ala Pro Thr Ala Pro Thr Ala Gly Asn Tyr Ser
 1               5                  10

<210> SEQ ID NO 26
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 26

Asp Thr Asn Ala Asp Lys Glu Ile Lys Ala Gly Gln Asn Thr Val Asp
 1               5                  10                  15

<210> SEQ ID NO 27
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Thr Asn Ala Gly Thr Asp Ile Gly Val Asn Gly Ile Gly Asn Leu Ser
 1               5                  10                  15

<210> SEQ ID NO 28
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Thr Asn Ala Gly Thr Asp Ile Gly Ala Asn Lys Ser Phe Thr Leu Lys
 1               5                  10                  15

<210> SEQ ID NO 29
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Val Asn Gly Ile Gly Asn Leu Ser Gly Lys Ala Ile Asp Ala His Val
 1               5                  10                  15

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Val Asp Pro Val Ile Asp Leu Leu Gln
 1               5

<210> SEQ ID NO 31
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gly Pro Ala Pro Thr
 1               5

<210> SEQ ID NO 32
<211> LENGTH: 8
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Pro Gln Leu Thr Asp Val Leu Asn
  1               5

<210> SEQ ID NO 33
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Phe Glu Ser Tyr Arg Val Met Thr Gln Val
  1               5                  10

<210> SEQ ID NO 34
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Asn Tyr Ser Gly Val Val Ser Leu Val Met
  1               5                  10

<210> SEQ ID NO 35
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Leu Ala Asp Thr Pro Gln Leu Thr Asp Val Leu Asn Ser Thr Val Gln
  1               5                  10                  15

Met Pro

<210> SEQ ID NO 36
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Ser Tyr Arg Val Met Thr Gln Val His Thr Asn Asp Ala Thr Lys Lys
  1               5                  10                  15

Val Ile Val

<210> SEQ ID NO 37
<211> LENGTH: 147
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 37

Val Glu Lys Asn Ile Thr Val Thr Ala Ser Val Asp Pro Val Ile Asp
  1               5                  10                  15

Leu Leu Gln Ala Asp Gly Asn Ala Leu Pro Ser Ala Val Lys Leu Ala
             20                  25                  30

Tyr Ser Pro Ala Ser Lys Thr Phe Glu Ser Tyr Arg Val Met Thr Gln
         35                  40                  45

Val His Thr Asn Asp Ala Thr Lys Lys Val Ile Val Lys Leu Ala Asp
     50                  55                  60

Thr Pro Gln Leu Thr Asp Val Leu Asn Ser Thr Val Gln Met Pro Ile
 65                  70                  75                  80

Ser Val Ser Trp Gly Gly Gln Val Leu Ser Thr Thr Ala Lys Glu Phe
                 85                  90                  95

Glu Ala Ala Ala Leu Gly Tyr Ser Ala Ser Gly Val Asn Gly Val Ser
                100                 105                 110

Ser Ser Gln Glu Leu Val Ile Ser Ala Ala Pro Lys Thr Ala Gly Thr
            115                 120                 125

Ala Pro Thr Ala Gly Asn Tyr Ser Gly Val Val Ser Leu Val Met Thr
        130                 135                 140

Leu Gly Ser
145

<210> SEQ ID NO 38
<211> LENGTH: 147
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Val Glu Lys Asn Ile Thr Val Thr Ala Ser Val Asp Pro Val Ile Asp
  1               5                  10                  15

Leu Leu Gln Ala Asp Gly Asn Ala Leu Pro Ser Ala Val Lys Leu Ala
             20                  25                  30

Tyr Ser Pro Ala Ser Lys Thr Phe Glu Ser Tyr Arg Val Met Thr Gln
         35                  40                  45

Val His Thr Asn Asp Ala Thr Lys Lys Val Ile Val Lys Leu Ala Asp
     50                  55                  60

Thr Pro Gln Leu Thr Asp Val Leu Asn Ser Thr Val Gln Met Pro Ile
 65                  70                  75                  80

Ser Val Ser Trp Gly Gly Gln Val Leu Ser Thr Thr Ala Lys Glu Phe
                 85                  90                  95

Glu Ala Ala Ala Leu Gly Tyr Ser Ala Ser Gly Val Asn Gly Val Ser
                100                 105                 110

Ser Ser Gln Glu Leu Val Ile Ser Ala Ala Pro Lys Thr Ala Gly Thr
            115                 120                 125

Ala Pro Thr Ala Gly Asn Tyr Ser Gly Val Val Ser Leu Val Met Thr
        130                 135                 140

Leu Gly Ser
145

<210> SEQ ID NO 39
<211> LENGTH: 147
<212> TYPE: PRT
<213> ORGANISM: Artificial Sequence
```

-continued

```
<220> FEATURE:
<223> OTHER INFORMATION: Description of Artificial Sequence: Synthetic
      peptide

<400> SEQUENCE: 39

Val Glu Lys Asn Ile Thr Val Thr Ala Ser Val Asp Pro Val Ile Asp
 1               5                  10                  15

Leu Leu Gln Ala Asp Gly Asn Ala Leu Pro Ser Ala Val Lys Leu Ala
            20                  25                  30

Tyr Ser Pro Ala Ser Lys Thr Phe Glu Ser Tyr Arg Val Met Thr Gln
        35                  40                  45

Val His Thr Asn Asp Ala Thr Lys Lys Val Ile Val Lys Leu Ala Asp
    50                  55                  60

Thr Pro Gln Leu Thr Asp Val Leu Asn Ser Thr Val Gln Met Pro Ile
65                  70                  75                  80

Ser Val Ser Trp Gly Gly Gln Val Leu Ser Thr Thr Ala Lys Glu Phe
                85                  90                  95

Glu Ala Ala Ala Leu Gly Tyr Ser Ala Ser Gly Val Asn Gly Val Ser
            100                 105                 110

Ser Ser Gln Glu Leu Val Ile Ser Ala Ala Pro Lys Thr Ala Gly Thr
        115                 120                 125

Ala Pro Thr Ala Gly Asn Tyr Ser Gly Val Val Ser Leu Val Met Thr
    130                 135                 140

Leu Gly Ser
145
```